United States Patent
Berry et al.

(10) Patent No.: US 6,372,457 B1
(45) Date of Patent: Apr. 16, 2002

(54) PROCESS AND MATERIALS FOR PRODUCTION OF GLUCOSAMINE

(75) Inventors: Alan Berry; Richard P. Burlingame, both of Manitowoc; James R. Millis, Kohler, all of WI (US)

(73) Assignee: Arkion Life Sciences LLC, Wilmington, DE (US)

( * ) Notice: Subject to any disclaimer, the term of this patent is extended or adjusted under 35 U.S.C. 154(b) by 0 days.

(21) Appl. No.: 09/115,475

(22) Filed: Jul. 15, 1998

Related U.S. Application Data

(63) Continuation-in-part of application No. PCT/US98/00800, filed on Jan. 14, 1998.
(60) Provisional application No. 60/035,494, filed on Jan. 14, 1997.

(51) Int. Cl.$^7$ ................................................. C12P 19/00
(52) U.S. Cl. ........................ 435/72; 435/41; 435/183; 435/193; 435/252.33; 536/23.1
(58) Field of Search ................................ 536/23.1, 23.7; 435/183, 41, 193, 72, 252.33

(56) References Cited

PUBLICATIONS

Bearne, 1996, *J. Biol. Chem.*, 271:3052–3057.
Brown et al., 1989, *Biochem. Soc. Trans.*, 18:317–318.
Cochet et al., 1995, *Arch. Biochem. Biophys.*, 324:391–400.
Daniels et al., 1993, *Mol. Endrocinology*, 7:1041–1048.
Denisot et al., 1991, *Arch. Biochem. Biophys.*, 288:225–230.
Elliot et al., 1975, *Biochem. Biophys. Res. Comm.*, 64:277–281.
Golinelli–Pimpaneau eta l., 1991, *Eur. J. Biochem*, 201:175–182.
Leriche et al., 1996, *J. Am. Chem. Soc.*, 118:1797–1798.
Leriche et al., 1997, *Eur. J. Biochem.*, 245:418–422.
Marie et al., 1992, *Mol. Microbiol.*, 6:843–854.
McKnight et al., 1992, *J. Biol. Chem.*, 267:25208–25212.
Milewski, 1993, *Biochim. Biophys. Acta*, 1161:279–284.
Obmolova et al., 1994, *J. Mol. Biol.*, 242:703–705.
Oppon et al., *J. Bacteriology*, 180:3007–3012.
Smith et al., 1996, *J. Bacteriology*, 178:2320–2327.
Teplyakov et al., 1998, *Structure*, 6:1047–1055.
Watzele et al., 1989, *J. Biol. Chem.*, 264:8753–8758.
Zalkin. Glucosamine–6–phosphate synthase. Methods in Enzymology. 1985, vol 113, pp. 278–281.*
Talent et al. Pilot study of oral polymeric N–acetyl–D–glucosamine as a potential treatment for patients with osteoarthritis. Clin Ther. Nov.–Dec. 1996, Vol 18, pp. 1184–1190.*
Tesoriere et al. dephosphorylation of glucosamine 6–phosphate in rat liver homogenates. G. Biochim. 1967, Vol 16, pp. 209–214 (Abstract).*
Milewski et al. Purification and characterization of glucosamine–6–phosphate synthase from Saccharomyces cerevisiae. Adv. Chitin Sci. 1996, Vol. 1, pp. 96–101.*
Plumbridge. GenBank Accession X14135. Mar. 21, 1994.*
Peri et al. GenBank Accession M19284. Feb. 16, 1994.*
Rogers. GenBank Accession AAA24192. Feb. 16, 1994.*
Dutka–et al. Molecular cloning and overexpressio nof the gluosamine synthase gene from *Escherichia coli*. Biochimie. 1998, Vol. 70, pp. 287–290, especially p. 288.*
O'shea et al. Detection of carbohydrates by capillary electophoresis with pulsed amperometric detection. Anal. Chem. 1993, Vol 65, pp. 948–951, especially p. 950.*
Balbas et al. A pBRINT family of plasminds for integration of cloned DNA into the *Escherichia coli* chromosome. Gene. 1996, Vol. 172, pp. 65–69.*
Joyce et al. Method for determining whether a gene of *Escherichia coli* is essential: application to the polA gene. Journal of Bacteriology. 1984, May, Vol. 158, pp. 636–643.*
GenBank Accession L10328. 1995.*

* cited by examiner

Primary Examiner—Nashaat T. Nashed
Assistant Examiner—Christian L Fronda
(74) *Attorney, Agent, or Firm*—Sheridan Ross P.C.

(57) ABSTRACT

The present invention relates to a method and materials for producing glucosamine by fermentation of a genetically modified microorganism. Included in the present invention are genetically modified microorganisms useful in the present method for producing glucsamine, as well as recombinant nucleic acid molecules and the proteins produces by such recombinant nucleic acid molecules.

59 Claims, 21 Drawing Sheets

US 6,372,457 B1

PROCESS AND MATERIALS FOR PRODUCTION OF GLUCOSAMINE

CROSS REFERENCE TO RELATED APPLICATIONS

This application is a continuation-in-part application of PCT application Ser. No. PCT/US Ser. No. 98/00800, filed Jan. 14, 1998, which designates the U.S. PCT/US Ser. No. 98/00800 claims priority under 35 U.S.C. § 119(e) from U.S. Provisional Application Serial No. 60/035,494, filed Jan. 14, 1997. Both PCT Application Serial No. PCT/US Ser. No. 98/00800 and U.S. Provisional Application Serial No. 60/035,494 are incorporated herein by reference in their entireties.

FIELD OF THE INVENTION

The present invention relates to a method for producing glucosamine by fermentation. The present invention also relates to genetically modified strains of microorganisms useful for producing glucosamine.

BACKGROUND OF THE INVENTION

Amino sugars are usually found as monomer residues in complex oligosaccharides and polysaccharides. Glucosamine is an amino derivative of the simple sugar, glucose. Glucosamine and other amino sugars are important constituents of many natural polysaccharides. For example, polysaccharides containing amino sugars can form structural materials for cells, analogous to structural proteins.

Glucosamine is manufactured as a nutraceutical product with applications in the treatment of osteoarthritic conditions in animals and humans. The market for glucosamine is experiencing tremendous growth. Furthermore, significant erosion of the world market price for glucosamine is not expected.

Glucosamine is currently obtained by acid hydrolysis of chitin, a complex carbohydrate derived from N-acetyl-D-glucosamine. Alternatively, glucosamine can also be produced by acid hydrolysis of variously acetylated chitosans. These processes suffer from poor product yields (in the range of 50% conversion of substrate to glucosamine). Moreover, the availability of raw material (i.e., a source of chitin, such as crab shells) is becoming increasingly limited. Therefore, there is a need in the industry for a cost-effective method for producing high yields of glucosamine for commercial sale and use.

SUMMARY OF THE INVENTION

One embodiment of the present invention relates to a method to produce glucosamine by fermentation of a microorganism. This method includes the steps of: (a) culturing in a fermentation medium a microorganism having a genetic modification in an amino sugar metabolic pathway; and (b) recovering a product produced from the step of culturing which is selected from the group of glucosamine-6-phosphate and glucosamine. Such an amino sugar metabolic pathway is selected from the group of a pathway for converting glucosamine-6-phosphate into another compound, a pathway for synthesizing glucosamine-6-phosphate, a pathway for transport of glucosamine or glucosamine-6-phosphate out of the microorganism, a pathway for transport of glucosamine into the microorganism, and a pathway which competes for substrates involved in the production of glucosamine-6-phosphate. The fermentation medium includes assimilable sources of carbon, nitrogen and phosphate. In a preferred embodiment, the microorganism is a bacterium or a yeast, and more preferably, a bacterium of the genus Escherichia, and even more preferably, *Escherichia coli*.

In one embodiment, the product can be recovered by recovering intracellular glucosamine-6-phosphate from the microorganism and/or recovering extracellular glucosamine from the fermentation medium. In further embodiments, the step of recovering can include purifying glucosamine from the fermentation medium, isolating glucosamine-6-phosphate from the microorganism, and/or dephosphorylating the glucosamine-6-phosphate to produce glucosamine. In one embodiment, at least about 1 g/L of product is recovered.

In yet another embodiment, the step of culturing includes the step of maintaining the carbon source at a concentration of from about 0.5% to about 5% in the fermentation medium. In another embodiment, the step of culturing is performed at a temperature of from about 28° C. to about 37° C. In yet another embodiment, the step of culturing is performed in a fermenter.

In one embodiment of the present invention, the microorganism has a modification in a gene which encodes a protein including, but not limited to, N-acetylglucosamine-6-phosphate deacetylase, glucosamine-6-phosphate deaminase, N-acetyl-glucosamine-specific enzyme II$^{Nag}$, glucosamine-6-phosphate synthase, phosphoglucosamine mutase, glucosamine-1-phosphate acetyltransferase-N-acetylglucosamine-1-phosphate uridyltransferase, phosphofructokinase, enzyme II$^{Glc}$ of the PEP:glucose PTS, EIIM, P/III$^{Man}$ of the PEP:mannose PTS, and/or a phosphatase.

In another embodiment, the genetic modification includes a genetic modification which increases the action of glucosamine-6-phosphate synthase in the microorganism. Such a genetic modification includes the transformation of the microorganism with a recombinant nucleic acid molecule encoding glucosamine-6-phosphate synthase to increase the action of glucosamine-6-phosphate synthase and/or to overexpress the glucosamine-6-phosphate synthase by the microorganism. In one embodiment, the recombinant nucleic acid molecule is operatively linked to a transcription control sequence. In a further embodiment, the recombinant nucleic acid molecule is integrated into the genome of the microorganism. In yet another embodiment, the recombinant nucleic acid molecule encoding glucosamine-6-phosphate synthase has a genetic modification which increases the action of the synthase. Such genetic modifications can result in reduced glucosamine-6-phosphate product inhibition of the glucosamine-6-phosphate synthase, for example.

In one embodiment, a recombinant nucleic acid molecule of the present invention which comprises a nucleic acid sequence encoding a glucosamine-6-phosphate synthase encodes an amino acid sequence SEQ ID NO:16. In another embodiment, such a recombinant nucleic acid molecule comprises a nucleic acid sequence selected from the group of SEQ ID NO:13, SEQ ID NO:14 or SEQ ID NO:15. Preferred recombinant nucleic acid molecules of the present invention include pKLN23-28, nglmS-28$_{2184}$ and nglmS-28$_{1830}$.

Also included in the present invention are recombinant nucleic acid molecules encoding a glucosamine-6-phosphate synthase which comprises a genetic modification which increases the action of the glucosamine-6-phosphate synthase (i.e., a glucosamine-6-phosphate synthase homologue). Such a genetic modification can reduce glucosamine-6-phosphate product inhibition of the synthase, for example. In one embodiment, such a genetic modification in a recombinant nucleic acid molecule of the present invention which encodes a glucosamine-6-phosphate synthase results in at least one amino acid modification selected from the group of an addition, substitution, deletion, and/or derivatization of an amino acid residue of the glucosamine-6-phosphate synthase. In one embodiment, such an amino acid modification is in an amino acid sequence position in the modified protein (i.e., homologue) which corresponds to one or more of the following amino acid positions in amino acid sequence SEQ ID NO:16: Ile(4), Ile(272), Ser(450), Ala(39), Arg(250), Gly(472), Leu(469). In another embodiment, such an amino acid modification is selected from the group of a substitution of: (a) an amino acid residue having an aliphatic hydroxyl side group for Ile(4); (b) an amino acid residue having an aliphatic hydroxyl side group for Ile(272); (c) an amino acid residue having an aliphatic side group for Ser(450); (d) an amino acid residue having an aliphatic hydroxyl side group for Ala(39); (e) an amino acid residue having a sulfur-containing side group for Arg(250); (f) an amino acid residue having an aliphatic hydroxyl side group for Gly(472); (g) an amino acid residue having an aliphatic side group for Leu(469); and, (h) combinations of (a)–(g).

In yet another embodiment of the present invention, an amino acid modification as described above is preferably a substitution selected from the group of: Ile(4) to Thr, Ile (272) to Thr, Ser(450) to Pro, Ala(39) to Thr, Arg(250) to Cys, Gly(472) to Ser, Leu(469) to Pro, and combinations thereof.

In another embodiment, a genetically modified recombinant nucleic acid molecule of the present invention comprises a nucleic acid sequence encoding glucosamine-6-phosphate synthase comprising an amino acid sequence selected from the group of SEQ ID NO:19, SEQ ID NO:22, SEQ ID NO:25, SEQ ID NO:28 or SEQ ID NO:31. In another embodiment, a genetically modified recombinant nucleic acid molecule of the present invention comprises a nucleic acid sequence selected from the group of SEQ ID NO:17, SEQ ID NO:18, SEQ ID NO:20, SEQ ID NO:21, SEQ ID NO:23, SEQ ID NO:24, SEQ ID NO:26, SEQ ID NO:27, SEQ ID NO:29 and SEQ ID NO:30. Preferred genetically modified recombinant nucleic acid molecule of the present invention include pKLN23-49, pKLN23-54, pKLN23-124, pKLN23-149, pKLN 23-151, nglmS-49$_{2184}$, nglmS-49$_{1830}$, nglmS-54$_{2184}$, nglmS-54$_{1830}$, nglmS-124$_{2184}$, nglmS-124$_{1830}$, nglmS-149$_{2184}$, nglmS-149$_{1830}$, nglmS-151$_{2184}$ and nglmS-151$_{1830}$.

Another embodiment of the present invention relates to a glucosamine-6-phosphate synthase which has glucosamine-6-phosphate synthase action, such synthase being encoded by a nucleic acid sequence having a genetic modification that results in increased glucosamine-6-phosphate synthase action. Such a nucleic acid sequence has been describe above with regard to recombinant nucleic acid molecules of the present invention.

Yet another embodiment of the present invention relates to a method to produce glucosamine by fermentation, such method comprising: (a) culturing in a fermentation medium comprising assimilable sources of carbon, nitrogen and phosphate, a genetically modified microorganism having increased glucosamine-6-phosphate synthase action, wherein the genetically modified microorganism is produced by a process comprising the steps of: 1) generating modifications in an isolated nucleic acid molecule comprising a nucleic acid sequence encoding glucosamine-6-phosphate synthase to create a plurality of modified nucleic acid sequences; (2) transforming microorganisms with the modified nucleic acid sequences to produce genetically modified microorganisms; (3) screening the genetically modified microorganisms for glucosamine-6-phosphate synthase action; and, (4) selecting the genetically modified microorganisms which have increased glucosamine-6-phosphate synthase action; and, (b) recovering the product. The step of culturing produces a product selected from the group of glucosamine-6-phosphate and glucosamine from the microorganism.

In another embodiment, a microorganism of the present invention has an additional genetic modification in genes encoding N-acetylglucosamine-6-phosphate deacetylase, glucosamine-6-phosphate deaminase, N-acetylglucosamine-specific enzyme II$^{Nag}$, phosphoglucosamine mutase, glucosamine-1-phosphate acetyltransferase-N-acetylglucosamine-1-phosphate uridyltransferase, phosphofructokinase, Enzyme II$^{Glc}$ of the PEP:glucose PTS, EIIM,P/III$^{Man}$ of the PEP:mannose PTS, wherein the modification decreases the action of such proteins. In another embodiment, a microorganism of the present invention has an additional genetic modification in a gene encoding a phosphatase, wherein the modification increases the action of the phosphatase. In a preferred embodiment, a microorganism of the present invention has an additional genetic modification in the genes encoding the following proteins: N-acetylglucosamine-6-phosphate deacetylase, glucosamine-6-phosphate deaminase and N-acetylglucosamine-specific enzyme II$^{Nag}$, such modifications including, but not limited to, a deletion of at least a portion of such genes.

Another embodiment of the present invention relates to a method to produce glucosamine by fermentation which includes the steps of (a) culturing an *Escherichia coli* transformed with a recombinant nucleic acid molecule encoding glucosamine-6-phosphate synthase in a fermentation medium comprising assimilable sources of carbon, nitrogen and phosphate to produce a product, and (b) recovering the product. The product includes intracellular glucosamine-6-phosphate which is recovered from the *Escherichia coli* and/or extracellular glucosamine which is recovered from the fermentation medium. In this embodiment, the recombinant nucleic acid molecule increases expression of the glucosamine-6-phosphate synthase by the *Escherichia coli*, and is operatively linked to a transcription control sequence. In one embodiment, the recombinant nucleic acid molecule comprises a genetic modification which reduces glucosamine-6-phosphate product inhibition of the glucosamine-6-phosphate synthase. In another embodiment, the *Escherichia coli* has an additional genetic modification in at least one gene selected from the group of nagqA nagB, nagC, nagD, nagE, manXYZ, glmM, pfkB, pfkA, glmU, glmS, ptsG and/or a phogphatage gene. In yet another embodiment, the additional modification comprises a deletion of nagA, nagB, nagC, nagD, nagE, and a mutation in manXYZ, wherein the modification results in decreased enzymatic activity of N-acetylglucosamine-6-phosphate deacetylase, glucosamine-6-phosphate deaminase and N-acetyl-glucosamine-specific enzyme II$^{Nag}$.

Yet another embodiment of the present invention relates to a microorganism for producing glucosamine by a biosynthetic process. The microorganism is transformed with a recombinant nucleic acid molecule encoding glucosamine-6-phosphate synthase, wherein the recombinant nucleic acid molecule is operatively linked to a transcription control sequence. The recombinant nucleic acid molecule further comprises a genetic modification which increases the action of the glucosamine-6-phosphate synthase. The expression of the recombinant nucleic acid molecule increases production of the glucosamine by the microorganism. In a preferred embodiment, the recombinant nucleic acid molecule is integrated into the genome of the microorganism. In yet another embodiment, the microorganism has at least one additional genetic modification in a gene encoding a protein selected from the group consisting of N-acetylglucosamine-6-phosphate deacetylase, glucosamine-6-phosphate deaminase, N-acetyl-glucosamine-specific enzyme $II^{Nag}$, phosphoglucosamine mutase, glucosamine-1-phosphate acetyltransferase-N-acetylglucosamine-1-phosphate uridyltransferase, phosphofructokinase, Enzyme $II^{Glc}$ of the PEP:glucose PTS, and/or $EIIM,P/III^{Man}$ of the PEP:mannose PTS, wherein the genetic modification decreases the action of the protein. In another embodiment, the microorganism has a modification in a gene encoding a phosphatase, wherein the genetic modification increases the action of the phosphatase. In yet another embodiment, the microorganism has a modification in genes encoding N-acetylglucosamine-6-phosphate deacetylase, glucosamine-6-phosphate deaminase and N-acetylglucosamine-specific enzyme $II^{Nag}$, wherein the genetic modification decreases enzymatic activity of the protein. In a preferred embodiment, the genetic modification is a deletion of at least a portion of the genes.

In a further embodiment, the microorganism is *Escherichia coli*, having a modification in a gene selected from the group of nagA, nagB, nagC, nagD, nagE, manXYZ, glmM, pfkB, pfkA, glmU, ptsG and/or a phosphatase gene. In one embodiment, such an *Escherichia coli* has a deletion of nag regulon genes, and in another embodiment, such an *Escherichia coli* has a deletion of nag regulon genes and a genetic modification in manXYZ genes such that the proteins encoded by the manXYZ genes have decreased action.

Yet another embodiment of the present invention is a microorganism as described above which produces at least about 1 g/L of glucosamine when cultured for about 10–60 hours at from about 28° C. to about 37° C. to a cell density of at least about 8 g/L by dry cell weight, in a pH 7.0 fermentation medium comprising: 14 g/L $K_2HPO_4$, 16 g/L $KH_2PO_4$, 1 g/L $Na_3Citrate.2H_2O$, 5 g/L $(NH_4)_2SO_4$, 20 g/L glucose, 10 mM $MgSO_4$, 1 mM $CaCl_2$, and from about 0.2 mM to about 1 mM IPTG.

Another embodiment of the present invention is a microorganism for producing glucosamine by a biosynthetic process, which includes: (a) a recombinant nucleic acid molecule encoding glucosamine-6-phosphate synthase operatively linked to a transcription control sequence; and, (b) at least one genetic modification in a gene encoding a protein selected from the group of N-acetylglucosamine-6-phosphate deacetylase, glucosamine-6-phosphate deaminase, N-acetyl-glucosamine-specific enzyme $II^{Nag}$, phosphoglucosamine mutase, glucosamine-1-phosphate acetyltransferase-N-acetylglucosamine-1-phosphate uridyltransferase, phosphofructokinase, Enzyme $II^{Glc}$ of the PEP:glucose PTS, and/or $EIIM,P/III^{Man}$ of the PEP:mannose PTS, wherein the genetic modification decreases the action of the protein. In another embodiment, the microorganism includes at least one genetic modification in a gene encoding a phosphatase, wherein the genetic modification increases the action of the phosphatase. Expression of the recombinant nucleic acid molecule increases the action of the glucosamine-6-phosphate synthase in the microorganism. In a further embodiment, the recombinant nucleic acid molecule is integrated into the genome of the microorganism.

BRIEF DESCRIPTION OF THE FIGURES OF THE INVENTION

DETAILED DESCRIPTION OF THE INVENTION

Figure 1:
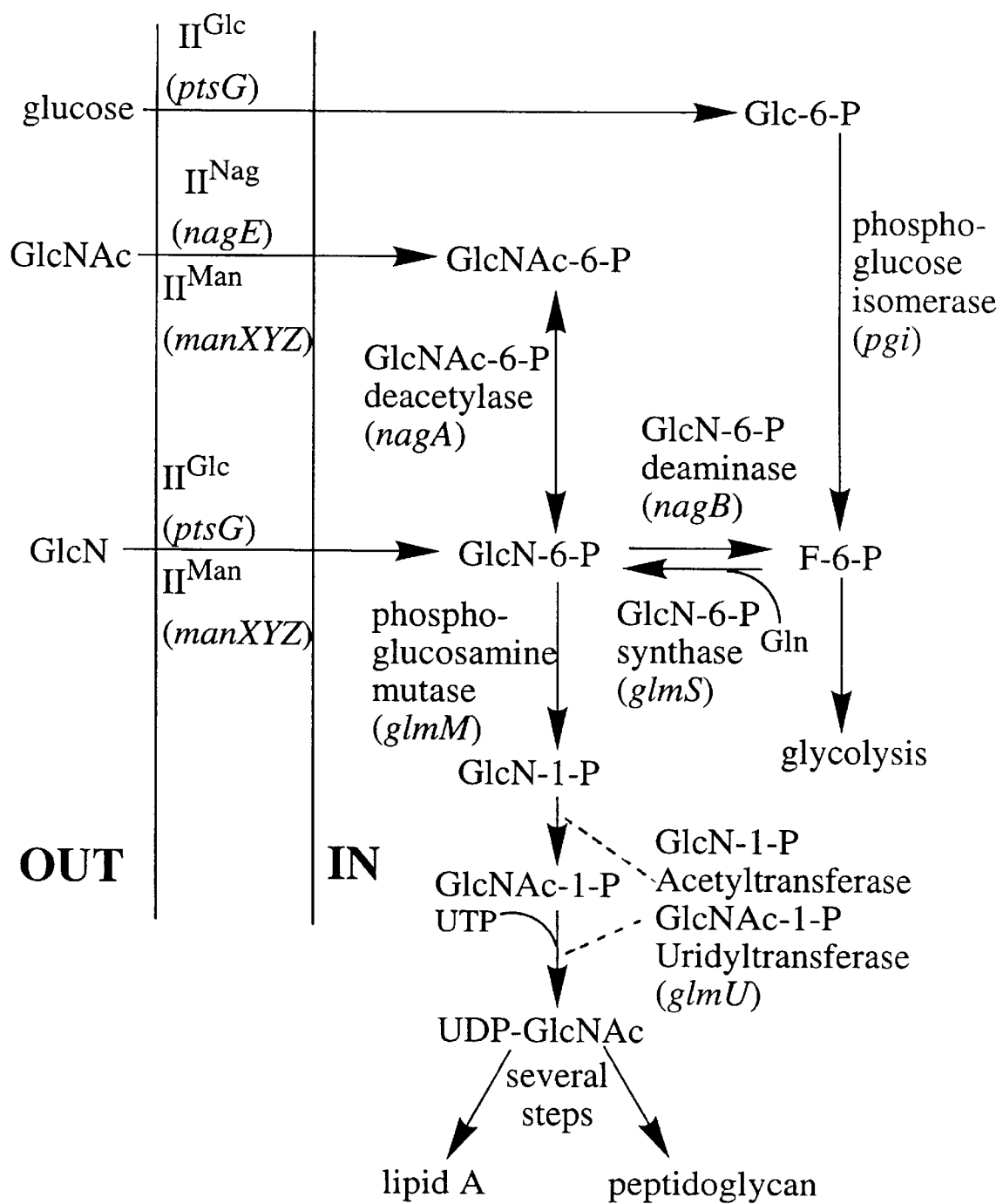
FIG. 1 is a schematic representation of the pathways for the biosynthesis and catabolism of glucosamine and N-acetyl-glucosamine and their phosphorylated derivatives in *Escherichia coli*.
Figure 2:
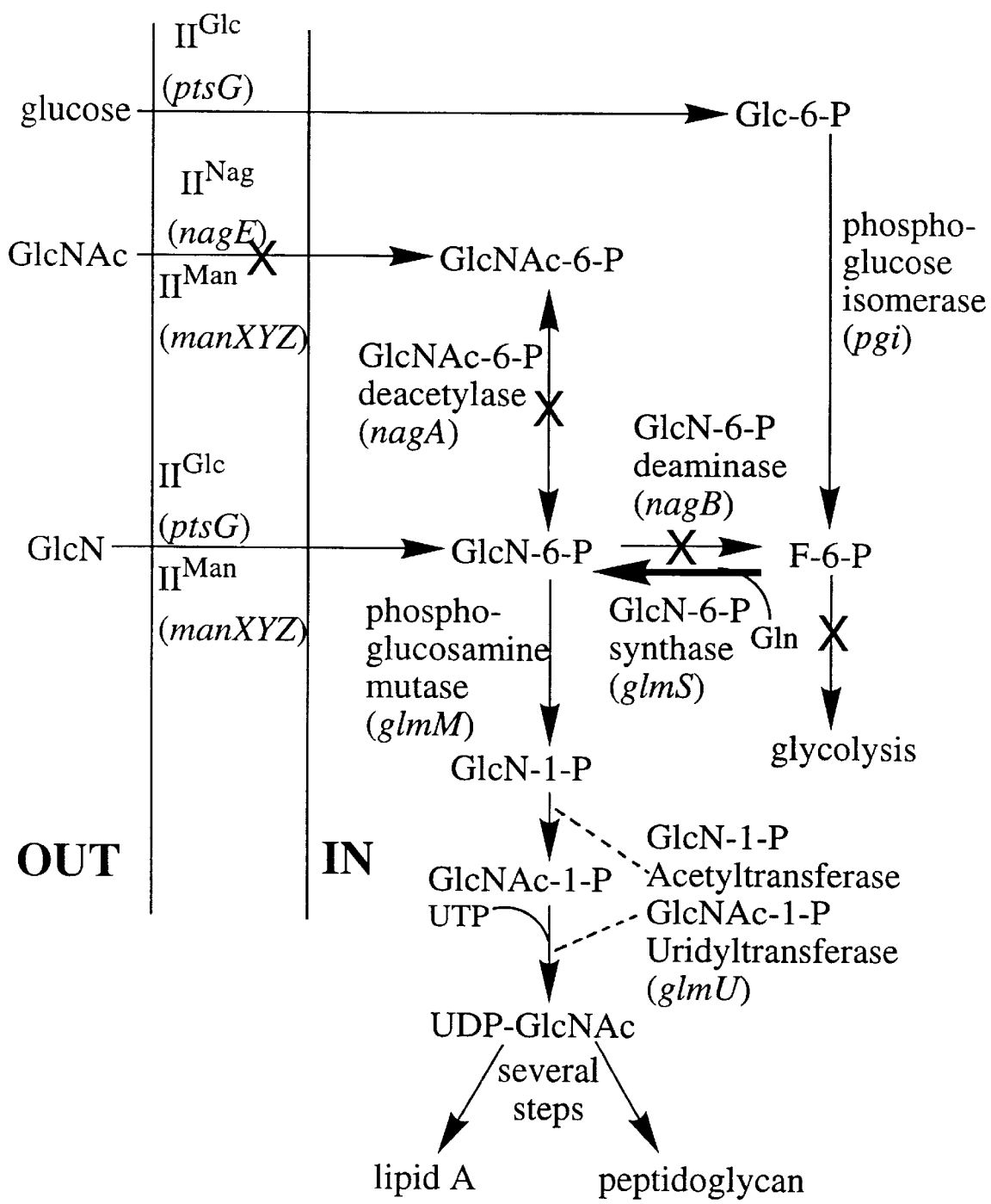
FIG. 2 is a schematic representation of the modifications to the pathways related to amino sugar metabolism for the overproduction of glucosamine in *Escherichia coli*.

The present invention relates to a biosynthetic method for producing glucosamine. Such a method includes fermentation of a genetically modified microorganism to produce glucosamine. The present invention also relates to genetically modified microorganisms, such as strains of *Escherichia coli*, useful for producing glucosamine. As used herein, the terms glucosamine and N-glucosamine can be used interchangeably. Similarly, the terms glucosamine-6-phosphate and N-glucosamine-6-phosphate can be used interchangeably. Glucosamine can also be abbreviated as GlcN and glucosamine-6-phosphate can also be abbreviated as GlcN-6-P.

The novel method of the present invention for production of glucosamine by fermentation is inexpensive and can produce a yield of glucosamine that exceeds the yield per cost of glucosamine produced by current hydrolysis methods. In addition, by using a genetically modified microorganism as described herein, the method of the present invention can be easily modified to adapt to particular problems or changing needs relative to the production of glucosamine.

The amino sugars, N-acetylglucosamine (GlcNAc) and glucosamine (GlcN), are fundamentally important molecules in microorganisms, because they are the precursors for the biosynthesis of major macromolecules, and in particular, glycoconjugates (i.e., macromolecules containing covalently bound oligosaccharide chains). For example, in *Escherichia coli*, N-acetylglucosamine and glucosamine are precursors for two macromolecules of the cell envelope, peptidoglycan and lipopolysaccharide. Mutations that block the biosynthesis of peptidoglycan or lipopolysaccharide are lethal, resulting in loss of integrity of the cell envelope and ultimately in cell lysis.

One embodiment of the present invention relates to a method to produce glucosamine by fermentation of a microorganism. This method includes the steps of (a) culturing in a fermentation medium a microorganism having a genetic modification in an amino sugar metabolic pathway which includes: a pathway for converting glucosamine-6-phosphate into another compound, a pathway for synthesizing glucosamine-6-phosphate, a pathway for transport of glucosamine or glucosamine-6-phosphate out of said microorganism, a pathway for transport of glucosamine into said microorganism, and a pathway which competes for substrates involved in the production of glucosamine-6-phosphate, to produce a product which can include intracellular glucosamine-6-phosphate and/or extracellular glucosamine from the microorganism; and (b) recovering the product by recovering intracellular glucosamine-6-phosphate from the microorganism and/or recovering extracellular glucosamine from the fermentation medium. The fermentation medium includes assimilable sources of carbon, nitrogen and phosphate.

Another embodiment of the present invention relates to a method to produce glucosamine by fermentation. Such method includes the steps of: (a) culturing in a fermentation medium comprising assimilable sources of carbon, nitrogen and phosphate, an *Escherichia coli* transformed with a recombinant nucleic acid molecule encoding glucosamine-6-phosphate synthase operatively linked to a transcription control sequence; and (b) recovering a product selected from the group of glucosamine-6-phosphate and glucosamine. The recombinant nucleic acid molecule increases expression of the glucosamine-6-phosphate synthase by the *Escherichia coli*. In a further embodiment, the recombinant nucleic acid molecule comprises a genetic modification which reduces glucosamine-6-phosphate product inhibition of the glucosamine-6-phosphate synthase. In yet another embodiment, the *Escherichia coli* has an additional genetic modification in at least one gene selected from the group of nagA, nagB, nagC, nagD, nagE, manXYZ, glmM, pfkB, pfkA, glmU, glmS, ptsG and/or a phosphatase gene.

To produce significantly high yields of glucosamine by the fermentation method of the present invention, a microorganism is genetically modified to enhance production of glucosamine. As used herein, a genetically modified microorganism, such as *Escherichia coli*, has a genome which is modified (i.e., mutated or changed) from its normal (i.e., wild-type or naturally occurring) form Genetic modification of a microorganism can be accomplished using classical strain development and/or molecular genetic techniques. Such techniques are generally disclosed, for example, in Sambrook et al., 1989, *Molecular Cloning: A Laboratory Manual*, Cold Spring Harbor Labs Press. The reference Sambrook et al., ibid., is incorporated by reference herein in its entirety. Additionally, techniques for genetic modification of a microorganism are described in detail in the Examples section. A genetically modified microorganism can include a natural genetic variant as well as a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism. According to the present invention, a genetically modified microorganism includes a microorganism that has been modified using recombinant technology. As used herein, genetic modifications which result in a decrease in gene expression, in the function of the gene, or in the function of the gene product (i.e., the protein encoded by the gene) can be referred to as inactivation (complete or partial), deletion, interruption, bloQkage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). Genetic modifications which result in an increase in gene expression or function can be referred to as amplification, overproduction, overexpression, activation, enhancement, addition, or up-regulation of a gene.

In one embodiment of the present invention, a genetic modification of a microorganism increases or decreases the action of a protein involved in an amino sugar metabolic pathway according to the present invention. Such a genetic modification includes any type of modification and specifically includes modifications made by recombinant technology and by classical mutagenesis. For example, in one embodiment, a microorganism of the present invention has a genetic modification that increases the action of glucosamine-6-phosphate synthase. It should be noted that reference to increasing the action (or activity) of glucosamine-6-phosphate synthase and other enzymes discussed herein refers to any genetic modification in the microorganism in question which results in increased functionality of the enzymes and includes higher activity of the enzymes (e.g., specific activity or in vivo enzymatic activity), reduced inhibition or degradation of the enzymes and overexpression of the enzymes. For example, gene copy number can be increased, expression levels can be increased by use of a promoter that gives higher levels of expression than that of the native promoter, or a gene can be altered by genetic engineering or classical mutagenesis to increase the action of an enzyme. Examples of nucleic acid molecules encoding glucosamine-6-phosphate synthase which have been genetically modified to increase the action of the glucosamine-6-phosphate synthase are described in the Examples section. Similarly, reference to decreasing the action of enzymes discussed herein refers to any genetic modification in the microorganism in question which results in decreased functionality of the enzymes and includes decreased activity of the enzymes (e.g., specific activity), increased inhibition or degradation of the enzymes and a reduction or elimination of expression of the enzymes. For example, the action of an enzyme of the present invention can be decreased by blocking or reducing the production of the enzyme, reducing enzyme activity, or inhibiting the activity of the enzyme. Blocking or reducing the production of an enzyme can include placing the gene encoding the enzyme under the control of a promoter that requires the presence of an inducing compound in the growth medium. By establishing conditions such that the inducer becomes depleted from the medium, the expression of the gene encoding the enzyme (and therefore, of enzyme synthesis) could be turned off. Blocking or reducing the activity of an enzyme could also include using an excision technology approach similar to that described in U.S. Pat. No. 4,743, 546, incorporated herein by reference. To use this approach, the gene encoding the enzyme of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

An amino sugar is an amino derivative of a saccharide (e.g., a saccharide having an amino group in place of a hydroxyl group). According to the present invention, an amino sugar metabolic pathway is any biochemical pathway involved in, or affecting, the biosynthesis, anabolism or catabolism of an amino sugar. As used herein, amino sugar metabolic pathways include pathways involved in the transport of amino sugars and their precursors into and out of a cell, and can also include biochemical pathways which compete for substrates involved in the biosynthesis or catabolism of an amino sugar. For example, the immediate precursor to one of the earliest formed amino sugars is fructose-6-phosphate (F-6-P), which, in a biochemical reaction with glutamine (Gln, the amino group donor), forms glucosamine-6-phosphate. Fructose-6-phosphate is also an intermediate in the glycolysis pathway. Therefore, the glycolytic pathway competes with the glucosamine-6-phosphate biosynthetic pathway by competing for a substrate, fructose-6-phosphate. In addition, glucosamine-6-phosphate can be converted to other amino sugars and form constituents in various macromolecules by a series of biochemical reactions. As such, the fructose-6-phosphate/ glucosamine-6-phosphate pathway, the fructose-6-phosphate glycolytic pathway, to the extent that it affects the biosynthesis of glucosamine-6-phosphate, and the glucosamine-6-phosphate/macromolecule biosynthesis pathway are all considered to be amino sugar metabolic pathways in the present invention.

In general, a microorganism having a genetically modified amino sugar metabolic pathway has at least one genetic modification, as discussed above, which results in a change in one or more amino sugar metabolic pathways as described above as compared to a wild-type microorganism cultured under the same conditions. Such a modification in an amino sugar metabolic pathway changes the ability of the microorganism to produce an amino sugar. According to the present invention, a genetically modified microorganism preferably has an enhanced ability to produce glucosamine compared to a wild-type microorganism cultured under the same conditions. An amino sugar metabolic pathway which affects the production of glucosamine can generally be categorized into at least one of the following kinds of pathways: (a) pathways for converting glucosamine-6-phosphate into other compounds, (b) pathways for synthesizing glucosamnine6-phosphate, (c) pathways for transporting glucosamine into a cell, (d) pathways for transporting glucosamine or glucosamine-6-phosphate out of a cell, and (e) pathways which compete for substrates involved in the production of glucosamine-6-phosphate.

A genetically modified microorganism useful in a method of the present invention typically has at least one modified gene involved in at least one amino sugar metabolic pathway which results in (a) reduced ability to convert glucosamine-6-phosphate into other compounds (i.e., inhibition of glucosamine-6-phosphate catabolic or anabolic pathways), (b) an enhanced ability to produce (i.e., synthesize) glucosamine-6-phosphate, (c) a reduced ability to transport glucosamine into the cell, (d) an enhanced ability to transport glucosamine-6-phosphate or glucosamnine out of the cell, and/or (e) a reduced ability to use substrates involved in the production of glucosamine-6-P for competing biochemical reactions.

It is to be understood that the present invention discloses a method comprising the use of a microorganism with an ability to produce comimercially useful amounts of glucosamine in a fermentation process (i.e., preferably an enhanced ability to produce glucosamine compared to a wild-type microorganism cultured under the same conditions). This method is achieved by the genetic modification of one or more genes encoding a protein involved in an amino sugar metabolic pathway which results in the production (expression) of a protein having an altered (e.g., increased or decreased) function as compared to the corresponding wild-type protein. Such an altered function enhances the ability of the genetically engineered microorganism to produce glucosamine. It will be appreciated by those of skill in the art that production of genetically modified microorganisms having a particular altered function as described elsewhere herein (e.g., an enhanced ability to produce glucosamine-6-phosphate) such as by the specific selection techniques described in the Examples, can produce many organisms meeting the given functional requirement, albeit by virtue of a variety of different genetic modifications. For example, different random nucleotide deletions and/or substitutions in a given nucleic acid sequence may all give rise to the same phenotypic result (e.g., decreased action of the protein encoded by the sequence). The present invention contemplates any such genetic modification which results in the production of a microorganism having the characteristics set forth herein.

For a variety of microorganism, many of the amino sugar metabolic pathways have been elucidated. In particular, pathways for the biosynthesis and catabolism of glucosamine and N-acetylglucosamine and their phosphorylated derivatives have been elucidated in *Escherichia coli*. These pathways include the multiple transport systems for the utilization of these amino sugars as carbon sources. Genes encoding the enzymes and proteins directly related to the transport, catabolism and biosynthesis of. amino sugars in *Escherichia coli* have been cloned and sequenced. In addition, mutant strains of *Escherichia coli* blocked in substantially every step of amino sugar metabolism have been isolated. The known pathways for amino sugar metabolism for *Escherichia coli* are illustrated in FIG. 1.

As will be discussed in detail below, even though many of the pathways and genes involved in the amino sugar metabolic pathways have been elucidated, until the present invention, it was not known which of the many possible genetic modifications would be necessary to generate a microorganism that can produce commercially significant amounts of glucosamine. Indeed, the present inventors are the first to design and engineer a glucosamine-producing microorganism that has glucosamine production capabilities that far exceed the glucosamine production capability of any known wild-type or mutant microorganism. The present inventors are also the first to appreciate that such a genetically modified microorganism is useful in a method to produce glucosamine for commercial use.

A microorganism to be used in the fermentation method of the present invention is preferably a bacterium or a yeast. More preferably, such a microorganism is a bacterium of the genus Escherichia. *Escherichia coil* is the most preferred microorganism to use in the fermentation method of the present invention. Particularly preferred strains of *Escherichia coli* include K-12, B and W, and most preferably, K-12. Although *Escherichlia coli* is most preferred, it is to be understood that any microorganism that produces glucosamine and can be genetically modified to enhance production of glucosamine can be used in the method of the present invention. A microorganism for use in the fermentation method of the present invention can also be referred to as a production organism.

The amino sugar metabolic pathways of the microorganism, *Escherichia coli*, will be addressed as specific embodiments of the present invention are described below. It will be appreciated that other microorganisms and in particular, other bacteria, have similar amino sugar metabolic pathways and genes and proteins having similar structure and function within such pathways. As such, the principles discussed below with regard to *Escherichia coli* are applicable to other microorganisms.

In one embodiment of the present invention, a genetically modified microorganism includes a microorganism which has an enhanced ability to synthesize glucosamine-6-phosphate. According to the present invention, "an enhanced ability to synthesize" a product refers to any enhancement, or up-regulation, in an amino sugar metabolic pathway related to the synthesis of the product such that the microorganism produces an increased amount of the product compared to the wild-type microorganism cultured under the same conditions. In one embodiment of the present invention, enhancement of the ability of a microorganism to synthesize glucosamine-6-phosphate is accomplished by amplification of the expression of the glucose-6-phosphate synthase gene, which in *Escherichia coli* is the glmS gene, the product of which is glucosamine-6-phosphate synthase. Glucosamine-6-phosphate synthase catalyzes the reaction in which fructose-6-phosphate and glutamine form glucosamine-6-phosphate and glutamic acid. Amplification of the expression of glucosamine-6-phosphate synthase can be accomplished in *Escherichia coli*, for example, by introduction of a recombinant nucleic acid molecule encoding the glmS gene.

Overexpression of glmS is crucial for the intracellular accumulation of glucosamine-6-phosphate and ultimately for production of glucosamine, since the level of glucosamine-6-phosphate synthase in the cell will control the redirection of carbon flow away from glycolysis and into glucosamine-6-phosphate synthesis. The glmS gene is located at 84 min on the *Escherichia coli* chromosome, and sequence analysis of this region of the chromosome reveals that glmS resides in an operon with the glmU gene, which encodes the bifunctional enzyme, glucosamine-1-phosphate acetyltransferase-N-acetylglucosamine-1-phosphate uridyltransferase. Glucosamine-1-phosphate acetyltransferase-N-acetylglucosamine-1-phosphate uridyltransferase functions within the amino sugar metabolic pathway in which glucosamine-6-phosphate is incorporated, through a series of biochemical reactions, into macromolecules. No obvious promoter sequence is detected upstream of glmS; transcription of the glmUS operon is initiated from two promoter sequences upstream of glmU. Thus, it is preferred that the glmS gene be cloned under control of an artificial promoter. The promoter can be any suitable promoter that will provide a level of glmS expression required to maintain a sufficient level of glucosaiaine-6-phosphate synthase in the production organism. Preferred promoters are constitutive (rather than inducible) promoters, since the need for addition of expensive inducers is therefore obviated. Such promoters include normally inducible promoter systems that have been made functionally constitutive or "leaky" by genetic modification, such as by using a weaker, mutant repressor gene. Particularly preferred promoters to be used with glmS are lac, $\lambda P_L$ and T7. The gene dosage (copy number) of glmS can be varied according to the requirements for maximum product formation. In one embodiment, the recombinant glmS gene is integrated into the *E. coli* chromosome.

Therefore, it is an embodiment of the present invention to provide a microorganism, such as *E. coli*, which is transformed with a recombinant nucleic acid molecule comprising a nucleic acid sequence encoding a glucosamine-6-phosphate synthase, which in *E. coli*, for example, is encoded by the glmS gene. Preferred recombinant nucleic acid molecules comprising such a nucleic acid sequence include recombinant nucleic acid molecules comprising a nucleic acid sequence which encodes a glucosamine-6-phosphate synthase comprising an amino acid sequence SEQ ID NO:16. Other preferred recombinant nucleic acid molecules of the present invention include nucleic acid molecules which comprise a nucleic acid sequence selected from the group of SEQ ID NO:13, SEQ ID NO:14 and/or SEQ ID NO:15. Particularly preferred recombinant nucleic acid molecules of the present invention include nucleic acid molecules comprising nucleic acid molecules nglmS-$28_{2184}$ and/or nglmS-$28_{1830}$. One recombinant molecule of the present invention, referred to herein as plasmid pKLN23-28, includes SEQ ID NOs:13, 14 and 15 and is particularly useful for expressing glucosamine-6-phosphate synthase in a microorganism. The above identified nucleic acid molecules represent nucleic acid molecules comprising wild-type (i.e., naturally occurring or endogenous) nucleic acid sequences encoding glucosamine-6-phosphate synthase proteins. Genetically modified nucleic acid molecules which include nucleic acid sequences encoding homologues (i.e., modified and/or mutated) glucosamine-6-phosphate synthase proteins are also encompassed by the present invention and are described in detail below.

The reported $K_m$'s of glucosamine-6-phosphate synthase from *Escherichia coli* are 2 mM and 0.4 mM for fructose-6-phosphate and glutamine, respectively. These are relatively high values (i.e., the affinity of the enzyme for its substrates is rather weak). It is therefore another embodiment of the present invention to provide a microorganism having a glucosamine-6-phosphate synthase with improved affinity for its substrates. A glucosamine-6-phosphate synthase with improved affinity for its substrates can be produced by any suitable method of genetic modification or protein engineering. For example, computer-based protein engineering can be used to design a glucosamine-6-phosphate synthase protein with greater stability and better affinity for its substrate. See for example, Maulik et al., 1997, *Molecular Biotechnology: Therapeutic Applications and Strategies*, Wiley-Liss, Inc., which is incorporated herein by reference in its entirety.

White (1968, Biochem. J., 106:847–858) first demonstrated that glucosamine-6-phosphate synthase was inhibited by glucosamine-6-phosphate. The present inventors determined that this inhibition was a key factor which limits glucosamine accumulation in glucosamine production strains of the present invention, which have been designed for commercial use. Therefore, it is yet another embodiment of the present invention to provide a microorganism having a glucosamine-6-phosphate synthase with reduced glucosamine-6-phosphate product feedback inhibition. A glucosamine-6-phosphate synthase with reduced product inhibition can be a mutated (i.e., genetically modified) glucosamine-6-phosphate synthase gene, for example, and can be produced by any suitable method of genetic modification. For example, a recombinant nucleic acid molecule encoding glucosamine-6-phosphate synthase can be modified by any method for inserting, deleting, and/or substituting nucleotides, such as by error-prone PCR. In this method, the gene is amplified under conditions that lead to a high frequency of misincorporation errors by the DNA polymerase used for the amplification. As a result, a high frequency of mutations are obtained in the PCR products. This method is described in detail in Example 5. The resulting glucosamine-6-phosphate synthase gene mutants can then be screened for reduced product inhibition by testing the mutant genes for the ability to confer increased glucosamine production onto a test microorganism, as compared to a microorganism carrying the non-mutated recombinant glucosamine-6-phosphate synthase nucleic acid molecule. It should be noted that decreased product inhibition of glucosamine-6-phosphate synthase typically results in a glucosamine-6-phosphate synthase with increased action, even when the specific activity of the enzyme is remains the same, or actually is decreased, relative to a naturally occurring glucogamine-6-phosphate enzyme. Therefore, it is an embodiment of the present invention to produce a genetically modified glucosamine-6-phosphate synthase with increased action and increased in vivo enzymatic activity, which has unmodified or even decreased specific activity as compared to a naturally occurring glucosamine-6-phosphate synthase. Also encompassed by the present invention are genetically modified glucosamine-6-phosphate synthases with increased specific activity.

Therefore, it is an embodiment of the present invention to provide a microorganism, such as *E. coli*, which is transformed with a genetically modified recombinant nucleic acid molecule comprising a nucleic acid sequence encoding a mutant, or homologue, glucosamine-6-phosphate synthase protein. Such glucosamine-6-phosphate synthase proteins can be referred to herein as glucosamine-6-phosphate synthase homologues. Protein homologues are described in detail below. Preferred recombinant nucleic acid molecules comprising such a nucleic acid sequence include recombinant nucleic acid molecules comprising a nucleic acid sequence which encodes a glucosamine-6-phosphate synthase comprising an amino acid sequence selected from the group of SEQ ID NO:19, SEQ ID NO:22, SEQ ID NO:25, SEQ ID NO:28 and/or SEQ ID NO:31. Other preferred recombinant nucleic acid molecules comprise a nucleic acid sequence selected from the group of SEQ ID NO:17, SEQ ID NO:18, SEQ ID NO:20, SEQ ID NO:21, SEQ ID NO:23, SEQ ID NO:24, SEQ ID NO:26, SEQ ID NO:27, SEQ ID NO:29 and/or SEQ ID NO:30. Particularly preferred genetically modified recombinant nucleic acid molecules useful in the present invention include nucleic acid molecules comprising nucleic acid molecules selected from the group of nglmS-$49_{2184}$, nglmS-$49_{1830}$, nglmS-$54_{2184}$, nglmS-$54_{1830}$, nglmS-$124_{2184}$, nglmS-$124_{1830}$, nglmS-$149_{2184}$, nglmS-$149_{1830}$, nglmS-$151_{2184}$ and nglmS-$151_{1830}$. Plasmids pKLN23-49, pKLN23-54, pKLN23-124, pKLN23-149 and pKLN23-151 are recombinant nucleic acid molecules of the present invention which are particularly useful for expressing glucosamine-6-phosphate synthase homologues in a microorganism.

An adequate intracellular supply of glutamine (Gln) is critical for the glucosamine-6-phosphate synthase reaction. Inspection of the synthetic and degradative pathways for glucosamine-6-phosphate reveals the presence of a potential futile cycle whereby continuous interconversion of fructose-6-phosphate and glucosamine-6-phosphate results in wasteful depletion of glutamine. In one embodiment of the present invention, the supply of glutamine can be increased either by genetic modification of the production organism to increase glutamine production in the cell, or by modifying the fermentation medium (i.e., adding glutamine to the fermentation medium), to ensure that the supply of glutamine will not limit the production of glucosamine-6-phosphate.

In another embodiment of the present invention, the potential futile cycling of fructose-6-phosphate and glucosamine-6-phosphate is addressed by inhibiting, or blocking, the reverse reaction in which glucosamine-6-phosphate is converted into fructose-6-phosphate. In this embodiment, a microorganism is genetically modified to have an inactivation or deletion of the gene which catalyzes this conversion, glucosamine-6-phosphate deaminase, which in *Escherichia coli* is the nagB gene. nagB is one of several nag genes which are part of the nag regulon. The nag genes involved in the degradation of glucosamine and N-acetyl-glucosamine exist as a regulon located at 15 min on the *Escherichia coli* chromosome. In another embodiment, the entire nag regulon is inactivated or deleted. The advantages of deleting the entire nag regulon are discussed in detail below.

As discussed above, overproduction of glucosamine-6-phosphate synthase results in diversion of fructose-6-phosphate synthesis to glucosamine-6-phosphate synthesis. However, many other enzymes can compete for the substrate, fructose-6-phosphate. Therefore, one embodiment of the present invention includes a microorganism in which these competitive side reactions are blocked. In a preferred embodiment, a microorganism having complete or partial inactivation of the gene encoding phosphofructokinase is provided. The second step in the glycolytic pathway is the conversion of fructose-6-phosphate to fructose-1,6-diphosphate by phosphofructokinase, which in *Escherichia coli* exists as two isozymes encoded by the pfkA and pfkB genes. Complete or partial inactivation of either the pfkA or pfkB genes slows the entry of fructose-6-phosphate into the glycolytic pathway and enhances the conversion of fructose-6-phosphate to glucosamine-6-phosphate. As used herein, inactivation of a gene can refer to any modification of a gene which results in a decrease in the activity (i.e., expression or function) of such a gene, including attenuation of activity or complete deletion of activity.

In a further embodiment of the present invention, a genetically modified microorganism has a decreased ability to convert glucosamine-6-phosphate into other compounds. Inactivation of glucosamine-6-phosphate deaminase, as described above, represents one such modification, however, glucosamine-6-phosphate serves as a substrate for other biochemical reactions. The first committed step in the pathway leading to production of macromolecules such as lipopolysaccharide and peptidoglycan in *Escherichia coli* is the conversion of glucosamine-6-phosphate to glucosamine-1-phosphate by phosphoglucosamine mutase, which in *Escherichia coli* is the product of the glmM gene. The involvement of this enzyme activity in the pathway of lipopolysaccharide and peptidoglycan biosynthesis was recently confirmed with the cloning of the glmM gene. Consequently, the regulation of glmM gene, and its cognate product, phosphoglucosamine mutase, has not been studied in detail. It has been shown, however, that the phosphoglucosamine mutase, like all other hexosephosphate mutase enzymes studied, is regulated by phosphorylation. This type of regulation at the enzyme level is typically exquisitely sensitive to levels of the pathway end products. Thus, carbon flow through phosphoglucosamine mutase can be self-regulating and may not be a problem as glucosamine-6-phosphate accumulates. Since the sequence of the glmM gene is known, however, it is a preferred embodiment of the present invention to provide a microorganism in which the gene encoding phosphoglucosamine mutase is interrupted or deleted. More preferably, the gene encoding phosphoglucosamine mutase is down-regulated, but not completely inactivated, by a mutation, so as not to completely block the biosynthesis of the critical cell envelope components.

Another pathway which results in the conversion of glucosamine-6-phosphate to another compound is catalyzed by the enzyme, N-acetylglucosamine-6-phosphate deacetylase. N-acetylglucosamine-6-phosphate deacetylase is capable of catalyzing the reverse reaction of converting glucosamine-6-phosphate (plus acetyl CoA) to N-acetyl-glucosamine-6-phosphate. This could result in futile cycling of glucosamine-6-phosphate and N-acetyl-glucosamine-6-phosphate and result in a product composed of a mixture of glucosamine and N-acetyl-glucosamine. Therefore, it is a further embodiment of the present invention to provide a genetically modified microorganism in which the gene encoding N-acetylglucosamine-6-phosphate deacetylase, which is the nagA gene in *Escherichia coli*, is inactivated.

It is a further embodiment of the present invention to inactivate the transport systems for glucosamine in a microorganism such that once the glucosamine is excreted by the cell it is not taken back up. This modification is helpful for avoiding a high intracellular level of glucosamine which could be toxic to the cells, and facilitates recovery of the product, since the product remains extracellular. In a preferred embodiment of the present invention, the transportation systems for glucosamine are inactivated to keep glucosamine outside of the microorganism once it is excreted by the microorganism. During growth of *Escherichia coli* on glucosamine as sole carbon source, glucosamine is transported into the cell by the PEP:mannose phosphotransferase (PTS) system, which is not only capable of transporting glucosamine into the cell, but is also induced by glucosamine. It is therefore an embodiment of the present invention to provide a microorganism lacking the ability to transport glucosamine into the cell. For example, a manXYZ mutant (i.e., an *Escherichia coli* lacking or having a mutation in the genes encoding EIIM,P/III$^{Man}$ of the PEP:mannose PTS) can not transport glucosamine into the cell by this mechanism. The PEP:glucose PTS of *Escherichia coli*, on the other hand, is capable of transporting both glucose and glucosamine into the cell, but glucosamine cannot induce this system. Thus, in order to grow a manXYZ muant on glucosamine, the cells must first be grown on glucose to induce expression of the (alternate) glucose transport systera and allow glucose (the preferred carbon source) to be transported into the cell. These induced cells are then capable of transporting glucosamine into the cell via the glucose transporter. A similar situation exists for transport of glucosamine by the PEP:fructose PTS, although in this case glucosamine transport by the enzyme II$^{Fru}$ is poor. Methods to inhibit these secondary glucosamine transport pathways are discussed below. It is yet another embodiment of the present invention to provide a microorganism having a decreased function in the PEP:glucose PTS (described above). Such a modification may be necessary to avoid "reabsorption of glucosamine from the culture medium. For example, a ptsG mutant (i.e., an *Escherichia coli* lacking or having a mutation in the genes encoding enzyme II$^{Glc}$ of the PEP:glucose PTS). Since such microorganisms will have reduced ability to grow using glucose as a carbon source, such organisms can be further genetically modified to take up glucose by a PEP:glucose PTS-independent mechanism. It is has been shown, for example, that mutant microorganisms can be selected which are defective in the PEP:glucose PTS and still have an ability to grow on glucose (Flores et al., 1996, *Nature Biotechnology* 14:620–623).

DNA sequencing of the nag regulon in *Escherichia coli* reveals that the nagE gene, encoding the N-acetylglucosamine-specific enzyme II$^{Nag}$ protein of the PEP:sugar phosphotransferase (PTS) system, which is involved in glucosamine transport into the cell, resides on one arm of the regulon and is transcribed divergently from the other nag genes (nagBACD) located on the other arm of the regulon. Therefore, another genetic modification that would result in decreased ability of an *Escherichia coli* to transport glucosamine into the cell is an inactivation or deletion of the nagE gene, or a gene encoding a similar enzyme in any microorganism used in a method of the present invention.

As discussed above, in one embodiment of the present invention, a genetically modified *Escherichia coli* microorganism useful in a method of the present invention has a deletion of the entire nag regulon. Deletion of the entire chromosomal nag regulon is preferred, because many genes which are deleterious to the production of glucosamine-6-phosphate are inactivated together. The genes, nagA, nagB and nagE, have been discussed in detail above. The nagC gene encodes a regulatory protein that acts as a repressor of the nag regulon as well as both an activator and repressor of the glmUS operon. The glm genes are discussed in detail above. The function of the nagD gene is not known, but is believed to be related to amino sugar metabolism as it resides within the nag regulon. Thus, in *Escherichia coli*, a complete deletion of the nag regulon avoids catabolism of the initial intracellular product (glucosamine-6-phosphate) in a strain of *Escherichia coli* designed to overproduce glucosamine. A preferred *Escherichia coli* mutant strain having a deletion of the nag regulon is an *Escherichia coli* having a ΔnagEBACD::tc deletion/insertion.

With regard to activation of the glmUS operon (a function of nagC), although activation of the glmS gene, encoding glucosagine-6-phosphate synthase, is desirable, an increase in the level of the glmU gene product, glucosamine-1-phosphate acetyltransferase-N-acetylglucosamine-1-phosphate uridyltransferase could be deleterious to accumulation of glucosamine-6-phosphate as it could lead to siphoning off of carbon flow toward cell envelope components. It is therefore an embodiment of the present invention to inactivate glucosamine-1-phosphate acetyltransferase-N-acetylglucosamine-1-phosphate uridyltransferase in a microorganism useful in a method of the present invention. In a microorganism in which the glmUS operon, or its equivalent, has been inactivated or deleted, it is a further embodiment of the present invention to genetically modify the microorganism by recombinantly producing the gene encoding glucosamine-6-phosphate synthase under control of an artificial promoter in the microorganism.

The initial intracellular product in the genetically modified microorganism described herein is glucosamine-6-phosphate. In many microorganisms, including Escherichia coli, glucosamine-6-phosphate is typically dephosphorylated to glucosamine prior to transport out of the cell. Nonetheless, it is yet another embodiment of the present invention to provide a microorganism which is genetically modified to have a suitable phosphatase activity for the conversion of glucosamine-6-phosphate to glucosamine. Such a phosphatase can include, but is not limited to, for example, alkaline phosphatase. In a preferred embodiment, such an Escherichia coli has an enhanced (i.e., increased) level of phosphatase activity (i.e., phosphatase action).

As noted above, in the method for production of glucosamine of the present invention, a microorganism having a genetically modified amino sugar metabolic pathway is cultured in a fermentation medium for production of glucosamine. An appropriate, or effective, fermentation medium refers to any medium in which a genetically modified microorganism of the present invention, when cultured, is capable of producing glucosamine. Such a medium is typically an aqueous medium comprising assimilable carbon, nitrogen and phosphate sources. Such a medium can also include appropriate salts, minerals, metals and other nutrients. One advantage of the genetic modifications to a microorganism described herein is that although such genetic modifications significantly alter the metabolism of amino sugars, they do not create any nutritional requirements for the production organism. Thus, a minimal-salts medium containing glucose as the sole carbon source is preferably used as the fermentation medium. The use of a minimal-salts-glucose medium for the glucosamine fermentation will also facilitate recovery and purification of the glucosamine product.

Microorganisms of the present invention can be cultured in conventional fermentation bioreactors. The microorganisms can be cultured by any fermentation process which includes, but is not limited to, batch, fed-batch, cell recycle, and continuous fermentation. Preferably, microorganisms of the present invention are grown by batch or fed-batch fermentation processes.

In one embodiment of the present invention, before inoculation, the fermentation medium is brought up to the desired temperature, typically from about 20° C. to about 40° C., preferably from about 25° C. to about 40° C., with temperatures of from about 28° C. to about 37° C., and in some embodiments, about 30° C. or about 37° C. being more preferred. The present inventors have discovered that glucosamine production in microorganisms of the present invention transfected with a nucleic acid molecule under control of the T7-lac promoter (see Examples section) continues after growth has ceased when the microorganisms are cultured at 30° C., while at 37° C., growth an glucosamine production occur in concert. Growth at 37° C. is slightly better than at 30° C., but glucosamine production at 30° C. is significantly better than at 37° C. It is noted that the optimum temperature for growth and glucosamine production by a microorganism of the present invention can vary according to a variety of factors. For example, the selection of a particular promoter for expression of a recombinant nucleic acid molecule in the microorganism can affect the optimum culture temperature. One of ordinary skill in the art can readily determine the optimum growth and glucosamine production temperature for any microorganism of the present invention using standard techniques, such as those described in the Examples section for one microorganism of the present invention.

The medium is inoculated with an actively growing culture of the genetically modified microorganism in an amount sufficient to produce, after a reasonable growth period, a high cell density. The cells are grown to a cell density of at least about 10 g/l, preferably between about 10 g/l and about 40 g/l, and more preferably at least about 40 g/l. This process typically requires about 10–60 hours.

Sufficient oxygen must be added to the medium during the course of the fermentation. to maintain cell growth during the initial cell growth and to maintain metabolism and glucosamine production. Oxygen is conveniently provided by agitation and aeration of the medium. Conventional methods, such as stirring or shaking, may be used to agitate and aerate the medium. Preferably the oxygen concentration in the medium is greater than about 15% of the saturation value (i.e., the solubility of oxygen in the medium at atMspheric pressure and about 30–40° C.) and more preferably greater than about 20% of the saturation value, although excursions to lower concentrations may occur if fermentation is not adversely affected. The oxygen concentration of the medium can be monitored by conventional methods, such as with an oxygen electrode. Other sources of oxygen, such as undiluted oxygen gas and oxygen gas diluted with inert gas other than nitrogen, can be used.

Since the production of glucosamine by fermentation is preferably based on using glucose as the sole carbon source, in a preferred embodiment, in Escherichia coli, the PEP:glucose PTS will be induced. Accordingly, even in the absence of a functional EIIM,P/III$^{Man}$ of the PEP:mannose PTS (e.g., in an Escherichia coil having a manXYZ mutation), the product, glucosamine, will still be taken up by the cells via the induced glucose transport system. In the presence of excess glucose, however, uptake of glucosamine is severely repressed. Thus, it is one embodiment of the present invention to prevent uptake of the glucosamine product by maintaining an excess of glucose in the fermentation bioreactor. Asused herein, "an: excess" of glucose refers to an amount of glucose above that which is required to maintain the growth of the microorganism under normal conditions, such as the culturing conditions described above. Preferably, the glucose concentration is maintained at a concentration of from about 0.5% to about 5% weight/volume of the fermentation medium. In another embodiment, the glucose concentration is maintained at a concentration of from about 5 g/L to about 50 g/L of the fermentation medium, and even more preferably, from about 5 g/L to about 20 g/L of the fermentation medium. In one embodiment, the glucose concentration of the fermentation medium is monitored by any suitable method (e.g., by using glucose test strips), and when the glucose concentration is at or near depletion, additional glucose can be added to the medium. In another embodiment, the glucose concentration is maintained by semi-continuous or continuous feeding of the fermentation medium. The parameters disclosed herein for glucose can be applied to any carbon source used in the fermentation medium of the present invention. It is further understood that the carbon source can be allowed to reach undetectable levels for any appropriate amount of time during the fermentation if it enhances the glucosamine production process.

It is a further embodiment of the present invention to supplement and/or control other components and parameters of the fermentation medium, as necessary to maintain and/or enhance the production of glucosamine by a production organism. For example, in one embodiment, the fermentation medium includes ammonium sulfate, and the ammonium sulfate concentration in the culture medium is supplemented by the addition of excess ammonium sulfate. Preferably, the amount of ammonium sulfate is maintained at a level of from about 0.1% to about 1% (weight/volume) in the fermentation medium, and preferably, at about 0.5%. In yet another embodiment, the pH of the fermentation medium is monitored for fluctuations in pH. In the fermentation method of the present invention, the pH is preferably maintained at a pH of from about pH 6.0 to about pH 8.0, and more preferably, at about pH 7.0. In the method of the present invention, if the starting pH of the e fermentation medium is pH 7.0, the pH of the fermentation medium is monitored for significant variations from pH 7.0, and is adjusted accordingly, for example, by the addition of sodium hydroxide.

A further embodiment of the present invention is to redirect carbon flux from acetate production to the production of less toxic byproducts. By such methods, problems of toxicity associated with an excess of glucose in the fermentation medium can be avoided. Methods to redirect carbon flux from acetate production are known in the art.

In a batch fermentation process of the present invention, fermentation is continued until the formation of glucosamine, as evidenced by the accumulation of extracellular glucosamine, essentially ceases. The total fermentation time is typically from about 40 to about 60 hours, and more preferably, about 48 hours. In a continuous fermentation process, glucosamine can be removed from the bioreactor as it accumulates in the medium. The method of the present invention results in production of a product which can include intracellular or extracellular glucosamine-6-phosphate and intracellular or extracellular glucosamine.

The method of the present invention further includes recovering the product, which can be intracellular glucosamine-6-phosphate or extracellular glucosamine. The phrase "recovering glucosamine" refers simply to collecting the product from the fermentation bioreactor and need not imply additional steps of separation or purification. For example, the step of recovering can refer to removing the entire culture (i.e., the microorganism and the fermentation medium) from the bioreactor, removing the fermentation medium containing extracellular glucosamine from the bioreactor, fee and/or removing the microorganism containing intracellular glucosamine-6-phosphate from the bioreactor. These steps can be followed by further purification steps. Glucosamine is preferably recovered in substantially pure form. As used herein, "substantially pure" refers to a purity that allows for the effective use of the glucosamine as a nutriceutical compound for commercial sale. In one embodiment, the glucosamine product is preferably separated from the production organism and other fermentation medium constituents. Methods to accomplish such separation are described below.

Preferably, by the method of the present invention, at least about 1 g/L of product (i.e., glucosamine and/or glucosamine-6-phosphate) are recovered from the microorganism and/or fermentation medium. More preferably, by the method of the present invention, at least about 5 g/L, and even more preferably, at least about 10 g/L, and even more preferably, at least about 20 g/L and even more preferably, at least about 50 g/L of product are recovered. In one embodiment, glucosamine product is recovered in an amount from about 1 g/L to about 50 g/L.

Typically, most of the glucosamine produced in the present process is extracellular. The microorganism can be removed from the fermentation medium by conventional methods, such as by filtration or centrifugation. In one embodiment, the step of recovering the product includes the purification of glucosamine from the fermentation medium. Glucosamine can be recovered from the cell-free fermentation medium by conventional methods, such as chromatography, extraction, crystallization (e.g., evaporative crystallization), membrane separation, reverse osmosis and distillation. In a preferred embodiment, glucosamine is recovered from the cell-free fermentation medium by crystallization. In another embodiment, the step of recovering the product includes the step of concentrating the extracellular glucosamine.

In one embodiment, glucosamine-6-phosphate accumulates intracellularly, the step of recovering the product includes isolating glucosamine-6-phosphate from the microorganism. For example, the product can be recovered by lysing the microorganism cells by a method which does not degrade the glucosamine product, centrifuging the lysate to remove insoluble cellular debris, and then recovering the glucosamine and/or glucosamine-6-phosphate product by a conventional method as described above.

The initial intracellular product in the genetically modified microorganism described herein is glucosamine-6-phosphate. It is generally accepted that phosphorylated intermediates are dephosphorylated during export from the microorganism, most likely due to the presence of alkaline phosphatase in the periplasmic space of the microorganism. In one embodiment of the present invention, glucosamine-6-phosphate is dephosphorylated before or during export from the cell by naturally occurring phosphatases in order to facilitate the production of the desired product, glucosamine. In this embodiment, the need for amplification of a recombinantly provided phosphatase activity in the cell or treatment of the fermentation medium with a phosphatase is obviated. In another embodiment, the level of phosphatase in the production organism is increased by a method including, but not limited to, genetic modification of an endogenous phosphatase gene or by recombinant modification of the microorganism to express a phosphatase gene. In yet another embodiment, the recovered fermentation medium is treated with a phosphatase after glucosamine-6-phosphate is released into the medium, such as when cells are lysed as described above.

As noted above, the process of the present invention produces significant amounts of extracellular glucosamine. In particular, the process produces extracellular glucosamine such that greater than about 50% of total glucosamine is extracellular, more preferably greater than about 75% of total glucosamine is extracellular, and most preferably greater than about 90% of total glucosamine is extracellular. By the method of the present invention, production of an extracellular glucosamine concentration can be achieved which is greater than about 1 g/l, more preferably greater than about 5 g/l, even preferably greater than about 10 g/l, and even more preferably greater than about 20 g/L and even more preferably greater than about 50 g/l.

One embodiment of the present invention relates to a method to produce glucosamine by fermentation which includes the steps of (a) culturing an *Escherichia coli* having a genetically modified amino sugar metabolic pathway in a fermentation medium comprising assimilable sources of carbon, nitrogen and phosphate to produce a product, and (b) recovering the product. The product includes intracellular glucosamine-6-phosphate which is recovered from the *Escherichia coli* and/or extracellular glucosamine which is recovered from the fermentation medium.

One embodiment of the present invention relates to a microorganism for producing glucosamine by a biosynthetic process. The microorganism is transformed with a recombinant nucleic acid molecule encoding glucosamine-6-phosphate synthase operatively linked to a transcription control sequence. The recombinant nucleic acid molecule has a genetic modification which reduces glucosamine-6-phosphate product inhibition of the glucosamine-6-phosphate synthase. Expression of the recombinant nucleic acid molecule increases expression of the glucosamine-6-phosphate synthase by the microorganism. In a preferred embodiment, the recombinant nucleic acid molecule is integrated into the genome of the microorganism. In a further embodiment, the microorganism has at least one additional genetic modification in a gene encoding a protein selected from the group of N-acetylglucosamine-6-phosphate deacetylase, glucosamine-6-phosphate deaminase, N-acetyl-glucosamine-specific enzyme $II^{Nag}$, phosphoglucosamine mutase, glucosamine-1-phosphate acetyltransferase-N-acetylglucosamine-1-phosphate uridyltransferase, phosphofructokinase, Enzyme $II^{Glc}$ of the PEP:glucose PTS, EIIM,P/$III^{Man}$ of the PEP:mannose PTS, and/or a phosphatase. The genetic modification decreases the action of the protein, except in the case of the phosphatase, in which the action of the phosphatase is preferably increased. In another preferred embodiment, the microorganism has a modification in genes encoding N-acetylglucosamine-6-phosphate deacetylase, glucosamine-6-phosphate deaminase and N-acetyl-glucosamine-specific enzyme $II^{Nag}$, wherein the genetic modification decreases action of the protein. In one embodiment, the genetic modification is a deletion of at least a portion of the genes.

In a preferred embodiment, the genetically modified microorganism is a bacterium or a yeast, and more preferably, a bacterium of the genus Escherichia, and even more preferably, *Escherichia coli*. A genetically modified *Escherichia coli* preferably has a modification in a gene which includes, but is not limited to, nagA, nagB, nagC, nagD, nagE, manXYZ, glmM, pfkB pfkA, glmU, glmS, ptsG or a phosphatase gene. In another embodiment, such a genetically modified *Escherichia coli* has a deletion of nag regulon genes, and in yet another embodiment, a deletion of nag regulon genes and a genetic modification in manXYZ genes such that the proteins encoded by the manXYZ genes have decreased action.

Yet another embodiment of the present invention relates to a microorganism for producing glucosamine by a biosynthetic process which has a recombinant nucleic acid molecule encoding glucosamine-6-phosphate synthase operatively linked to a transcription control sequence; and at least one genetic modification in a gene encoding a protein selected from the group of N-acetylglucosamine-6-phosphate deacetylase, glucosamine-6-phosphate deaminase, N-acetyl-glucosamine-specific enzyme $II^{Nag}$, phosphoglucosamine mutase, glucosamine-1-phosphate acetyltransferase-N-acetylglucosamine-1-phosphate uridyltransferase, phosphofructokinase, Enzyme $II^{Glc}$ of the PEP:glucose PTS, and/or EIIM,P/$III^{Man}$ of the PEP:mannose PTS. The genetic modification decreases action of said protein and expression of the recombinant nucleic acid molecule increases expression of the glucosamine-6-phosphate synthase by the microorganism. In another embodiment, the microorganism has at least one genetic modification in a phosphatase gene, such that the phosphatase encoded by such gene has increased action. In a preferred embodiment, the recombinant nucleic acid, molecule is integrated into the genome of the microorganism.

Another embodiment of the present invention relates to any of the above-described microorganisms which produces at least about 1 g/L of glucosamine when cultured for about 24 hours at 37° C. to a cell density of at least about 8 g/L by dry cell weight, in a pH 7.0 fermentation medium comprising: 14 g/L $K_2HPO_4$, 16 g/L $KH_2PO_4$, 1 g/L $Na_3Citrate.2H_2O$, 5 g/L $(NH_4)_2SO_4$, 20 g/L glucose, 10 mM $MgSO_4$, 1 mM $CaCl_2$, and 1 mM IPTG.

A more preferred embodiment of the present invention relates to any of the above-described microorganisms which produces at least about 1 g/L of glucosamine when cultured for about 10 to about 60 hours at from about 28° C. to about 37° C. to a cell density of at least about 8 g/L by dry cell weight, in a pH 7.0 fermentation medium comprising: 14 g/L $K_2HPO_4$, 16 g/L $KH_2PO_4$, 1 g/L $Na_3Citrate.2H_2O$, 5 g/L $(NH_4)_2SO_4$, 20 g/L glucose, 10 mM $MgSO_4$, 1 mM $CaCl_2$, and from about 0.2 mM to about 1 mM IPTG. In a preferred embodiment, the amount of IPTG is about 0.2 mM.

Yet another embodiment of the present invention relates to any of the above-described genetically modified microorganisms which produce at least about 1 g/L, and preferably at least about 5 g/L, and more preferably, at least about 10 g/L, and even more preferably, at least about 20 g/L, and even more preferably, at least about 50 g/L of glucosamine and/or glucosamine-6-phosphate when cultured under the culture conditions as described herein. Another embodiment of the present invention relates to any of the above-described genetically modified microorganisms which produce at least about 2-fold more glucosamine and/or glucosamine-6-phosphate, and preferably at least about 5-fold, and more preferably at least about 10-fold, and more preferably at least about 25-fold, and more preferably at least about 50-fold, and even more preferably at least about 100-fold, and even more preferably, at least about 200-fold more glucosamine and/or glucosamine-6-phosphate synthase than a wild-type (i.e., non-modified, naturally occurring) microorganism cultured under the same conditions as the genetically modified microorganism.

A number of specific microorganisms are identified in the Examples section. Additional embodiments of the present invention include these microorganisms and microorganisms having the identifying characteristics of the microorganisms specifically identified in the Examples. Such microorganisms are preferably yeast or bacteria, more preferably, are bacteria, and most preferably are *E. coli*. Such identifying characteristics can include any or all genotype and/or phenotypic characteristics of the microorganisms in the Examples, including their abilities to produce glucosamine.

Preferred microorganisms of the present invention include strains of *Escherichia coli* which have been transformed with a recombinant nucleic acid molecule encoding glucosamine- 6-phosphate synthase. Preferably, such a nucleic acid molecule is integrated into the genome of the microorganism. A particularly preferred microorganism is *Escherichia coli* strain 2123-12. Strain 2123-12 has integrated into its genome a recombinant nucleic acid molecule comprising a nucleic acid sequence SEQ ID NO:15, which represents the coding region of a wild-type (i.e., normal, unmodified, or naturally occurring) glucosamine-6-phosphate synthase enzyme having amino acid sequence SEQ ID NO:16. Particularly preferred microorganisms of the present invention have been transformed with a nucleic acid molecule comprising a nucleic acid sequence encoding a glucosamine-6-phosphate synthase that has been genetically modified such that the synthase has increased action (described above). Most preferably, such genetic modification enhances the ability of the microorganism to produce glucosamine as compared to a microorganism which has not been transformed with such a nucleic acid molecule. Particularly preferred genetically modified microorganisms of the present invention are described in the Examples section, and include E. coli strains 2123-49, 2123-54, 2123-124, 2123-149 and 2123-151.

Development of a microorganism with enhanced ability to produce glucosamine by genetic modification can be accomplished using both classical strain development and molecular genetic techniques. In general, the strategy for creating a microorganism with enhanced glucosamine production is to (1) inactivate or delete at least one, and preferably more than one of the amino sugar metabolic pathways in which production of glucosamine-6-phosphate is negatively affected (e.g., inhibited), and (2) amplify at least one, and preferably more than one of the amino sugar metabolic pathways in which glucosamine-6-phosphate production is enhanced. As such, genetically modified microorganisms of the present invention have a (a) reduced ability to convert glucosamine-6-phosphate into other compounds (i.e., inhibition of glucosamine-6-phosphate catabolic or anabolic pathways), (b) an enhanced ability to produce (i.e., synthesize) glucosamine-6-phosphate, (c) a reduced ability to transport glucosamine into the cell, (d) an enhanced ability to transport glucosamine-6-phosphate or glucosamine out of the cell, and/or (e) a reduced ability to use substrates involved in the production of glucosamine-6-P for competing biochemical reactions.

As previously discussed herein, in one embodiment, a genetically modified microorganism can be a microorganism in which nucleic acid molecules have been deleted, inserted or modified, such ag by insertion, deletion, substitution, and/or inversion of nucleotides, in such a manner that such modifications provide the desired effect within the microorganism. Such genetic modifications can, in some embodiments, be within the coding region for a protein encoded by the nucleic acid molecule which results in amino acid modifications such as insertions, deletions, substitutions in the amino acid sequence of the protein which provide the desired effect within the mincroorganisms. A genetically modified microorganism can be modified by recombinant technology, such as by introduction of an isolated nucleic acid molecule into a microorganism. For example, a genetically modified microorganism can be transfected with a recombinant nucleic acid molecule encoding a protein of interest, such as a protein for which increased expression is desired. The transfected nucleic acid molecule can remain extrachromosomal or can integrate into one or more sites within a chromosome of the transfected (i.e., recombinant) host cell in such a manner that its ability to be expressed is retained Preferably, once a host cell of the present invention is transfected with a nucleic acid molecule, the nucleic acid molecule is integrated into the host cell genome. A significant advantage of integration is that the nucleic acid molecule is stably maintained in the cell. In a preferred embodiment, the integrated nucleic acid molecule is operatively linked to a transcription control sequence (described below) which can be induced to control expression of the nucleic acid molecule.

A nucleic acid molecule can be integrated into the genome of the host cell either by random or targeted integration. Such methods of integration are known in the art. For example, as described in detail in Example 2, E. coli strain ATCC 47002 (Table 1) contains mutations that confer upon it an inability to maintain plasmid which contain a ColE1 origin of replication. When such plasmids are transferred to this strain, selection for genetic markers contained on the plasmid results in integration of the plasmid into the chromosome. This strain can be transformed, for example, with plasmids containing the gene of interest and a selectable marker flanked by the 5'- and 3'-termini of the E. coli lacZ gene. The lacZ sequences target the incoming DNA to the lacZ gene contained in the chromosome. Integration at the lacZ locus replaces the intact lacZ gene, which encodes the enzyme β-galactosidase, with a partial lacZ gene interrupted by the gene of interest. Successful integrants can be selected for β-galactosidase negativity. A genetically modified microorganism can also be produced by introducing nucleic acid molecules into a recipient cell genome by a method such as by using a transducing bacteriophage. The use of recombinant technology and transducing bacteriophage technology to produce several different genetically modified microorganism of the present invention is known in the art and is described in detail in the Examples section. According to the present invention, a gene, for example the pstg gene, includes all nucleic acid sequences related to a natural pstG gene such as regulatory regions that control production of the pstG protein (Enzyme $II^{Glc}$ of the PEP:glucose PTS) encoded by that gene (such as, but not limited to, transcription, translation or post-translation control regions) as well as the coding region itself. In another embodiment, a gene, for example the pstG gene, can be an allelic variant (i.e., a naturally occurring allelic variant) that includes a similar but not identical sequence to the nucleic acid sequence encoding a given pstG gene. An allelic variant of a pstG gene which has a given nucleic acid sequence is a gene that occurs at essentially the same locus (or loci) in the genome as the gene having the given nucleic acid sequence, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given microorganism, such as an E. coli, and/or among a group of two or more microorganisms.

Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a gene involved in an amino sugar metabolic pathway. In addition, the phrase "recombinant molecule" primarily refers to a nucleic acid molecule operatively linked to a transcription control sequence, but can be used interchangeably with the phrase "nucleic acid mol-molecule" which is isolated and expressed in a host cell.

Knowing the nucleic acid sequences of certain nucleic acid molecules of the present invention, and particularly Escherichia coli nucleic acid molecules, allows one skilled in the art to, for example, (a) make copies of those nucleic acid molecules and/or (b) obtain nucleic acid molecules including at least a portion of such nucleic acid molecules (e.g., nucleic acid molecules including full-length genes, full-length coding regions, regulatory control sequences, truncated coding regions). Such nucleic acid molecules can be obtained in a variety of ways including traditional cloning techniques using oligonucleotide probes of to screen appropriate libraries or DNA and PCR amplification of appropriate libraries or DNA using oligonucleotide primers. Preferred libraries to screen or from which to amplify nucleic acid molecule include bacterial and yeast genomic DNA libraries, and in particular, *Escherichia coli* genomic DNA libraries. Techniques to clone and amplify genes are disclosed, for example, in Sambrook et al., ibid.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA. There is no limit, other than a practical limit, on the maximal size of a nucleic acid molecule in that the nucleic acid molecule can include a portion of a gene, an entire gene, or multiple genes, or portions thereof.

An isolated nucleic acid molecule of the present invention can be obtained from its natural source either as an entire (i.e., complete) gene or a portion thereof capable of forming a stable hybrid with that gene. An isolated nucleic acid molecule can also be, produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect within the microorganism.

A nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene. Examples of such techniques are described in detail in the Examples section.

In one embodiment of the present invention, a nucleic acid homologue of a nucleic acid molecule of the present invention preferably comprises a genetic modification which results in a modification of the action of the protein encoded by the nucleic acid homologue. For example, in one embodiment of the present invention, a genetically modified recombinant nucleic acid molecule is provided which comprises a nucleic acid sequence encoding a glucosamine-6-phosphate synthase protein homologue, wherein the genetic modification increases the action of the glucosamine-6-phosphate synthase homologue, preferably as compared to a recombinant nucleic acid molecule encoding a naturally occurring glucosamine-6-phosphate synthase in the absence of such genetic modification. Such a genetic modification can increase the action of the glucosamine-6-phosphate synthase, for example, by encoding a glucosamine-6-phosphate synthase having reduced glucosamine-6-phosphate product inhibition and/or increased specific activity. Such recombinant nucleic acid molecules having genetic modifications are referred to herein as nucleic acid homologues of wild-type nucleic acid molecules encoding glucosamine-6-phosphate synthase. According to the present invention, proteins laving modifications as a result of genetic modifications in the nucleic acid molecules encoding the proteins are referred to herein as protein homologues, or homologues of the given protein.

Accordingly, a glucosamine-6-phosphate synthase protein, for example, which has glucosamine-6-phosphate synthase activity and is useful in the present invention, can be a full-length glucosamine-6-phosphate synthase protein, an enzymatically active portion of a full-length glucosamine-6-phosphate synthase protein, or any homologue of such proteins, such as a glucosamine-6-phosphate synthase protein having at least one or a few amino acid modifications in which amino acid residues have been deleted (e.g., a truncated version of the protein, such as a peptide), inserted, inverted, substituted and/or derivatized (e.g., by glycosylation, phosphorylation, acetylation, myristoylation, prenylation, palmitation, amidation and/or addition of glycosylphosphatidyl inositol).

A protein homologue of any of the proteins within the amino sugar metabolic pathways ac described in the present invention is a protein having an amino acid sequence that is sufficiently similar to a natural protein amino acid sequence (i.e., naturally occurring, unmodified, or wild-type) that a nucleic acid sequence encoding the homologue is capable of hybridizing under stringent conditions to (i.e., with) a nucleic acid molecule encoding the natural protein (i.e., to the complement of the nucleic acid grand encoding the natural protein amino acid sequence). A nucleic acid sequence complement of any nucleic acid sequence of the present invention refers to the nucleic acid sequence of the nucleic acid strand that is complementary to (i.e., can form a double helix with the entire molecule) the strand for which the sequence is cited. It is to be noted that a double-stranded nucleic acid molecule of the present invention for which a nucleic acid sequence has been determined for one strand that is represented by a SEQ ID NO also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art. The minimal size of a protein homologue of the present invention is a size sufficient to be encoded by a nucleic acid molecule capable of forming a stable hybrid with the complementary sequence of a nucleic acid molecule encoding the corresponding natural protein. Additionally, the minimal size of a protein homologue of the present invention is a size sufficient to have glucosamine-6-phosphate synthase action (e.g., a catalytically or enzymatically active portion), and preferably, increased glucosamine-6-phosphate synthase action. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). There is no limit, other than a practical limit, on the maximal size of such a nucleic acid molecule in that the nucleic acid molecule can include a portion of a gene, an entire gene, or multiple genes, or portions thereof. Similarly, the minimal size of a protein homologue of the present invention is from about 4 to about 6 amino acids in length, with preferred sizes depending on whether a full-length, multivalent (i.e., fusion protein having more than one domain each of which has a function), or functional portions of such proteins are desired.

As used herein, stringent hybridization conditions refer to standard hybridization conditions under which nucleic acid molecules are used to identify similar nucleic acid molecules, Such standard conditions are disclosed, for example, in Sambrook et al., Molecular Cloning: A Laboratory Manual, Cold Spring Harbor Labs Press, 1989. Sambrook et al., ibid., is incorporated by reference herein in its entirety (see specifically, pages 9.31–9.62, 11.7 and 11.45–11.61). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267–284; Meinkoth et al., ibid., is incorporated by reference herein in its entirety.

More particularly, stringent hybridization conditions, as referred to herein, refer to conditions which permit isolation of nucleic acid molecules having at least about 70% nucleic acid sequence identity with the nucleic acid molecule being used to probe in the hybridization reaction, more particularly at least about 75%, and most particularly at least about 80%. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 0.1×SSC (0.157 M $Na^+$) at a temperature of between about 20° C. and about 35° C., more preferably, between about 28° C. and about 40° C., and even more preferably, between about 35° C. and about 45° C. In particular embodiments, stringent hybridization conditions for DNA:RNA hybrids include hybridization at an ionic strength of 0.1×SSC (0.157 M $Na^+$) at a temperature of between about 30° C. and about 45° C., more preferably, between about 38° C. and about 50° C., and even more preferably, between about 45° C. and about 55° C. These values are based on calculations of a melting temperature for molecules larger than about 100 nucleotides, 0% formamide and a G+C content of about 50%. Alternatively, $T_m$ can be calculated empirically as set forth in Sambrook et al., supra, pages 11.55 to 11.57.

Protein homologues of proteins involved in an amino sugar metabolic pathway according to the present invention can be the result of natural allelic variation or natural mutation. Protein homologues of the present invention can also be produced using techniques known in the art including, but not limited to, direct modifications to the protein or modifications to the gene encoding the protein using, for example, classic or recombinant DNA techniques to effect random or targeted mutagenesis, as discussed above.

In one embodiment of the present invention, a genetic modification in a recombinant nucleic acid molecule of the present invention which encodes a glucosamine-6-phosphate synthase results in at least one amino acid modification (i.e., modification in the amino acid sequence of the encoded protein) selected from the group of an addition, substitution, deletion, and/or derivatization of an amino acid residue of the glucosamine-6-phosphate synthase. Such a modification in the amino acid sequence of the encoded protein can be determined as compared to a wild-type, or naturally occurring glucosamine-6-phosphate synthase, such as a glucosamine-6-phosphate synthase having an amino acid sequence SEQ ID NO:16. One or more of such amino acid modifications results in increased action of glucosamine-6-phosphate synthase as compared to the naturally occurring glucosamine-6-phosphate synthase having amino acid sequence SEQ ID NO:16. In one embodiment, such an amino acid modification is in an amino acid sequence position in the modified protein (i.e., homologue) which corresponds to one or more of the following amino acid positions in amino acid sequence SEQ ID NO:16: Ile(4), Ile(272), Ser(450), Ala(39), Arg(250), Gly(472), Leu (469).

In another embodiment, such an amino acid modification is selected from the group of a substitution of: (a) an amino acid residue having an aliphatic hydroxyl side group for Ile(4); (b) an amino acid residue having an aliphatic hydroxyl side group for Ile(272); (c) an amino acid residue having an aliphatic side group for Ser(450); (d) an amino acid residue having an aliphatic hydroxyl side group for Ala(39); (e) an amino acid residue having a sulfur-containing side group for Arg(250); (f) an amino acid residue having an aliphatic hydroxyl side group for Gly (472); (g) an amino acid residue having an aliphatic side group for Leu(469); and, (h) combinations of (a)–(g). According to the present invention, amino acid residues having an aliphatic hydroxyl group include serine and threonine, and amino acid residues having aliphatic side groups include glycine, alanine, valine, leucine, isoleucine and proline.

In yet another embodiment of the present invention, an amino acid modification as described above is preferably a substitution selected from the group of: Ile(4) to Thr, Ile (272) to Thr, Ser(450) to Pro, Ala(39) to Thr, Arg(250) to Cys, Gly(472) to Ser, Leu(463) to Pro, and combinations thereof. Specific examples of recombinant nucleic acid molecules having genetic modifications resulting in such amino acid modifications are described in detail in the Examples section.

Preferred genetically modified recombinant nucleic acid molecules comprising a nucleic acid sequence encoding a glucosamine-6-phosphate synthase having increased action include recombinant nucleic acid molecules comprising a nucleic acid sequence which encodes a glucosamine-6-phosphate synthase comprising an amino acid sequence selected from the group of SEQ ID NO:19, SEQ ID NO:22, SEQ ID NO:25, SEQ ID NO:28 and/or SEQ ID NO:31. Other preferred genetically modified recombinant nucleic acid molecules comprise a nucleic acid sequence selected from the group of SEQ ID NO:17, SEQ ID NO:18, SEQ ID NO:20, SEQ ID NO:21, SEQ ID NO:23, SEQ ID NO:24, SEQ ID NO:26, SEQ ID NO:27, SEQ ID NO:29 and/or SEQ ID NO:30. Particularly preferred genetically modified recombinant nucleic acid molecules useful in the present invention include nucleic acid molecules comprising nucleic acid molecules selected from the group of pKLN23-49, pKLN23-54, pKLN23-124, pKLN23-149, pKLN23-151, nglmS-49$_{2184}$, nglmS-49$_{1830}$, nglmS-54$_{2184}$, nglmS-54$_{1830}$, nglmS-124$_{2184}$, nglmS-124$_{1830}$, nglmS-149$_{2184}$, nglmS-149$_{1830}$, nglmS-151$_{2184}$ and nglmS-151$_{1830}$.

The present invention includes a recombinant vector, which includes at least one isolated nucleic acid molecule of the present invention, inserted into any vector capable of delivering the nucleic acid molecule into a bacteria cell. Such a vector can contain bacterial nucleic acid sequences that are not naturally found adjacent to the isolated nucleic acid molecules to be inserted into the vector. The vector can be either RNA or DNA and typically is a plasmid. Recombinant vectors can be used in the cloning, sequencing, and/or otherwise manipulating of nucleic acid molecules. One type of recombinant vector, referred to herein as a recombinant nucleic acid molecule and described in more detail below, can be used in the expression of nucleic acid molecules. Preferred recombinant vectors are capable of replicating in a transformed bacterial or yeast cell, and in particular, in an *Escherichia coli* cell.

Transformation of a nucleic acid molecule into a cell can be accomplished by any method by which a nucleic acid molecule can be inserted into the cell. Transformation techniques include, but are not limited to, transfection, electroporation and microinjection.

Recombinant molecules of the present invention, which can be either DNA or RNA, can also contain additional regulatory sequences, such as translation regulatory sequences, origins of replication, and other regulatory sequences that are compatible with the recombinant cell. One or more recombinant molecules of the present invention can be used to produce an encoded product (e.g., a glucosamine-6-phosphate synthase). In one embodiment, an encoded product is produced by expressing a nucleic acid molecule of the present invention under conditions effective to produce the protein. Such conditions (i.e., culture conditions) have been described above and are further discussed in the Examples section. A preferred method to produce an encoded protein is by transfecting a host cell with one or more recombinant molecules of the present invention to form a recombinant cell.

As discussed above, preferred recombinant molecules of the present invention include, nglmS-$28_{2184}$, nglmS-$28_{1830}$, nglmS-$49_{2184}$, nglmS-$49_{1830}$, nglmS-$54_{2184}$, nglmS-$54_{1830}$, nglmS-$124_{2184}$, nglmS-$124_{1830}$, nglmS-$149_{2184}$, nglmS-$149_{1830}$, nglmS-$151_{2184}$, nglmS-$151_{1830}$, pKLN23-28, pKLN23-49, pKLN23-54, pKLN23-124, pKLN23-149 and/or pKLN23-151.

A recombinant cell is preferably produced by transforming a bacterial cell (i.e., a host cell) with one or more recombinant molecules, each comprising one or more nucleic acid molecules operatively linked to an expression vector containing one or more transcription control sequences. The phrase, operatively linked, refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. In the present invention, expression vectors are typically plasmids. Expression vectors of the present invention include any vectors that function (i.e., direct gene expression) in a yeast host cell or a bacterial host cell, preferably an *Escherichia coli* host cell. Preferred recombinant cells of the present invention are set forth in the Examples section.

Nucleic acid molecules of the present invention can be operatively linked to expression vectors containing regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in yeast or bacterial cells and preferably, *Escherichia coli*. A variety of such transcription control sequences are known to those skilled in the art.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into the host cell chromosome, addition of vector stability sequences to plasmids, substitutions or modifications of transcription control signals (e.g., promoters, operators, enhancers), substitutions or modifications of translational control signals, modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein. Such modifications are described in detail in the Examples section.

The following experimental results are provided for the purposes of illustration and are not intended to limit the scope of the invention.

EXAMPLES

Example 1

The following example describes the production of mutant *Escherichia coli* strains which are blocked in amino acid sugar metabolic pathways involving degradation of glucosamine.

The starting strain for the construction of all glucosamine overproducing strains described herein was *E. coli* W3110 (publicly available from the American Type Culture Collection as ATCC No. 25947), a prototrophic, $F^-$ $\lambda^-$ derivative of *E. coli* K-12 (Bachmann, 1987, "*Escherichia coli* and *Salmonella typhimurium*", *Cellular and Molecular Biology*, pp. 1190–1219; incorporated herein by reference in its entirety). A list of all strains used and produced in the following examples is provided in Table 1.

TABLE 1

*Bacterial strains.*

| Strain | Alias | Genotype | Source/Reference |
|---|---|---|---|
| W3110 | | F⁻ mcrA mcrB IN(rrnD-rrnE)1 λ⁻ | ATCC |
| IBPC 522 | | thi-1 argG6 argE3 his-4 mtl-1 xyl-5 rpsL tsx-29? ΔlacX74 manXYZ8 nagE47 ptsG22 zcf-229::Tn10 | J. Plumbridge |
| IBPC 566 | | thi-1 argG6 argE3 his-4 mtl-1 xyl-5 rpsL tsx-29? ΔlacX74 manXYZ8 zdj-225::Tn10 | J. Plumbridge |
| IBPC 590 | | thi-1 argG6 argE3 his-4 mtl-1 xyl-5 rpsL tsx-29? ΔlacX74 Δnag::TcR | J. Plumbridge |
| 7101-6 | W3110 ptsM | F⁻ mcrA mcrB IN(rrnD-rrnE)1 λ⁻ manXYZ8 zdj-225::Tn10 | W3110 × P1$_{vir}$(IBPC566) |
| 7101-7 | W3110 ptsM | F⁻ mcrA mcrB IN(rrnD-rrnE)1 λ⁻ manXYZ8 zdj-225::Tn10 | W3110 × P1$_{vir}$(IBPC566) |
| 7101-9 | W3110 Δnag | F⁻ mcrA mcrB IN(rrnD-rrnE)1 λ⁻ Δnag::TcR | W3110 × P1$_{vir}$(IBPC590) |
| 7101-13 | W3110 ptsM TcS | F⁻ mcrA mcrB IN(rrnD-nnE)1 λ⁻ manXYZ8 zdj-225::Tn10? TcS | 7101-6 selected on TCS medium |
| 7101-14 | W3110 ptsM TcS | F⁻ mcrA mcrB IN(rrnD-rrnE)1 λ⁻ manXYZ8 zdj-225::Tn10? TcS | 7101-7 selected on TCS medium |
| 7101-15 | W3110 ptsM ptsG | F⁻ mcrA mcrB IN(rrnD-rrnE)1 λ⁻ manXYZ8 zdj-225::Tn10? ptsG22 zcf-229::Tn10 | 7101-14 × P1$_{vir}$(IBPC522) |
| 7101-17 | W3110 ptsM Δnag | F⁻ mcrA mcrB IN(rrnD-rrnE)1 80⁻ manXYZ8 zdj-225::Tn10? TcS Δnag::TcR | 7101-13 × P1$_{vir}$(IBPC590) |
| 7101-22 | W3110 ptsM ptsG TcS | F⁻ mcrA mcrB IN(rrnD-rrnE)1 λ⁻ manXYZ8 zdj-225::Tn10? ptsG22 zcf-229::Tn10? TcS | 7101-15 selected on TCS medium |
| 2123-4 | W3110 ptsM ptsG Δnag | F⁻ mcrA mcrB IN(rrnD-rrnE)1 λ⁻ manXYZ8 zdj-225::Tn10? ptsG22 zcf-229::Tn10? TcS Δnag::TcR | 7101-22 × P1$_{vir}$(IBPC590) |
| W3110(DE3) | | F⁻ mcrA mcrB IN(rrnD-rrnE)1 λDE3 | W3110 lysogenized with λDE3 |
| 7101-9(DE3) | | F⁻ mcrA mcrB IN(rrnD-rrnE)1 λDE3 Δnag::TcR | 7101-9 lysogenized with λDE3 |
| 7101-17(DE3) | | F⁻ mcrA mcrB IN(rrnD-rrnE)1 λDE3 manXYZ8 zdj-225::Tn10? TcS Δnag::TcR | 7101-17 lysogenized with λDE3 |
| 2123-4(DE3) | | F⁻ mcrA mcrB IN(rrnD-rrnE)1 λDE3 manXYZ8 zdj-225::Tn10? ptsG22 zcf-229::Tn10 TcS Δnag::TcR | 2123-4 lysogenized with λDE3. |
| BL21(DE3) | | F⁻ ompT hsdS$_B$ gal dcm λDE3 | Novagen, Inc. |
| ATCC 47002 | JC7623 | F⁻ recB21 recC22 sbcB15 leu-6 ara-14 his-4 λ⁻ | ATCC |
| T-71 | | F⁻ recB21 recC22 sbcB15 leu-6 ara-14 his-4 λ⁻ lacZ::pT7-glmS-Cm8H7 | Integration of pT7-glmS-Cm into lacZ of ATCC47002 by transformation with pkLN23-28 |
| T-81 | | F⁻ recB21 recC22 sbcB15 leu-6 ara-14 his-4 λ⁻ lacZ::pT7-glmS-Cm8H8 | Integration of pT7-glmS-Cm into lacZ of ATCC47002 by transformation with pKLN23-28 |
| 2123-5 | | W3110(DE3) lacZ::pT7-glmS-Cm8H7 | W3110(DE3) × P1$_{vir}$(T-71) |
| 2123-6 | | W3110(DE3) lacZ::pT7-glmS-Cm8H8 | W3110(DE3) × P1$_{vir}$(T-81) |
| 2123-7 | | W3110(DE3) lacZ::pT7-glmS-Cm8H7 | W3110(DE3) × P1$_{vir}$(T-71) |
| 2123-8 | | W3110(DE3) lacZ::pT7-glmS-Cm8H8 | W3110(DE3) × P1$_{vir}$(T-81) |
| 2123-9 | | 7101-9(DE3) lacZ:pT7-glmS-Cm8H7 | 7101-9(DE3) × P1$_{vir}$(T-71) |
| 2123-10 | | 7101-9(DE3) lacZ::pT7-glmS-Cm8H8 | 7101-9(DE3) × P1$_{vir}$(T-81) |
| 2123-11 | | 7101-17(DE3) lacZ::pT7-glmS-Cm8H7 | 7101-17(DE3) × P1$_{vir}$(T-71) |
| 2123-12 | | 7101-17(DE3) lacZ::pT7-glmS-Cm8H8 | 7101-17(DE3) × P1$_{vir}$(T-81) |
| 2123-13 | | 2123-4(DE3) lacZ::pT7-glmS-Cm8H7 | 2123-4(DE3) × P1$_{vir}$(T-71) |
| 2123-14 | | 2123-4(DE3) lacZ::pT7-glmS-Cm8H8 | 2123-4(DE3) × P1$_{vir}$(T-81) |
| NovaBlue | | endA1 hsdR17 supE44 thi-1 recA1 gyrA96 relA1 lac [F' proA⁺B⁺ lacI ZΔM15::Tn10] | Novagen |
| LE392 | | F⁻ e14⁻ (McrA⁻) hsdR514(r⁻m⁺) supE44 supF58 lacY1 or Δlac(IZY)6 galK2 galT22 metB1 trpR55 | Lab collection |
| 2123-16 | | LE392 glmS13 | NG mutagenesis of LE392 |
| 2123-49 | | 7101-17(DE3) lacZ::pT7-glmS11C-Cm8H8 | Error-prone PCR with pKLN23-28; integration of mutant glmS into ATCC47002; transfer to 7101-17(DE3) by P1 transduction |
| 2123-51 | | 7101-17(DE3) lacZ::pT7-glmS52B-Cm8H8 | Error-prone PCR with pKLN23-28; integration of mutant glmS into ATCC47002; transfer to 7101-17(DE3) by P1 transduction |
| 2123-54 | | 7101-17(DE3) lacZ::pT7-glmS8A- | Error-prone PCR with pKLN23-28; |

TABLE 1-continued

Bacterial strains.

| Strain | Alias | Genotype | Source/Reference |
|---|---|---|---|
| | | Cm8H8 | integration of mutant glmS into ATCC47002; transfer to 7101-17(DE3) by P1 transduction |
| 2123-124 | | 7101-17(DE3) lacZ::pT7-glmS94A S-Cm8H8 | Error-prone PCR with pKLN23-28; integration of mutant glmS into ATCC47002; transfer to 7107-17(DE3) by P1 transduction |
| 2123-149 | | 7101-17(DE3) lacZ:pT7-glmS149-Cm8H8 | pKLN23-54 EcoRI-HindIII (1.0 kb) × pKLN23-28 EcoRI-HindIII (6.4 kb); integration of mutant glmS into ATCC47002; transfer to 7101-17(DE3) by P1 transduction |
| 2123-151 | | 7101-17(DE3) lacZ::pT7-glmS151-Cm8H8 | pKLN23-54 EcoRI-HindIII (1.0 kb) × pKLN23-28 EcoRI-HindIII (6.4 kb); integration of mutant glmS into ATCC47002; transfer to 7101-17(DE3) by P1 transduction |

Host strains blocked for glucosamine uptake and degradation were constructed by introducing mutations in the nagE, manXYZ and ptsG genes, which block transport of glucosamine, and the nagA, -B, -C, and -D genes, which are involved in metabolism of glucosamine-6-phosphate. Each of these genes has been described in detail previously herein. Mutations in these genes were introduced into strains using the transducing bacteriophage $P1_{vir}$ (as described in Miller, 1972, "Experiments in Molecular Genetics", Cold Spring Harbor Laboratory, which is incorporated herein by reference in its entirety).

In this technique, genes or mutations from one strain (the donor strain) are transferred to a recipient strain using per the bacteriophage $P1_{vir}$. When bacteriophage $P1_{vir}$ is grown on the donor strain, a small portion of the phage particles that are produced contain chromosomal DNA from the donor rather than the normal complement of phage DNA. Upon infection of the recipient strain with bacteriophage grown on the donor strain, those bacteriophage particles containing chromosomal DNA from the donor strain can transfer that DNA to the recipient strain. If there is a strong selection for the DNA from the donor strain, recipient strains containing the appropriate gene or mutation from the donor strain can be selected.

To grow $P1_{vir}$ on a donor strain, an existing bacteriophage stock was used to infect a culture of that strain. The recipient strain was grown at 37° C. in LBMC medium (10 g/L Bacto tryptone, 5 g/L yeast extract, 10 g/L NaCl, 1 mM $MgCl_2$, 5 mM $CaCl_2$) until the absorbance at 600 nm was approximately 1.0, corresponding to approximately $6 \times 10^8$ cells per mL of culture. One mL of the culture was then infected with a dilution of the phage stock at a ratio of approximately one phage per 10 cells. The mixture was incubated without shaking for 20 minutes at 37° C., then transferred to 10 mL of prewarmed LBMC broth in a 125 mL baffled Erlenmeyer flask. The resulting culture was shaken vigorously for 2–3 hours at 37° C. During this period, it was generally observed that the culture would become more turbid, indicating bacterial growth. Toward the end of this incubation period, the culture would become clear, indicating cell lysis due to bacteriophage growth. After lysis had occurred, the culture was cooled on ice, a few drops of chloroform were added, and the flask was shaken briefly. The contents of the flask were then centrifuged to remove the cell debris and chloroform, and the resulting supernatant generally contained between $10^8$ and $10^9$ bacteriophage per mL.

Mutations were transferred to recipient strains by transduction with $P1_{vir}$ grown on the appropriate donor strain as described above. For transduction with $P1_{vir}$, a culture of the recipient strain was grown overnight at 37° C. in LBMC broth. 0.1 mL of culture was mixed with 0.1 mL of bacteriophage lysate or a serial dilution of the lysate in a sterile test tube and incubated at 37° C. for 20 minutes. 0.2 mL of 1 M sodium citrate was added to the tube, and the mixture was plated to selective medium. For each transduction, controls containing uninfected cells and bacteriophage lysates without cells were performed as described above. For the production of strains blocked in glucosamine degradation, selections were for tetracycline resistance as described below. Tetracycline resistant mutants were selected by plating to LB medium (10 g/L Bacto tryptone, 5 g/L yeast extract, 10 g/L NaCl) containing 12.5 μg/mL tetracycline and 10 mM sodium citrate.

The mutations in the nag genes were introduced simultaneously as a deletion mutation (Δnag::$Tc^R$). In strain IBPC590 (Plumbridge, Table 1), which contains this mutation, the nag genes have been replaced by a tetracycline-resistance ($Tc^R$) determinant. As a result, the mutation which removes the nag functions was transferred to appropriate recipient hosts by selection for tetracycline resistance. In this case, since the $Tc^R$ determinant was contained within the mutation of interest, the Δnag and $Tc^R$ mutations were 100% linked. That is, all of the recipient strains receiving the $Tc^R$ determinant from IBPC590 also received the Δnag mutation. This was confirmed by examining the growth phenotype of the tetracycline resistant strains resulting from infection with $P1_{vir}$ grown on IBPC590. All such strains were unable to grow on media containing glucosamine or N-acetylglucosamine as carbon sources, indicating the presence of the Δnag mutation.

Mutations in the manXYZ and ptsG genes were also introduced by $P1_{vir}$ transduction using phage grown on strains IBPC566 and IBPC522 (Plumbridge, Table 1), respectively. These strains also contained tetracycline-resistance determinants linked to the mutations of interest (designated zdj-225::Tn10 and zcf-229::Tn10, respectively). In these strains, the $Tc^R$ determinants were not within the gene but were linked to the gene. Accordingly, not all recipient strains receiving the $Tc^R$ determinant contained the mutations of interest. The degree of linkage is indicative of the distance on the chromosome between the $Tc^R$ determinant and the mutation of interest. As a result, it was necessary to screen tetracycline resistant strains for manXYZ and ptsG. The manXYZ strains grew slowly on mannose and failed to grow on glucosamine as sole carbon sources for growth. The ptsG strains grew slowly on glucose as sole carbon source.

Because all of the selections for the mutations described above were for tetracycline resistance, it was necessary to render strains tetracycline sensitive between steps if multiple mutations were to be introduced. To accomplish this, tetracycline-resistant strains were plated to TCS medium (15 g/L agar, 5 g/L Bacto tryptone, 5 g/L yeast extract, 50 mg/L chlortetracycline hydrochloride, 10 g/L NaCl, 10 g/L $NaH_2PO_4.H_2O$, 12 mg/L fusaric acid, and 0.1 mM $ZnCl_2$) which selects for tetracycline sensitive mutants (described in Maloy and Nunn, 1981, *J. Bacteriol.*, 145:1110–1112, which is incorporated herein by reference in its entirety). Colonies arising on this medium were purified by restreaking to the same medium, then checking individual colonies for tetracycline sensitivity by plating to LB media with and without 12.5 μg/mL tetracycline.

Figure 3:
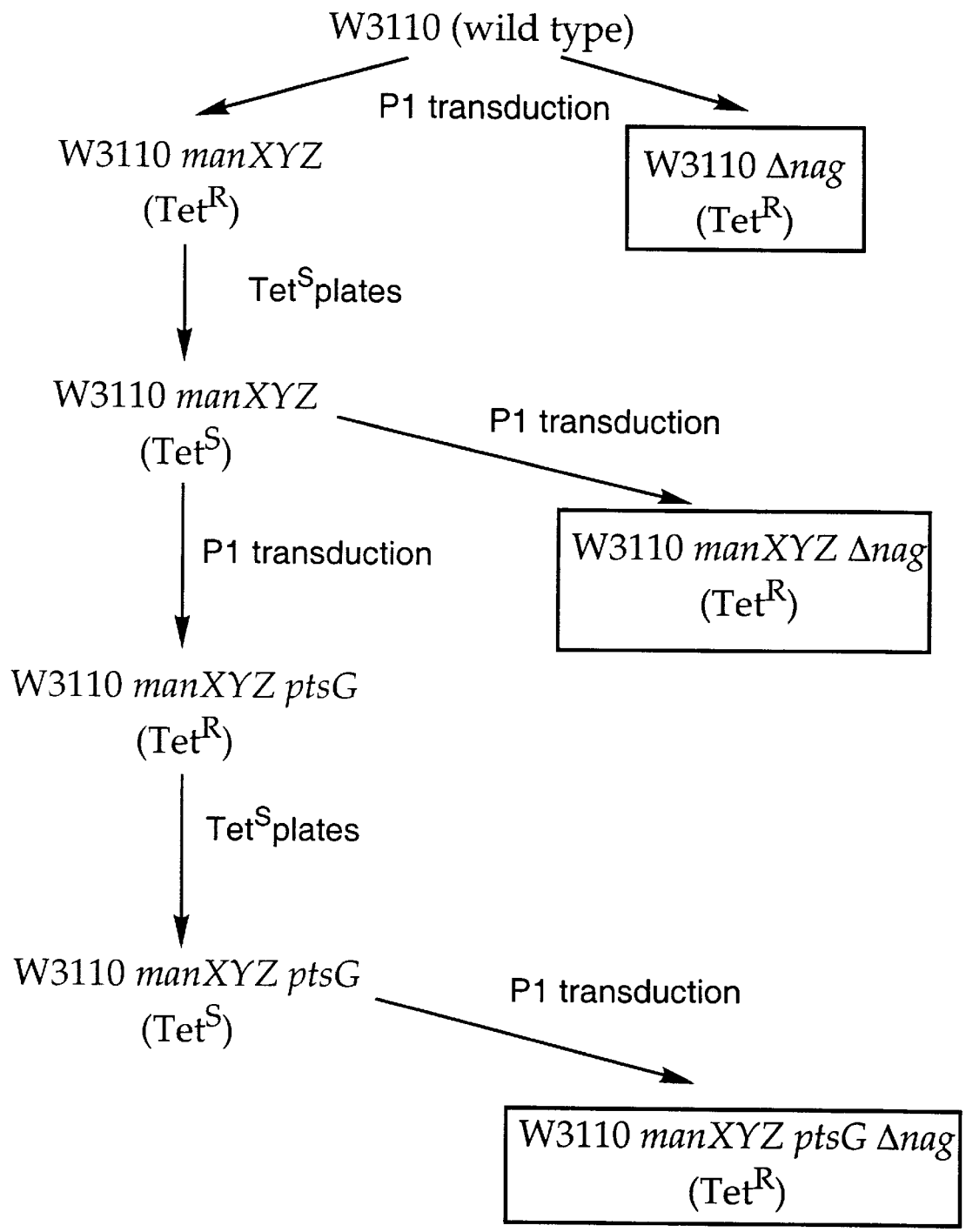
FIG. 3 is a schematic representation of the production of *Escherichia coli* strains containing combinations of the manXYZ, ptsG, and Δnag mutations.

The scheme described above for the production of strains containing combinations of the manXYZ, ptsG, and Δnag mutations is presented schematically in FIG. 3.

Example 2

The following Example describes the cloning and overexpression of the glmS gene and the integration of the T7-glmS gene cassette into the *E. coli* chromosome.
Cloninc and Overexpression of the glmS Gene.

Using information obtained from the published sequence of the glmS gene (Walker et al., 1984, Biochem. J., 224:799–815, which is incorporated herein by reference in its entirety), primers were synthesized to amplify the gene from genomic DNA isolated from strain W3110 (Table 1) using the polymerase chain reaction (PCR). The primers used for PCR amplification were designated Up1 and Lo8 and had the following sequences:

Up1: 5'-CGGTCTCCCATGTGTGGAATTGTTGGCGC-3' (SEQ ID NO:1)

Lo8: 5'-CTCTAGAGCGTTGATATTCAGTCAATTAC AAACA-3' (SEQ ID NO:2) The Up1 primer contained sequences corresponding to the first twenty nucleotides of the glmS gene (represented in nucleotides 10–29 of SEQ ID NO:1) preceded by a BsaI restriction endonuclease recognition site (GGTCTC, represented in nucleotides 2–7 of SEQ ID NO:1). The Lo8 primer contained sequences corresponding to positions between 145 and 171 bases downstream of the glmS gene (represented in nucleotides 8–34 of SEQ ID NO:2) preceded by a XbaI restriction endonuclease site (TCTAGA, represented in nucleotides 2–7 of SEQ ID NO:2). PCR amplification was conducted using a standard protocol to generate a fragment of DNA containing the glmS gene with 171 base pairs of DNA downstream of the gene flanked by BsaI and XbaI sites. This DNA fragment was cloned into the vector pCR-Script™SK(+) (Stratagene Cloning Systems, La Jolla, Calif.) using materials and instructions supplied oy the manufacturer. The resulting plasmid was designated pKLN23-20.

One consequence of this cloning was that it placed a unique SacI restriction endonuclease site downstream of the gene. This allowed excision of a fragment of DNA containing the glmS gene from pKLN23-20 using the restriction endonucleases BsaI and SacI. This fragment was then cloned between the NcoI and SacI sites of the expression vector pET-24d(+) (Novagen, Inc., Madison, Wis.) to generate plasmid pKLN23-23. The pET-24d(+) expression vector is based on the T7 promoter system (Studier and Moffatt, 1986, *J. Mol. Biol.*, 189:113–130). Cloning in this manner resulted in placement of the glmS gene behind the T7-lac promoter contained on pET-24d(+). The T7-lac promoter is specifically recognized by the T7 RNA polymerase and is only expressed in strains containing a cloned T7 gene 1, which encodes the T7 RNA polymerase. The cloned T7 polymerase gene is contained on a defective bacteriophage λ phage designated λDE3. Strains in which the λDE3 element is integrated into the chromosome contain the T7 RNA polymerase gene driven by the lacUV5 promoter. In those strains, expression of the T7 RNA polymerase gene can be induced using the lactose analog isopropylthio-β-D-galactopyranoside (IPTG). Accordingly, addition of IPTG to such cultures results in induction of the T7 RNA polymerase gene and expression of any genes controlled by the T7 or T7-lac promoter.

To verify that pKLN23-23 contained the glmS gene driven by the T7-lac promoter, the plasmid was transferred to strain BL21(DE3) (Novagen, Inc.) (Table 1). Strain BL21(DE3)/pKLN23-23 was grown in duplicate in LB medium containing 50 mg/L kanamycin (kanamycin resistance is encoded by the plasmid). One of the duplicates was induced with 1 mM IPTG; the other was not. When the total proteins were examined from these two cultures by sodium dodecyl sulfate polyacrylamide gel electrophoresis, a prominent protein of approximately 70,000 molecular weight, corresponding to the predicted size for the glmS gene product, was observed in cells from the induced culture but not in cells from the uninduced culture. A preliminary enzyme assay from an induced culture indicated several hundred fold higher glucosamine-6-phosphate synthase activity in the induced culture than in what had typically been observed in a wild type strain.
Integration of the T7-glmS Gene Cassette into the *E. coli* Chromosome.

The glmS gene driven by the T7-lac (the T7-glmS gene cassette) promoter was transferred to the chromosome of *E. coli* strains by a multistep process. First, the cassette was cloned into plasmid pBRINT-Cm (Balbás et al., 1996, *Gene* 96:65–69), which is incorporated herein by reference in its entirety). The gene cassette was then integrated into the chromosome of strain ATCC47002 (Table 1) by the techniques described by Balbás et al., 1996, supra, to generate strains T-71 and T-81 (Table 1). Finally, the gene cassette was transferred to strains of interest by transduction with $P1_{vir}$, as described below.

The T7-glmS cassette was excised from pKLN23-23 by performing a partial digest of the plasmid with restriction endonuclease BglII and a complete digest with restriction endonuclease HinDIII. Plasmid pKLN23-23 contains a BglII site approximately 20 base pairs upstream of the T7 promoter. The glmS gene also contains two BglII sites. A partial digest with this enzyme was necessary to cut the plasmid upstream of the T7 promoter while avoiding the two internal sites. Plasmid pKLN23-23 also contains a unique HinDIII site downstream of the glmS gene. The excised T7-glmS cassette was then cloned between the BamHI and HinDIII sites of pBRINT-Cm. This resulted in the production of plasmids designated pKLN23-27 and pKLN23-28. Plasmids pKLN23-27 and pKLN23-28 contain the T7-glmS cassette in addition to a chloramphenicol resistance determinant flanked by the 5'- and 3'-termini of the *E. coli* lacZ gene.

Strain ATCC 47002 (Table 1) contains mutations that confer upon it an inability to maintain plasmids such as pBRINT-Cm which contain a ColE1 origin of replication. When such plasmids are transferred to this strain, selection for genetic markers contained on the plasmid results in integration of the plasmid into the chromosome (Balbás et al., 1996, supra). As mentioned above, plasmids pKLN23-27 and -28 contain the T7-glmS cassette and a chloramphenicol resistance determinant flanked by the 5'- and 3'-termini of the E. coli lacZ gene. The lacZ sequences target the incoming DNA to the lacZ gene contained in the chromosome. Integration at the lacZ locus replaces the intact lacZ gene, which encodes the enzyme β-galactosidase, with a partial lacZ gene interrupted by the T7-glmS-Cm cassette. As a result, integration at lacZ results in the strain becoming β-galactosidase negative. The plasmid also contains an ampicillin resistance determinant remote from the 5'-lacZ-T7-glmS-Cm-lacZ-3' cassette. Integration at lacZ and plasmid loss also results in ampicillin sensitivity.

Plasmids pKLN23-27 and -28 were transferred to strain ATCC 47002, and cells were plated to LB medium containing 10 $\mu$g/mL chloramphenicol, 1 mM IPTC, and 40 $\mu$g/mL 5-bromo-4-chloro-3-indolyl-β-D-galactopyranoside (X-gal). The X-gal contained in the medium is a chromogenic β-galactosidase substrate. Hydrolysis of X-gal by β-galactosidase results in a blue derivative. Inclusion of X-gal and IPTG, which induces the native lacZ gene, results in blue lacZ-positive colonies and white lacZ-negative colonies. White (lacZ-negative) chloramphenicol resistant colonies were then selected and purified. The strains were then verified for sensitivity to ampicillin by plating to LB media with and without 100 $\mu$g/mL ampicillin. DNA integration was further confirmed using a PCR scheme as described by Balbás et al., 1996, supra. Integrants T-71 and T-81 (Table 1) resulted from the integration of the desired segments of plasmids pKLN23-27 and pKLN23-28, respectively, into the chromosome of ATCC 47002.

The T7-glmS-Cm cassette was then transferred to strains W3110(DE3), 7101-9(DE3), 7101-17(DE3), and 2123-4 (DE3) by P1$_{vir}$ transduction, as described in Example 1, using lysates prepared on strains T-71 and T-81. These strains contain various combinations of the Δnag, manXYZ, and ptsG mutations in addition to the λDE3 element necessary for expression from the T7-lac promoter. The λDE3 element was introduced to these strains using the λDE3 lysogenization kit produced by Novagen, Inc. (Madison, Wis.). Transductants were selected on LB agar plates containing 30 $\mu$g/mL chloramphenicol and 10 mM sodium citrate. Loss of β-galactosidase activity was verified on plates containing X-gal and IPTG and DNA integration was further confirmed using a PCR scheme as described by Balbás et al., 1996, supra.

Glucosamine-6-phosphate synthase activity was measured in production strains containing integrated T7-glmS cassettes after growth in LB medium with and without IPTG (Table 2). Glucosamine-6-phosphate synthase was assayed in crude cell extracts using either calorimetric or spectrophotometric assays (Badet et al., 1987, Biochemistry 26:1940–1948) as described below. The extracts used for those assays were prepared by suspending washed cell pellets in 5 mL of 0.1 M KH$_2$PO$_4$/K$_2$HPO$_4$, pH 7.5 per gram of wet cell paste, passing the suspension through a French press at 16,000 psi, and centrifuging the disrupted cell suspension at 35,000–40,000×g for 15 to 20 minutes. The supernatant was used as the source of enzyme for the assay.

For a calorimetric assay, 1 mL reactions were prepared containing 45 mM KH$_2$PO$_4$/K$_2$HPO$_4$, 20 mM fructose-6-phosphate, 15 mM L-glutamine, 2.5 mM EDTA, pH 7.5, and cell extract. The reactions were incubated at 37° C. for 20 minutes and stopped by boiling for 4 minutes. The resulting precipitate was removed by centrifugation and the supernatant was assayed for glucosamine-6-phosphate by a modification of the method of Elson and Morgan (1933, Biochem. J. 27:1824–1828) essentially as described by Zalkin (1985, Meth. Enzymol. 113:278–281), both publications of which are incorporated herein by reference in their entireties. To 100 $\mu$L of the above supernatant was added 12.5 $\mu$L of saturated NaHCO$_3$ and 12.5 $\mu$L of cold, freshly prepared 5% aqueous acetic anhydride. After incubating for 3 minutes at room temperature, the mixture was boiled for 3 minutes to drive off excess acetic anhydride. After cooling to room temperature, 150 $\mu$L of 0.8 M potassium borate, pH 9.2 (0.8 M H$_3$BO$_3$ adjusted to pH 9.2 with KOH) was added and the mixture was boiled for 3 minutes. After cooling to room temperature, 1.25 mL Ehrlich's reagent (1% p-dimethylaminobenzaldehyde in glacial acetic acid containing 0.125 N HCl) was added to each tube. After incubating at 37° C. for 30 minutes, the absorbance at 585 nm was measured and the amount of glucosamine-6-phosphate formed was determined using a standard curve. In the absence of the substrate, fructose-6-phosphate, or when boiled extract was used in the assay, no significant absorbance at 585 nm was observed.

In the spectrophotometric assay, 1 mL reactions containing 50 mM KH$_2$PO$_4$/K$_2$HPO$_4$, 10 nM fructose-6-phosphate, 6 mM L-glutamine, 10 mM KCl, 0.6 mM acetylpyridine adenine dinucleotide (APAD), and 50–60 Units of L-glutamic dehydrogenase (Sigma Type II from bovine liver) were run at room temperature. The activity was followed by monitoring the absorbance at 365 nm after the addition of extract and corrected for the small absorbance increase observed in the absence of extract. The activity was calculated using a molar extinction coefficient for APAD of 9100.

TABLE 2

Glucosamine 6-Phosphate Synthase Activity in Production Strains Containing Integrated T7-glmS Cassettes

| | | Activity, ($\mu$mole per minute per mL of extract) | |
|---|---|---|---|
| Strain | Host Genotype | −IPTG | +IPTG |
| 2123-5 | DE3 | 23 | 64 |
| 2123-6 | DE3 | 4 | 4 |
| 2123-7 | DE3 | 23 | 96 |
| 2123-8 | DE3 | 25 | 89 |
| 2123-9 | DE3 Δnag | 26 | 58 |
| 2123-10 | DE3 Δnag | 33 | 67 |
| 2123-11 | DE3 Δnag manXYZ | 32 | 59 |
| 2123-12 | DE3 Δnag manXYZ | 17 | 67 |
| 2123-13 | DE3 Δnag manXYZ ptsG | 21 | 68 |
| 2123-14 | DE3 Δnag manXYZ ptsG | 20 | 88 |

Table 2 shows that, on average, the activity of glucosamine-6-phosphate synthase in production strains containing integrated T7-glmS cassettes was about three- to four-fold higher with IPTG induction than without. The activities were substantially higher than those obtained with a wild type glmS strain driven by its native promoter, which typically were in the range of 0.05–0.1 $\mu$mole per minute per mL of extract. One of the strains, 2123-6, apparently suffered an aberrant integration event since the activity was lower than that observed in the other strains and was not influenced by the presence of IPTG in the medium.

Example 3

The following example shows the effect of strain genotype on glucosamine accumulation.

Strains with T7-glmS integrants, produced as described in Example 2, as well as the corresponding parent strains without integrated DNA, were grown in shake flasks containing M9A medium (14 g/L $K_2HPO_4$, 16 g/L $KH_2PO_4$, 1 g/L $Na_3Citrate.2H_2O$, 5 g/L $(NH_4)_2SO_4$, pH 7.0) supplemented with 20 g/L glucose, 10 mM $MgSO_4$, 1 mM $CaCl_2$, and 1 mM IPTG. Samples were taken periodically over the course of two days, and the glucosamine concentration in the culture supernatant was measured using the modified Elson-Morgan assay as described in Example 2. Samples were assayed with and without acetic anhydride treatment, and the amount of glucosamine present was determined from the net absorbance using a standard curve.

Glucosamine concentrations after 24 hours of cultivation, at which time the concentration peaked, are indicated in Table 3. The results shown in Table 3 indicate that for significant glucosamine production to occur, the T7-glmS gene cassette must be present. The data also indicate that the presence of the Δnag mutation in the host results in a significant increase in glucosamine accumulation compared with its absence. Little effect of the manXYZ mutation was observed in this experiment. In further shake flask experiments, however, strain 2123-12 accumulated slightly higher glucosamine concentrations on a consistent basis.

TABLE 3

Glucosamine in Culture Supernatants of Production Strains

| Strain | Genotype | Glucosamine Concentration, mg/L (24 hours) |
| --- | --- | --- |
| 2123-5 | DE3, T-71 integrant | 21 |
| 2123-7 | DE3, T-71 integrant | 23 |
| 2123-9 | DE3 Δnag, T-71 integrant | 67 |
| 2123-10 | DE3 Δnag, T-81 integrant | 80 |
| 2123-11 | DE3 Δnag manXYZ, T-71 integrant | 65 |
| 2123-12 | DE3 Δnag manXYZ, T-81 integrant | 63 |
| W3110(DE3) | DE3, no integrant | 4 |
| 7101-9(DE3) | DE3 Δnag, no integrant | 0 |
| 7101-17(DE3) | DE3 Δnag manXYZ, no integrant | 0 |

Example 4

The following example demonstrates the effect feeding nutrients to the cultures has on glucosamine accumulation.

In early experiments, it was observed that glucosamine accumulation ceased when glucose was depleted from cultures. In the experiment summarized by Table 4 and FIG. 4, it was found that increased glucosamine accumulation could be accomplished by feeding additional glucose and ammonium sulfate as they became depleted. For this experiment, strain 2123-12 was grown in M9A medium supplemented with 10 mM $MgSO_4$, 1 mM $CaCl_2$, and 1 mM IPTG. Initial glucose concentrations and feeding regimens were varied as indicated in Table 4. In one of the flasks, the initial ammonium sulfate concentration was 10 g/L rather than the 5 g/L normally used in M9A medium. Glucose concentration was monitored in shake flasks during cultivation using Diastix® glucose test strips (Bayer Corporation Diagnostics Division, Elkhart, Ind.). When the glucose concentration was at or near depletion (<5 g/L remaining), glucose and/or ammonium sulfate were supplemented as indicated in Table 4. pH was also monitored during cultivation. When the pH varied significantly from the initial pH of 7.0, it was adjusted to 7.0 with sodium hydroxide.

TABLE 4

Shake Flask Experiment to Examine the Effect of Glucose Feeding

| Flask No. | Initial Glucose, g/L | Initial Ammonium Sulfate, g/L | Feed |
| --- | --- | --- | --- |
| 1 | 20 | 5 | None |
| 2 | 50 | 5 | None |
| 3 | 50 | 10 | None |
| 4 | 20 | 5 | 20 g/L Glucose |
| 5 | 20 | 5 | 20 g/L Glucose + 5 g/L AmSO4 |

Figure 4:
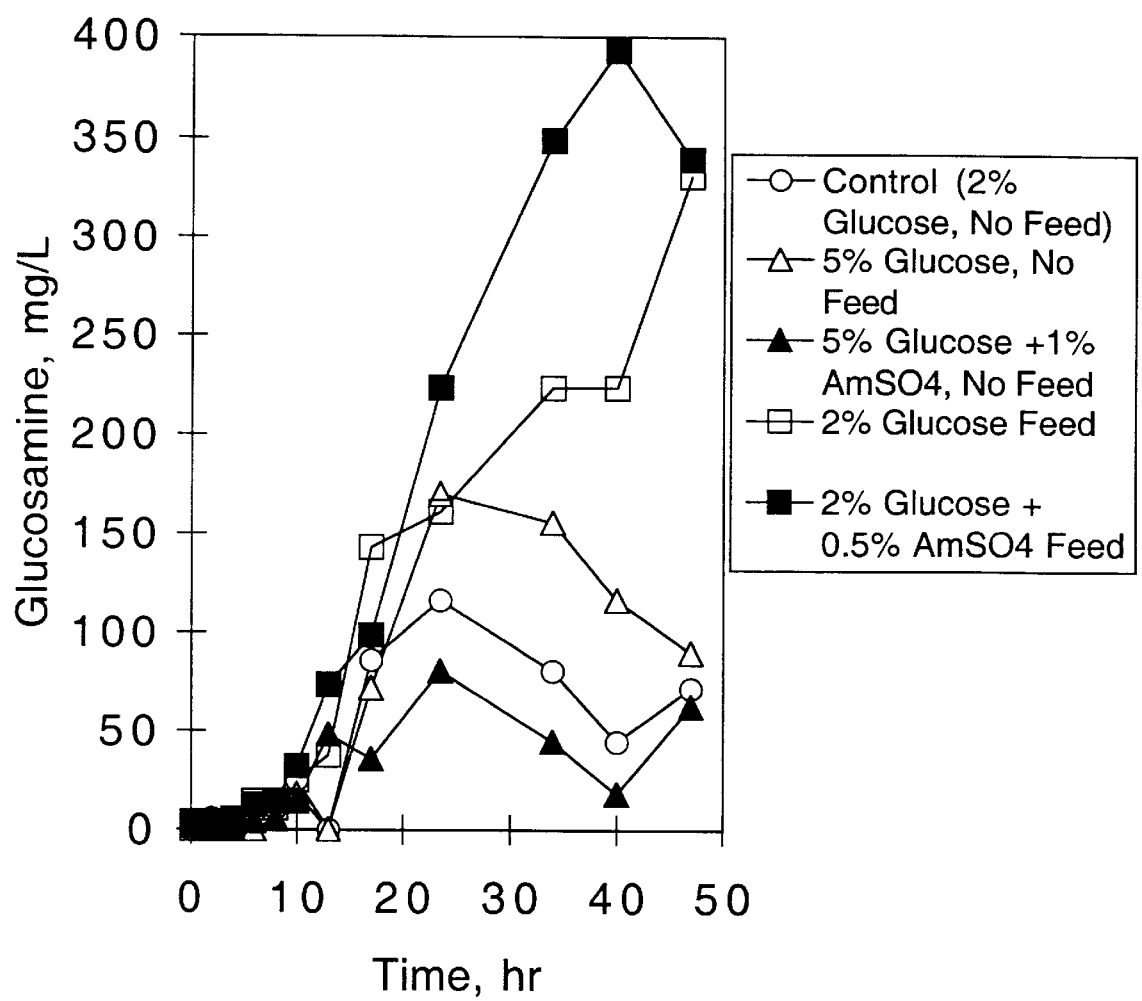
FIG. 4 is a line graph illustrating the effects on glucosamine accumulation of feeding additional glucose and ammonium sulfate to cultures.

As FIG. 4 indicates, increasing the supply of glucose had a positive effect on glucosamine accumulation. By periodically feeding with glucose and ammonium sulfate (20 g/L and 5 g/L additions, respectively), a maximum accumulation of 0.4 g/L of glucosamine was observed, approximately four-fold higher than what was observed in the absence of feeding.

Example 5

The following example describes the isolation of mutant glmS genes encoding glucosamine-6-phosphate synthase enzymes with decreased sensitivity to glucosamine-6-phosphate product inhibition.

White (1968, *Biochem. J.*, 106:847–858) first demonstrated that glucosamine-6-phosphate synthase was inhibited by glucosamine-6-phosphate. Using the spectrophotometric assay for glucosamine-6-phosphate synthase as described in Example 2, the effects of glucosamine-6-phosphate and glucosamine on glucosamine-6-phosphate synthase were measured. For determination of product inhibition, assays were run in the presence of various concentrations of added glucosamine-6-phosphate.

Figure 5:
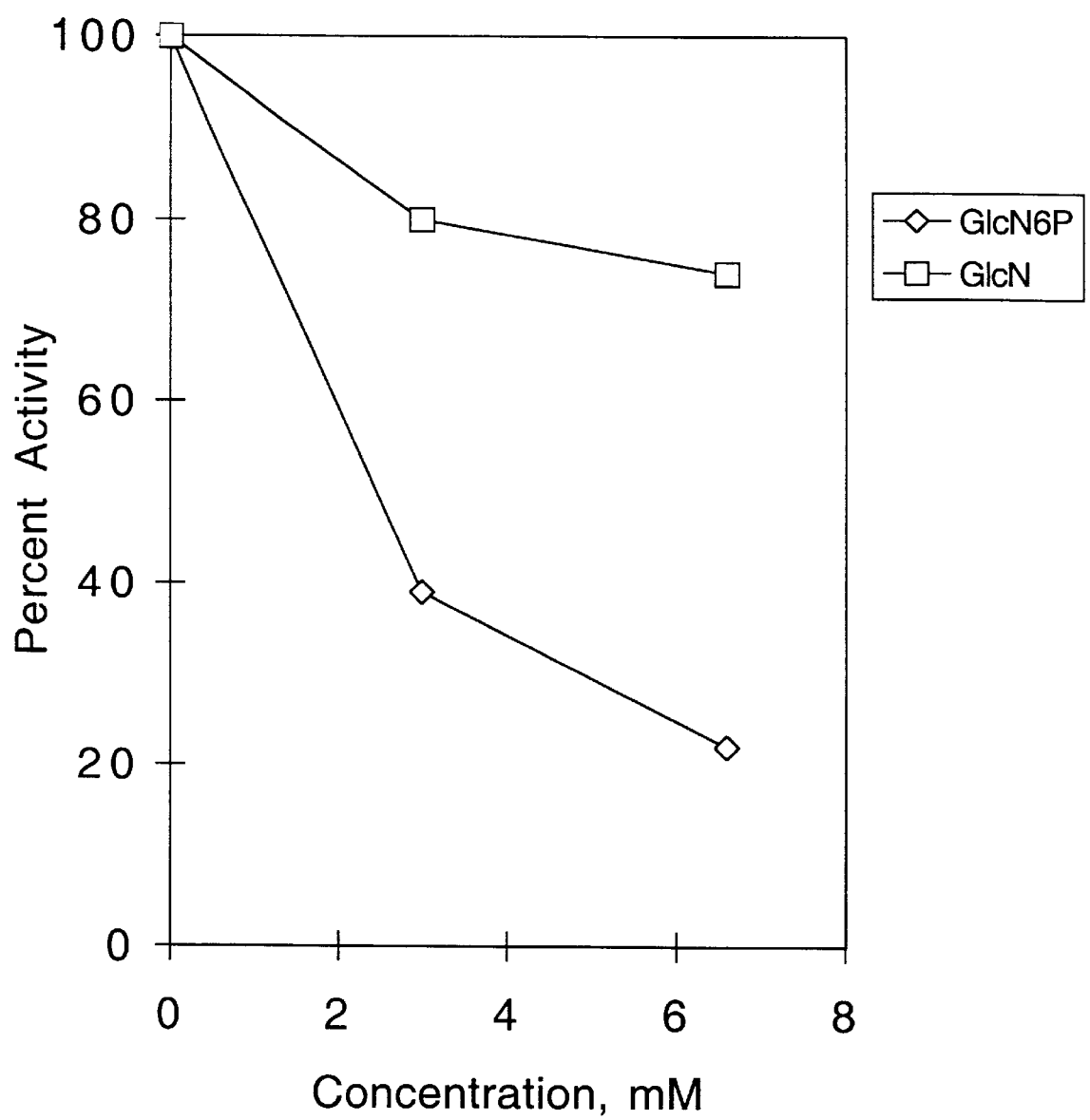
FIG. 5 is a line graph which shows that glucosamine-6-phosphate synthase is inhibited by glucosamine-6-phosphate and glucosamine.

As indicated in FIG. 5, the enzyme is significantly inhibited by glucosamine-6-phosphate and slightly inhibited by glucosamine. These results are similar to those obtained by White, 1968, supra. This inhibition may be a key factor in limiting glucosamine accumulation in the glucosamine production strains.

To further increase glucosamine synthesis in production strains, efforts were made to isolate mutants of the glmS gene encoding glucosamine-6-phosphate synthase variants with reduced product inhibition. To accomplish this, the cloned gene was amplified using the technique of error-prone PCR. In this method, the gene is amplified under conditions that lead to a high frequency of misincorporation errors by the DNA polymerase used for the amplification. As a result, a high frequency of mutations are obtained in the PCR products.

Plasmid pKLN23-28 contains a unique SpeI restriction endonuclease site 25 base pairs upstream of the T7 promoter and 111 base pairs upstream of the start of the glmS gene. The plasmid also contains a unique HinDIII site 177 base pairs downstream of the glmS gene. PCR primers of the following sequences were synthesized to correspond to regions just upstream of the SpeI and downstream of the HinDIII sites, respectively:

5'-ATGGATGAGCAGACGATGGT-3' (SEQ ID NO:3)
5'-CCTCGAGGTCGACGGTATC-3' (SEQ ID NO:4)

Amplification with these primers (SEQ ID NO:3 and SEQ ID NO:4) allowed mutagenesis of a 2247 base pair region that included the entire glmS gene. PCR conditions were as described by Moore and Arnold, 1996, *Nature Biotechnol-* ogy 14:458–467, which is incorporated herein by reference in its entirety. Briefly, a 100 µL solution was prepared containing 1 mM each of the four deoxynucleotide triphosphates, 16.6 mM ammonium sulfate, 67 mM Tris-HCl, pH 8.8, 6.1 mM MgCl$_2$, 6.7 µM EDTA, 10 mM β-mercaptoethanol, 10 µL DMSO, 30 ng each of the primers (SEQ ID NO:3 and SEQ ID NO:4), either 7 or 35 ng of plasmid pKLN23-28 linearized with Kpn I, and 2.5 Units of Taq DNA polymerase (Perkin Elmer-Cetus, Emeryville, Calif.). The reaction mixture was covered with 70 µL of mineral oil and placed in a thermocycler, where the following steps were repeated for 25 cycles:

1 minute at 94° C.
1 minute at 42° C.
2 minutes at 72° C.

Under these conditions, an error frequency of approximately one mutation per 1000 base pairs has been reported (Moore and Arnold, 1996, sulpra) The product of the reaction was recovered, purified, and digested with SpeI and HinDIII, and cloned into the SpeI-HinDIII backbone fragment of pKLN23-28, which effectively substitutes for the wild type glmS gene on the SpeI-HinDIII fragment of pKLN23-28. The cloned DNA was used, to transform strain NovaBlue (Novagen, Inc., Madison, Wis.), and the transformed cells were plated to LB agar containing ampicillin. A total of 9000 plasmid-containing colonies were pooled from the ampicillin plates and plasmid DNA was prepared from the pooled cells to generate a library of pKLN23-28 derivative plasmids containing mutations in the cloned glmS gene.

The mutant plasmids generated by error-prone PCR were screened for their ability to confer increased glucosamine production in a Δnag manXYZ DE3 host background. This screen was in the form of a bioassay in which the ability of plasmid-containing strains to crossfeed glucosamine-requiring strains of *E. coli* was assessed.

Strains of *E. coli* (Sarvas, 1971, *J. Bacteriol.* 105:467–471; Wu and Wu, 1971, *J. Bacteriol.* 105:455–466) and *Bacillus subtilis* (Freese et al., 1970, *J. Bacteriol.* 101:1046–1062) which are defective for glucogamine-6-pnosphate synthase require glucosamine or N-acetylglucosamine for growth. A glucosamine-requiring strain of *E. coli* was isolated after mutagenesis with N-methyl-N'-nitro-N-nitrosoguanidine (NG). Strain LE392 (Table 1) was grown in LB medium to a cell density of 6×10$^8$ cells per mL. 50 µL of 2.5 mg/mL NG dissolved in methanol was added to 2 mL of this culture and the mixture was incubated at 37° C. for 20 minutes. This treatment resulted in about 10% survival of the strain. The mutagenized cells were harvested by centrifugation, and the cells were washed twice by suspension in 0.9% NaCl and recentrifugation. The washed cells were diluted and plated to nutrient agar medium (NA; 5 g/L Bacto peptone, 3 g/L beef extract, 15 g/L agar) containing 0.2 g/L, N-acetylglucosamine at a density of between 50 and 200 colony forming units per plate. Approximately 13,000 colonies were plated. These colonies were replica-plated to NA agar with and without 0.2 g/L N-acetylglucosamine. Twenty-two colonies grew on NA with 0.2 g/L N-acetylglucosamine but not on NA without 0.2 g/L N-acetylglucosamine. These colonies were purified by streaking to NA with 0.2 g/L N-acetylglucosamine, and their growth phenotype was rechecked. Of the original 22 colonies selected, five had the phenotype expected of a glmS mutant of LE392. They failed to grow on NA but grew on NA supplemented with 0.2 g/L of glucosamine or 0.2 g/L N-acetylglucosamine. They also failed to grow on glucose minimal agar, but grew on glucose minimal agar supplemented with 0.2 g/L N-acetylglucosamine. One of these mutants was designated 2123-16 (Table 1).

For the cross-feeding assay, agar plates containing either glycerol or fructose as the principle carbon source for growth were overlaid with cells from a culture of strain 2123-16, the glucosamine-requiring strain isolated as described above. Glucosamine-producing strains were stabbed into the agar and the ability to produce glucosamine was assessed based on the size of the "halo" of growth of the indicator strain surrounding the stab. Those stabs surrounded by larger halos were considered to produce greater amounts of glucosamine.

The media used for the cross-feeding assays consisted of M9 minimal medium (6 g/L Na$_2$HPO$_4$, 3 g/L KH$_2$PO$_4$, 0.5 g/L NaCl, 1 g/L NH$_4$Cl, 1 MM MgSO$_4$, 0.1 mM CaCl$_2$) supplemented with 40 mg/L of L-methionine (required for growth of strains LE392 or 2123-16) and 2 g/L of either glycerol or fructose. These plates were overlaid with strain 2123-16 as follows. A culture of strain 2123-16 was grown overnight at 37° C. in LB medium containing 1 g/L N-acetylglucosamine. The culture was harvested by centrifugation, and the cells ware washed twice by suspension in 0.9% NaCl and recentrifugation. The washed cells were suspended in the original volume of 0.9% NaCl. For each plate to be overlaid, 0.1 mL of washed cell suspension was mixed with 3 mL of molten (50° C.) F-top agar (8 g/L NaCl, 8 g/L agar) and poured onto the plate.

The library of pKLN23-28 mutant plasmids was transferred to strain 7101-17(DE3) and transformed cells were plated to LB agar containing 100 µg/mL ampicillin. Each colony arising on these plates contained an individual member of the mutant plasmid library. The colonies were screened by picking them from the LB+ampicillin plates and stabbing them sequentially into:

(1) LB agar+ampicillin;
(2) glycerol minimal agar overlaid with strain 2123-16; and,
(3) fructose minimal agar overlaid with strain 2123-16

All plates were incubated for about 24 hours at 37° C. After this incubation period, halos of growth of the 2123-16 indicator strain could be observed surrounding the stabs in the overlaid plates. Those colonies giving rise to the larger halos were picked from the corresponding LB+ampicillin plate and streaked for purification. In an initial screen, 4368 mutant candidates were screened, and 96 initial candidates were identified. Upon rescreening those, 30 appeared to be superior to the rest, i.e. resulted in larger halos of the indicator strain.

Figure 6:
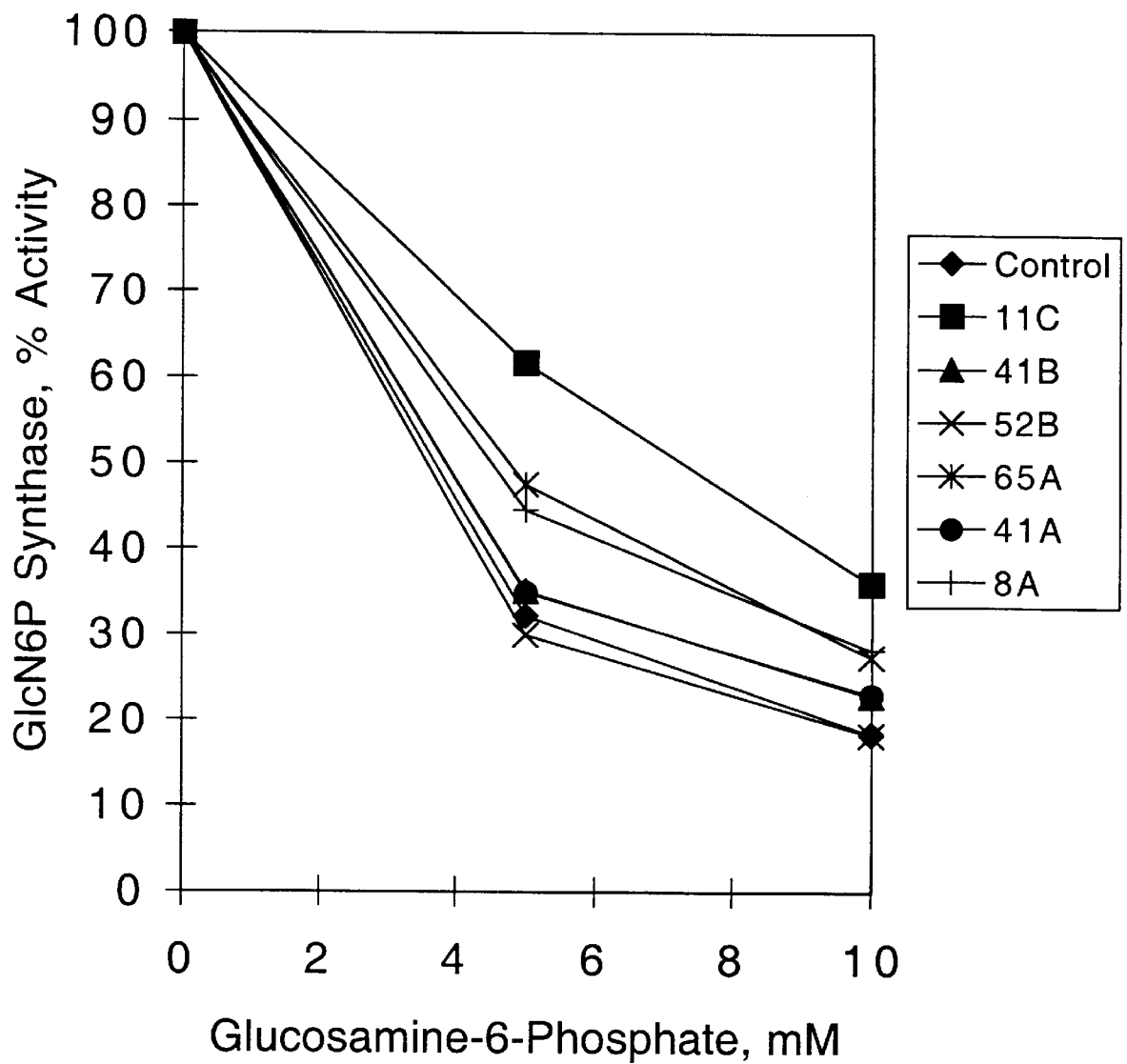
FIG. 6 is a line graph illustrating product inhibition of glucosamine-6-phosphate synthase activity in mutant glmS clones.

Enzyme assays performed with six of the plasmid-containing strains isolated as described above indicated that three of the strains were less sensitive to inhibition by glucosamine-6-phosphate than the enzyme from the control strain 7101-17(DE3)/pKLN23-28. The strains were grown overnight in LB broth containing 100 µg/mL ampicillin and 1 mM IPTC. Extracts prepared from cells harvested from those cultures were assayed for glucosamine-6-phosphate synthase using the spectrophotometric assay (described in Example 2) in the presence and absence of added glucosamine-6-phosphate. The mutant clones designated 11C, 65A, and 8A were significantly less sensitive to glucosamine-6-phosphate than the control strain (FIG. 6). Other mutants were not distinguishable from the control by this assay.

Example 6

The following example describes the construction and characterization of glucosamine production strains with mutations in glmS which result in reduced product inhibition.

Plasmid DNA isolated from clones 11C, 52B, and 8A described above were transferred to strain ATCC 47002, which had been used previously to integrate the cloned T7-glmS construct into the E. coli chromosome. Integration was readily accomplished using the methods described in Example 2, and the integrated DNA was transferred to strain 7101-17(DE3) by P1 transduction as described in Example 1. These procedures produced strains that have the same genotype as strain 2123-12 except for the presence of mutations in the glmS gene generated by PCR. These new mutant production strains were designated 2123-49, 2323-51, and 2123-54, respectively. A summary of the strain construction strategy is presented in FIG. 7.

Figure 8:
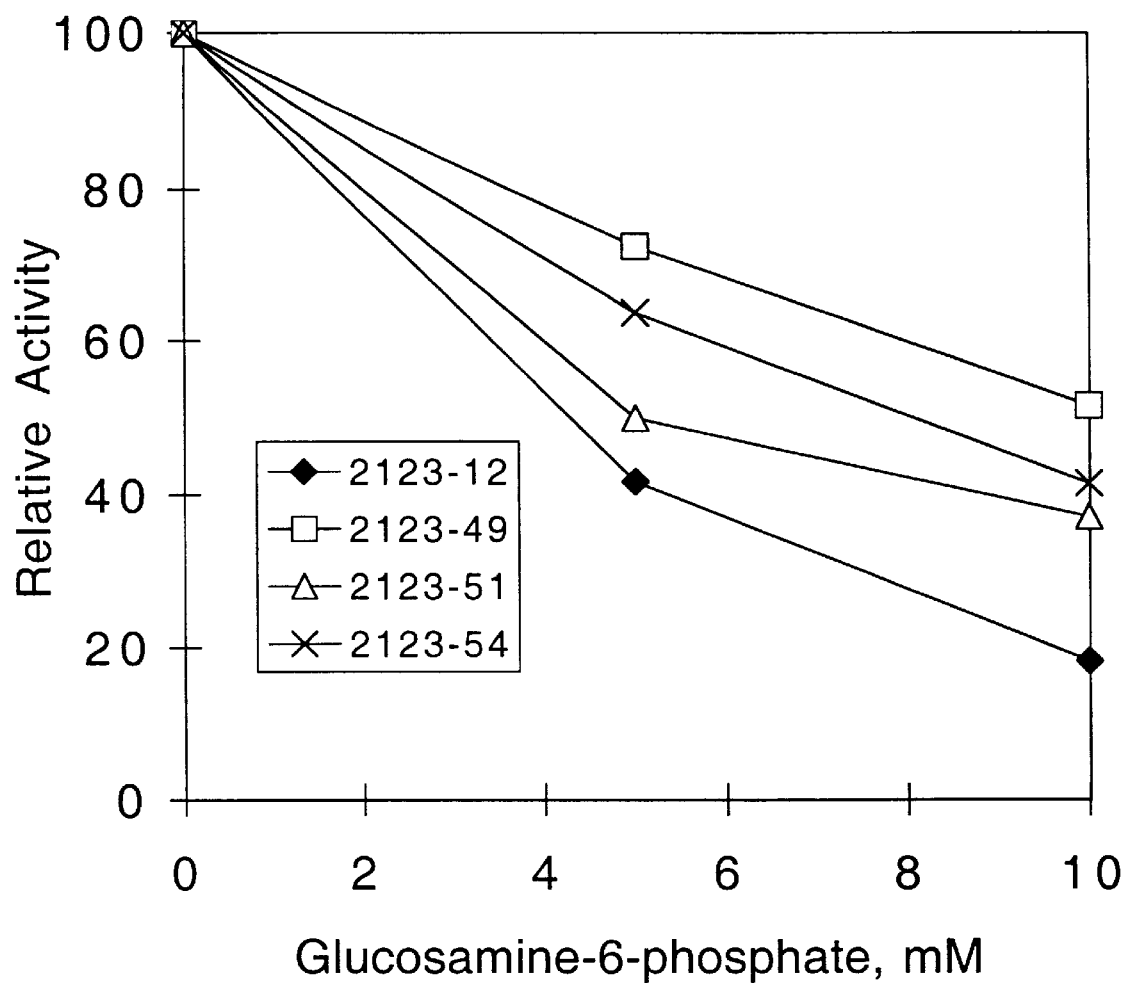
FIG. 8 is a line graph illustrating product inhibition of glucosamine-6-phosphate synthase in *Escherichia coli* strains with integrated mutant glmS genes.

Strains 2123-12, 2123-49, 2123-51, and 2123-54 were grown overnight in LB broth containing 1 mM IPTG. Extracts prepared from cells harvested from those cultures were assayed for glucosamine-6-phosphate synthase using the spectrophotometric assay described in Example 2 in the presence and absence of added glucosamine-6-phosphate. The results of these assays are shown in FIG. 8.

Figure 9:
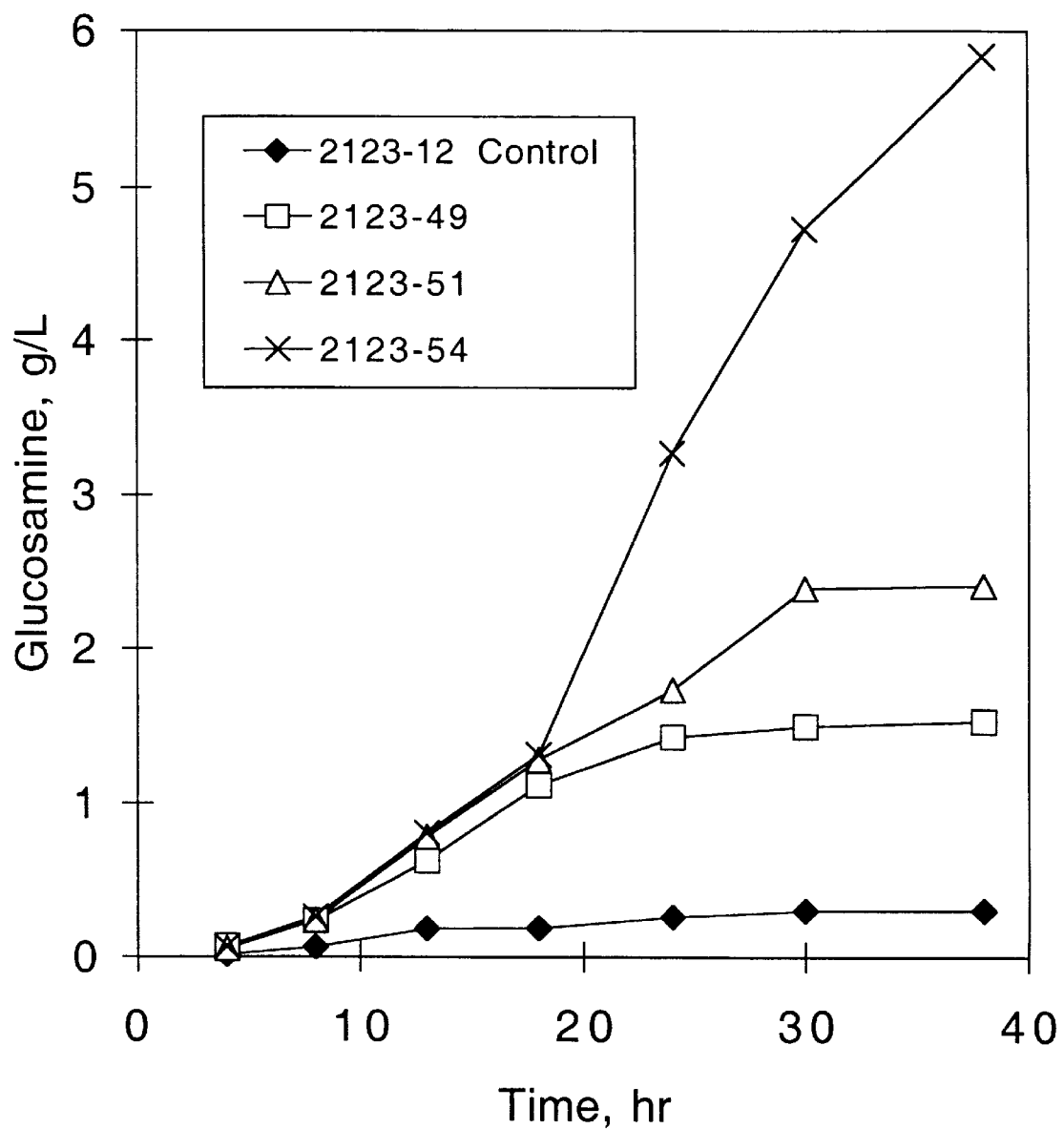
FIG. 9 is a line graph showing glucosamine production in mutant *Escherichia coli* strains with integrated mutant glmS genes.

Glucosamine production in these mutants was significantly elevated compared to that in 2123-12. When glucosamine production was assayed in shake flask cultures grown using the glucose and ammonium sulfate feeding protocol previously described in Example 4, when the cultures were grown to a cell density (measured as $O.D._{600}$) of about 14 (about 8.4 g/L by dry cell weight), strains 2123-49, 2123-51, and 2123-54 produced 1.5, 2.4, and 5.8 g/L glucosamine, respectively (FIG. 9) compared with 0.3 g/L for 2123-12.

Example 7

The following example describes the production of yet another strain with a mutation in glmS which results in reduced product inhibition.

An additional 6,344 colonies containing mutant plasmids generated by error-prone PCR as described in Example 5 were screened using the cross-feeding assay, also described in Example 5. Fifty four colonies resulted in larger halos than the rest of the colonies. DNA was isolated from all 54 colonies and strains isogenic to 2123-12 except for the mutations in glmS were constructed as described in Example 6.

Glucosamine production in most of these mutants was significantly elevated compared to strain 2123-12. Among the newly isolated mutants, the strain that produced the most glucosamine was a strain designated 2123-124. This strain produced 3.6 g/L of glucosamine when production was assayed in shake flasks using the glucose and ammonium sulfate feeding protocol described in Example 4 compared with 4.3 g/L for strain 2123-54 in a side-by-side experiment.

Example 8

The following example describes the sequencing of the cloned wild type glmS gene present in plasmid pKLN23-28. In addition, the sequences present in plasmids pKLN23-49, pKLN23-54, and pKLN23-124, containing the mutant glmS genes used to construct strains 2123-49, 2123-54, and 2123-124, respectively were sequenced and are described.

DNA sequencing reactions were performed using the Applied Biosystems (ABI) Prism Dye Terminator Cycle sequencing method with AmpliTaq DNA polymerase. The extended products were separated by gel electrophoresis on an ABI DNA sequencer 373A or 377. Sequences were analyzed using ABI Sequencing Analysis 3.0 software from ABI and Sequencher 3.1 from Gene Codes.

The primers used for sequencing were as follows:
PK-1: 5'-TGGATGAGCAGACGATGG-3' (SEQ ID NO:5)
PK-2: 5'-TCCGTCACAGGTATTTATTC-3' (SEQ ID NO:6)
PK-3: 5'-AGCTGCGTGGTGCGTAC-3' (SEQ ID NO:7)
PK-4: 5'-GGACCGTGTTTCAGTTCG-3' (SEQ ID NO:8)
PK-5A: 5'-GCCGTGGCGATCAGTAC-3' (SEQ ID NO:9)
PK-6A: 5'-GCCAATCACCAGCGGAC-3' (SEQ ID NO:10)
PK-7: 5'-ATGGTTTCCCGCTACTGG-3' (SEQ ID NO:11)
PK-8: 5'-GAACCAAGGTAACCCAGC-3' (SEQ ID NO:12)

The nucleotide sequence of plasmid pKLN23-28, containing the wild-type glmS gene, was determined to be a 7408 bp nucleic acid sequence represented herein as SEQ ID NO:13. The 2184 base pairs between positions 1130 and 3313 of SEQ ID NO:13 were determined using the primers described above. The nucleic acid molecule representing positions 1130–3313 of SEQ ID NO:13 is referred to herein as nglmS-28$_{2184}$ and is further identified as SEQ ID NO:14. nglmS-28$_{2184}$ was shown to include the SpeI and HinDIII sites used to construct the mutant plasmids as described in Example 5. The remaining DNA sequence of SEQ ID NO:13 is based on the known sequences of the vectors used for the construction of pKLN23-28. The same 2184 base pair region was sequenced in plasmids pKLN23-49, pKLN23-54, and pKLN23-124. It is noted that for the discussion of the mutant glmS genes of these plasmids (Table 5), the specific nucleotide position of mutations in the nucleotide sequence of the mutant glmS-containing plasmids will be described using SEQ ID NO:13 as a reference.

SEQ ID NOs:13 and 14 contain an open reading frame that encodes the glmS gene product (i.e., GlcN6P synthase enzyme) which is a nucleic acid molecule referred to herein as nglmS-28$_{1830}$, the nucleic acid sequence of which is represented by SEQ ID NO:15. SEQ ID NO:15 spans nucleotides 1253 to 3082 of SEQ ID NO:13, with an initiation codon spanning from nucleotides 1253–1255 and a termination codon spanning from nucleotides 3080–3082. SEQ ID NO:15 encodes a protein of 609 amino acids referred to herein as GlcN6P-S-28, the deduced amino acid sequence of which is represented herein as SEQ ID NO:16. It is noted that for the discussion of the mutant glmS gene products produced by the mutant strains described herein, specific mutations in the amino acid sequence of the mutant glmS gene products will be described using SEQ ID NO:16 as a reference.

The primers described above correspond to the following nucleotide positions of SEQ ID NO:13:
PK-1 (SEQ ID NO:5): positions 1087–1104 of SEQ ID NO:13;
PK-2 (SEQ ID NO:6): positions 3378–3359 of a nucleic acid sequence complementary to SEQ ID NO:13;
PK-3 (SEQ ID NO:7): positions 1707–1723 of SEQ ID NO:13;
PK-4 (SEQ ID NO:8): positions 2772–2755 of a nucleic acid sequence complementary to SEQ ID NO:13;
PK-5A (SEQ ID NO:9): positions 2667–2683 of SEQ ID NO:13;
PK-6A (SEQ ID NO:10): positions 1798–1782 of a nucleic acid sequence complementary to SEQ ID NO:13;

PK-7 (SEQ ID NO:11): positions 2177–2194 of SEQ ID NO:13;

PK-8 (SEQ ID NO:12): positions 2364–2347 of a nucleic acid sequence complementary to SEQ ID NO:13.

The nucleic acid sequence of nucleic acid molecule nglmS-28$_{1830}$ (SEQ ID NO:15, or positions 1253–3082 of SEQ ID NO:13) from pKLN23-28, differs from the published sequence (Walker, J. E, et al., 1984, "DNA sequence around the *Escherichia coli* unc operon", *Biochem. J.* 224:799–815) at positions 2509 and 2510 (with reference to SEQ ID NO:13). The nucleotides for pKLN23-28 at these positions as determined in this example were G and C, respectively, while those reported in the published sequence were C and G. Otherwise, the published and determined sequences of the glmS gene were identical. The sequences determined upstream and downstream from the glmS gene were those expected based on the known sequences of the vectors used for the construction of pKLN23-28 and the methods used to construct the plasmid.

The nucleotide sequences for the mutant glmS genes for plasmids pKLN23-49, pKLN23-54, and pKLN23-124 were determined as described above for pKLN23-28. Mutations were found in each of those plasmids. The mutations and the predicted amino acid changes in the corresponding mutant glmS gene products, as compared to the wild-type sequence determined for pKLN23-28 (SEQ ID NO:13) are summarized in Table 5.

TABLE 5

Mutations in glmS Genes of Glucosamine-Overproducing strains.

| Plasmid | Position* | Base Change | Amino Acid Change (Position**) |
|---|---|---|---|
| pKLN23-49 | 1263 | T to C | Ile to Thr (4) |
|  | 2067 | T to C | Ile to Thr (272) |
|  | 2600 | T to C | Ser to Pro (450) |
| pKLN23-54 | 1367 | G to A | Ala to Thr (39) |
|  | 2000 | C to T | Arg to Cys (250) |
|  | 2239 | T to C | Silent (329) |
|  | 2666 | G to A | Gly to Ser (472) |
|  | 3264 | A to G | Outside gene |
| pKLN23-124 | 1525 | T to C | Silent (91) |
|  | 2658 | T to C | Leu to Pro (469) |
|  | 3280 | G to A | Outside gene |

*Refers to nucleic acid position as indicated in the sequence of pKLN23-28 (SEQ ID NO:13)
**The glmS gene (nglmS-28$_{1830}$; SEQ ID NO:15) encodes a protein of 609 amino acids in length (SEQ ID NO:16); the methionine residue at position 1 is removed by a hydrolase.

Plasmid pKLN23-49 contains a 2184 bp nucleic acid molecule referred to herein as nglmS-49$_{2184}$, which comprises a mutant glmS gene. The nucleic acid sequence of nglmS-49$_{2184}$ is represented herein as SEQ ID NO:17. A nucleic acid molecule spanning from nucleotide 124 through 1953 of SEQ ID NO:17, referred to herein as nglmS-49$_{1830}$, represents an open reading frame encoding a mutant glucosamine-6-phosphate synthase of the present invention, with an initiation codon spanning from nucleotides 124–126 and a termination codon spanning from nucleotides 1951–1953 of SEQ ID NO:17. The nucleic acid sequence of nglmS-49$_{1830}$ is represented herein as SEQ ID NO:18. SEQ ID NO:18 encodes a mutant glucosamine-6-phosphate synthase protein of 609 amino acids referred to herein as GlcN6P-S-49, the deduced amino acid sequence of which is represented herein as SEQ ID NO:19. SEQ ID NO:17 has a nucleic acid sequence that is identical to positions 1130 through 3313 of SEQ ID NO:13 (i.e., SEQ ID NO:14), except for the mutations as indicated for plasmid pKLN23-49 in Table 5. SEQ ID No:18 has a nucleic acid sequence that is identical to positions 1253 through 3082 of SEQ ID NO:13 (i.e., SEQ ID NO:15), except for the mutations as indicated for plasmid pKLN23-49 in Table 5.

Plasmid pKLN23-54 contains a 2184 bp nucleic acid molecule referred to herein as nglmS-54$_{2184}$, which comprises a mutant glmS gene. The nucleic acid sequence of nglmS-54$_{2184}$ is represented herein as SEQ ID NO:20. A nucleic acid molecule spanning from nucleotide 124 through 1953 of SEQ ID NO:20, referred to herein as nglmS-54$_{1830}$, represents an open reading frame encoding a mutant glucosamine-6-phosphate synthase of the present invention, with an initiation codon spanning from nucleotides 124–126 and a termination codon spanning from nucleotides 1951–1953 of SEQ ID NO:20. The nucleic acid sequence of nglmS-54$_{830}$ is represented herein as SEQ ID NO:21. SEQ ID NO:21 encodes a mutant glucosamine-6-phosphate synthase protein of 609 amino acids referred to herein as GlcN6P-S-54, the deduced amino acid sequence of which is represented herein as SEQ ID NO:22. SEQ ID NO:20 has a nucleic acid sequence that is identical to positions 1130 through 3313 of SEQ ID NO:13 (i.e., SEQ ID NO:14), except for the mutations as indicated for plasmid pKLN23-54 in Table 5. SEQ ID NO:21 has a nucleic acid sequence that is identical to positions 1253 through 3082 of SEQ ID NO:13 (i.e., SEQ ID NO:15), except for the mutations as indicated for plasmid pKLN23-54 in Table 5.

Plasmid pKLN23-124 contains a 2184 bp nucleic acid molecule referred to herein as nglmS-124$_{2184}$, which comprises a mutant glmS gene. The nucleic acid sequence of nglmS-124$_{2184}$ is represented herein as SEQ ID NO:23. A nucleic acid molecule spanning from nucleotide 124 through 1953 of SEQ ID NO:23, referred to herein as nglmS-124$_{1830}$, represents an open reading frame encoding a mutant glucosamine-6-phosphate synthase of the present invention, with an initiation codon spanning from nucleotides 124–126 and a termination codon spanning from nucleotides 1951–1953 of SEQ ID NO:23. The nucleic acid sequence of nglmS-124$_{1830}$ is represented herein as SEQ ID NO:24. SEQ ID NO:24 encodes a mutant glucosamine-6-phosphate synthase protein of 609 amino acids referred to herein as GlcN6P-S-124, the deduced amino acid sequence of which is represented herein as SEQ ID NO:25. SEQ ID NO:23 has a nucleic acid sequence that is identical to positions 1130 through 3313 of SEQ ID NO:13 (i.e., SEQ ID NO:14), except for the mutations as indicated for plasmid pKLN23-124 in Table 5. SEQ ID NO:24 has a nucleic acid sequence that is identical to positions 1253 through 3082 of SEQ ID NO:13 (i.e., SEQ ID NO:15), except for the mutations as indicated for plasmid pKLN23-124 in Table 5.

To verify that the same mutations were present in the strains into which the mutant glmS genes were integrated into the chromosome, PCR products were generated from genomic DNA isolated from strains 2123-49, 2123-54, and 2123-124. For PCR amplification, the primers listed in Example 3 for the mutagenesis of the gene (SEQ ID NO:3 and SEQ ID NO:4) were used. PCR reactions were carried out in 50 µL reactions consisting of 20 mM Tris.HCl (pH 8.8), 10 mM KCl, 10 mM (NH$_4$)$_2$SO$_4$, 20 mM MgSO$_4$, 0.1% Triton X-100, 0.1 mg/mL nuclease-free bovine serum albumin, 0.05 mM each deoxynucleotide triphosphate, 2 µM each primer, 1.25 U cloned Pfu DNA polymerase (Stratagene), and 360 ng of genomic DNA. The complete reactions were placed in a RoboCycler Gradient 96 Temperature Cycler (Stratagene). After 3 minutes at 94° C., the following three steps were repeated for 30 cycles: (1) 30 seconds at 94° C.; (2) 30 seconds at 47° C.; and (3) 2 minutes at 72°. This was followed with a 7 minute incubation at 72° C.

The resulting DNA contained the expected amplification product in addition to extraneous products. The product containing the glmS gene was purified using a QIAquick PCR purification kit, followed by electrophoresis of the purified product on an agarose gel, isolation of the correct band using a QIAquick gel extraction kit, and reamplification using this isolated DNA as a template. The reactions with the isolated DNA were amplified in a similar fashion as the original amplification described above, except that 40 ng of DNA was used as template, and only 20 cycles of amplification were performed. The product from this second amplification reaction was recovered as described above.

The presence of mutations in the genomic DNA was verified using primers specific for the DNA regions containing the mutations identified in the plasmids. For 2123-49, these included primers PK-1 (SEQ ID NO:5), PK-3 (SEQ ID NO:7), PK-4 (SEQ ID NO:8), and PK-5A (SEQ ID NO:9). For 2123-124, primers PK-1 (SEQ ID NO:5), PK-4 (SEQ ID NO:8) and PK-5 (SEQ ID NO:9) were used. For 2122-54, the entire PCR product was sequenced using all eight primers described. earlier (SEQ ID NOs:5–12). Sequencing of the PCR products confirmed the presence of the mutations identified from the plasmids and listed in Table 5.

Example 9

This example describes the construction of strains containing a mutant glmS gene encoding a product containing only the glycine to serine alteration at position 472 (SEQ ID NO:22) from strain 2123-54.

As indicated in Table 5, the only amino acid change in the GlcN6P synthase enzyme for strain 2123-124 (GlcN6P-S-124) is a leucine to proline alteration at position 469 (SEQ ID NO:25), unambiguously defining this mutation as being responsible for the overproductable or of glucosamine by strain 2123-124. This would suggest the possibility that the glycine to serine alteration at position 472 (gly→ser472; SEQ ID NO:22) of GlcN6P-S-54 in strain 2123-54 was likewise responsible for the glucosamine overproduction phenotype for this strain. In an effort to demonstrate this, the alteration was isolated away from the other two amino acid alterations in the GlcN6P-S-54 amino acid sequence (SEQ ID NO:22) of strain 2123-54 (i.e., Ala→Thr39 and Arg→Cys250) by digesting plasmid pKLN23-54 with EcoRI and HinDIII. These enzymes each have unique cleavage sites on the plagmid and cut at positions 2241 and 3305, respectively (positions indicated with respect to the equivalent positions in SEQ ID NO:13 for pKLN23-28), resulting in fragments of 1064 and 6344 base pairs. The smaller fragment contains mutations in which the gly→ser472 alteration is the only amino acid change In this portion of GlcN6P-S-54. This smaller fragment was ligated to the corresponding larger fragment from pKLN23-28 containing the wild type glmS gene.

Two plasmids resulting from this ligation were designated pKLN23-149 and pKLN23-151. Sequencing the DNA from these plasmids using primers PK-1 (SEQ ID NO:5), PK-3 (SEQ ID NO:7), and PK-4 (SEQ ID NO:8) verified that these plasmids contained the mutation at position 2666 present in plasmid pKLN23-54 but not the mutations at positions 1367 and 2000 (Table 5 with reference to SEQ ID NO:13).

The nucleic acid sequence of the 2184 base pairs between positions 1130 and 3313 of plasmid pKLN23-149 (these positions being determined relative to the equivalent positions in SEQ ID NO:13) are referred to herein as nucleic acid molecule nglmS-149$_{2184}$, the nucleic acid sequence of which is represented by SEQ ID NO:26. SEQ ID NO:26 contains a nucleic acid sequence spanning nucleotides 124 through 1953, referred to herein as nglmS-149$_{1830}$, which represents an open reading frame encoding a mutant glucosamine-6-phosphate synthase of the present invention, with an initiation codon spanning from nucleotides 124–126 and a termination codon spanning from nucleotides 1951–1953 of SEQ ID NO:26. The nucleic acid sequence of nglmS-149$_{1830}$ is represented herein as SEQ ID NO:27. SEQ ID NO:27 encodes a mutant glucosamine-6-phosphate synthase protein of 609 amino acids referred to herein as GlcN6P-S-149, the deduced amino acid sequence of which is represented herein as SEQ ID NO:28.

The nucleic acid sequence of the 2184 base pairs between positions 1130 and 3313 of plasmid pKLN23-151 (these positions being determined relative to the equivalent positions in SEQ ID NO:13) are referred to herein as nucleic acid molecule nglmS-151$_{2184}$, the nucleic acid sequence of which is represented by SEQ ID NO:29. SEQ ID NO:29 contains a nucleic acid sequence spanning nucleotides 124 to 1953, referred to herein as nglmS-151$_{1830}$, which represents an open reading frame encoding a mutant glucosamine-6-phosphate synthase of the present invention, with an initiation codon spanning from nucleotides 124–126 and a termination codon spanning from nucleotides 1951–1953 of SEQ ID NO:29. The nucleic acid sequence of nglmS-151$_{1830}$ is represented herein as SEQ ID NO:30. SEQ ID NO:30 encodes a mutant glucosamine-6-phosphate synthase protein of 609 amino acids referred to herein as GlcN6P-S-151, the deduced amino acid sequence of which is represented herein as SEQ ID NO:31.

Figure 7:
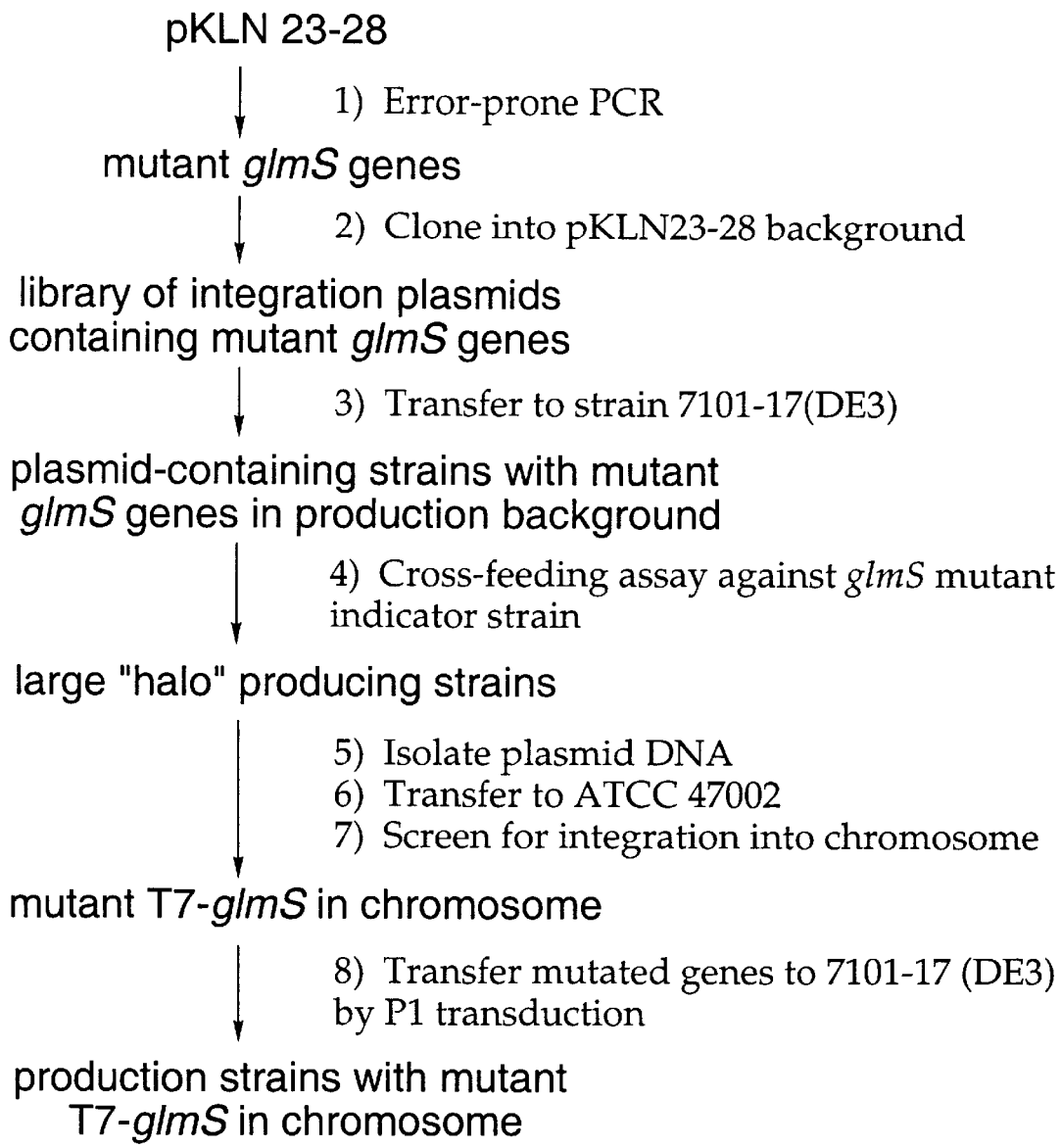
FIG. 7 is a schematic representation of the strategy for constructions of *Escherichia coli* strains containing mutant glmS genes.

Strains isogenic to strain 2123-12 except for mutations conferring the gly→ser472 alteration were constructed using the scheme indicated in FIG. 7. Strains 2123-149 and 2123-151 were generated from plasmids pKLN23-149 and pKLN23-151, respectively. The presence of the mutation at position 2666 (SEQ ID NO:13) and the absence of mutations at positions 1367 and 2000 were verified by sequencing of PCR products from genomic DNA of these strains using the methods described in Example 8.

Example 10

This example compares properties of GlcN6P synthase enzymes from strains 2122-12, 2123-49, 2123-54, 2122-124, 2123-149, and 2123-151.

Strains 2123-12, 2123-49, 2123-54, 2123-124, 2123-149, and 2123-151, described in the examples above, were grown overnight in LB broth at 37° C. then transferred to fresh LB broth. Cultures were grown to an absorbance at 600 nm of 0.8 to 0.9, then induced for GlcN6P synthase production by the addition of 1 mM IPTG. The cultures were grown for an additional three hours at 37° and harvested. Extracts were prepared from cells harvested from those cultures as described in Example 2 and were assayed for glucosamine-6-phosphate synthase using the spectrophotometric assay as described in Example 2 except that a fructose-6-phosphate concentration of 20 mM was used. The enzyme was assayed in the presence and absence of added glucosamine-6-phosphate. In the absence of glucosamine-6-phosphate, the specific activities measured for these enzymes were similar except for that from strain 2123-124. The data from Table 6 suggests that the latter strain encodes a less active variant of the enzyme.

TABLE 6

Specific Activities of GlcN6P Synthase from Glucosamine-Producing Strains

| Strain | Specific Activity, $\mu$mol min$^{-1}$ mg$^{-1}$ |
| --- | --- |
| 2123-12 | 0.385 |
| 2123-49 | 0.375 |
| 2123-54 | 0.416 |
| 2123-124 | 0.0076 |
| 2123-149 | 0.494 |
| 2123-151 | 0.515 |

Figure 10:
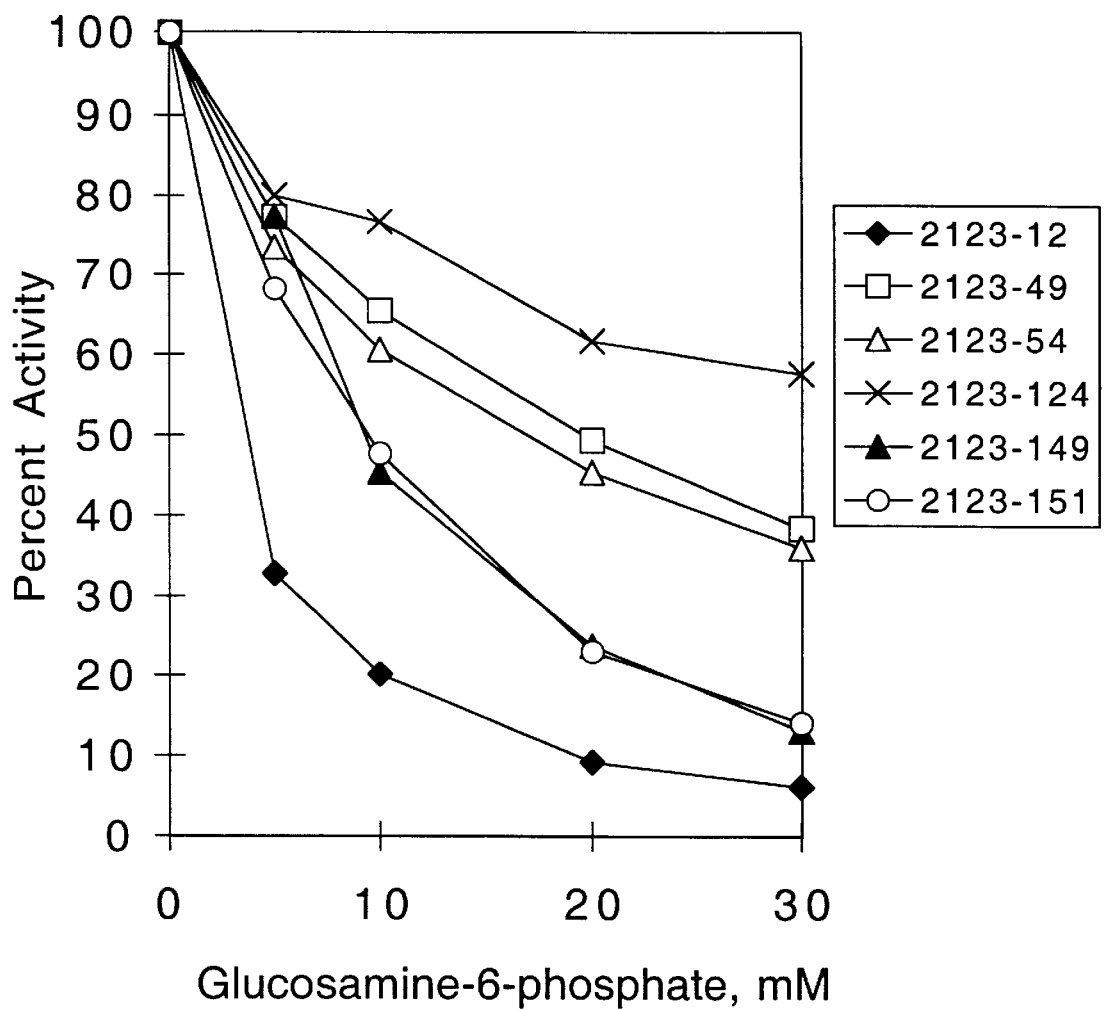
FIG. 10 is a line graph showing inhibition of glucosamine-6-phosphate synthase in glucosamine-producing strains.
Figure 11A:
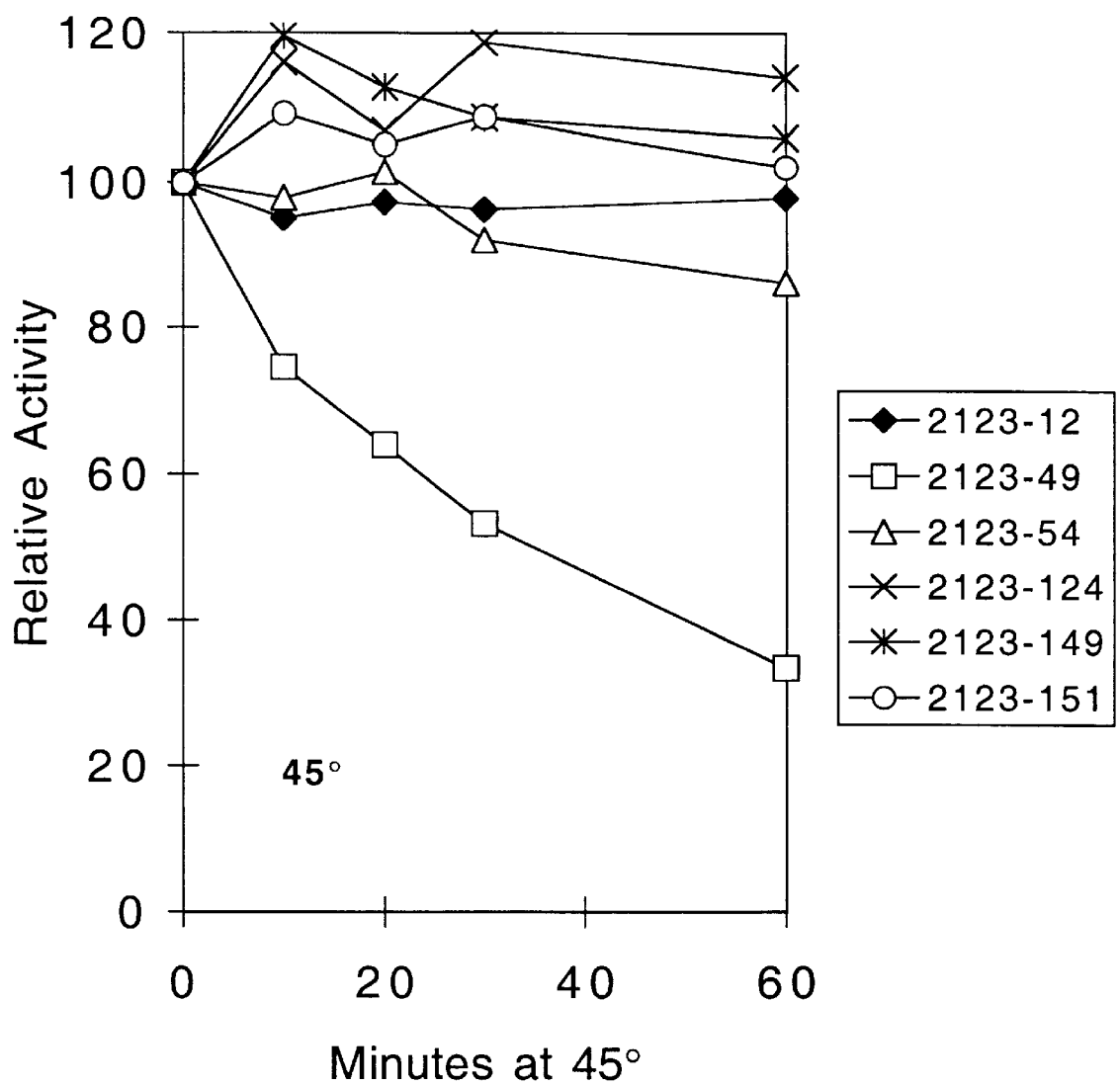
FIG. 11A is a line graph showing the thermal stability at 45° C. of glucosamine-6-phosphate synthase in glucosamine-producing strains.
Figure 11B:
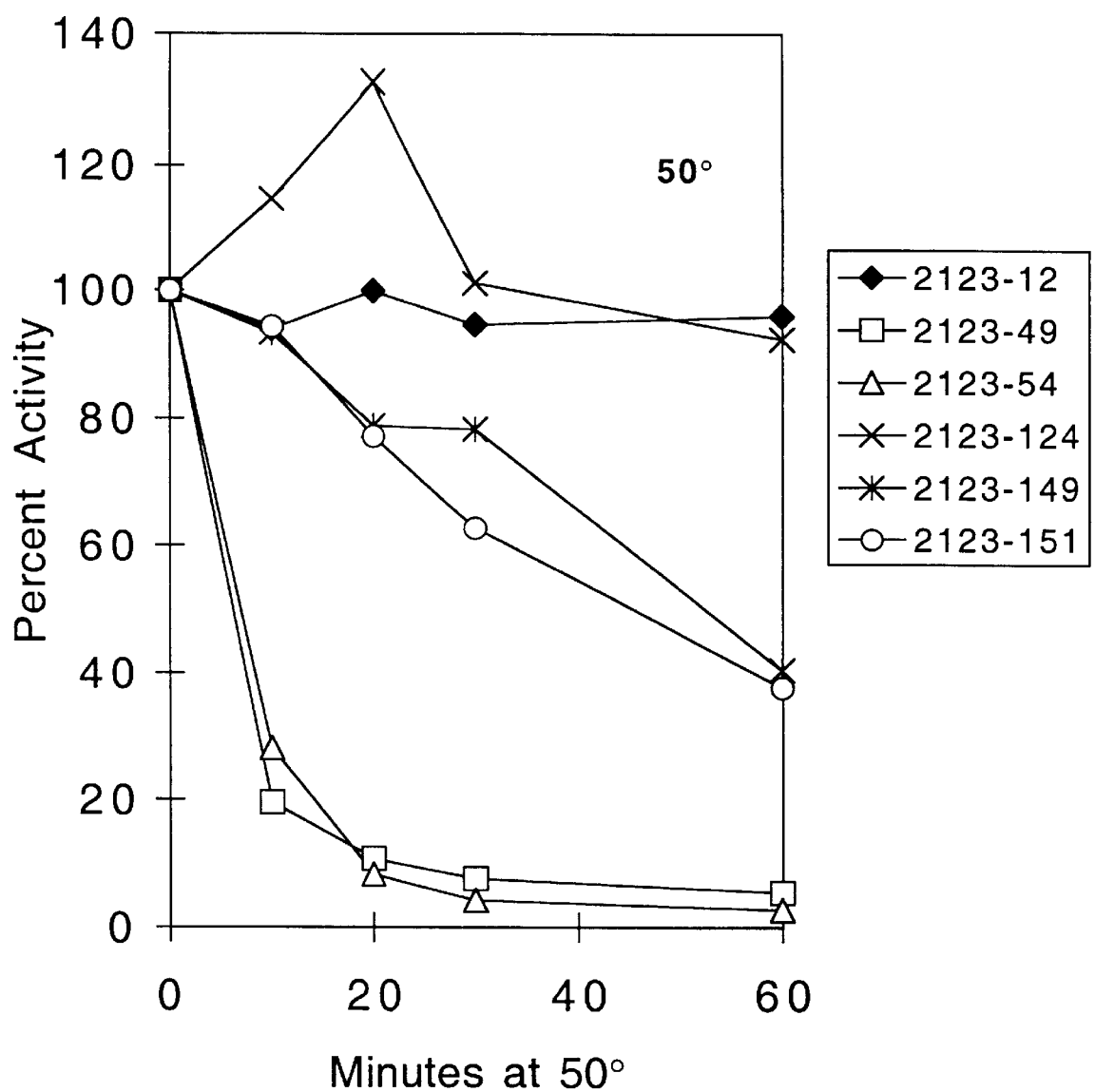
FIG. 11B is a line graph illustrating the thermal stability at 50° C. of glucosamine-6-phosphate synthase in glucosamine-producing strains.

FIG. 10 shows that the GlcN6P synthase enzymes from strains 2123-49, 2123-54, and 2123-124 are significantly less inhibited by GlcN6P than the enzyme from strain 2123-12. Enzymes from strains 2123-149 and 2123-151 are slightly less inhibited by GlcN6P than the enzyme from 2123-12. Thermal stability of the enzymes was also examined using these extracts. The extracts were incubated at 45° C. (FIG. 11A) or 50° C. (FIG. 11B) for various periods then assayed using the spectrophotometric assay. FIGS. 11A and 11B show that the enzymes from 2123-49 and 2123-54 are much less stable than the wild type enzyme from strain 2123-12. The enzyme from strain 2123-124 is comparable in stability to the wild type enzyme, and the enzymes from 2123-149 and 2123-151 are slightly less stable under the incubation conditions described here.

Example 11

The following example illustrates the effects of isopropylthio-$\beta$-D-galactoside (IPTG) concentration and temperature on glucosamine production.

Figure 12:
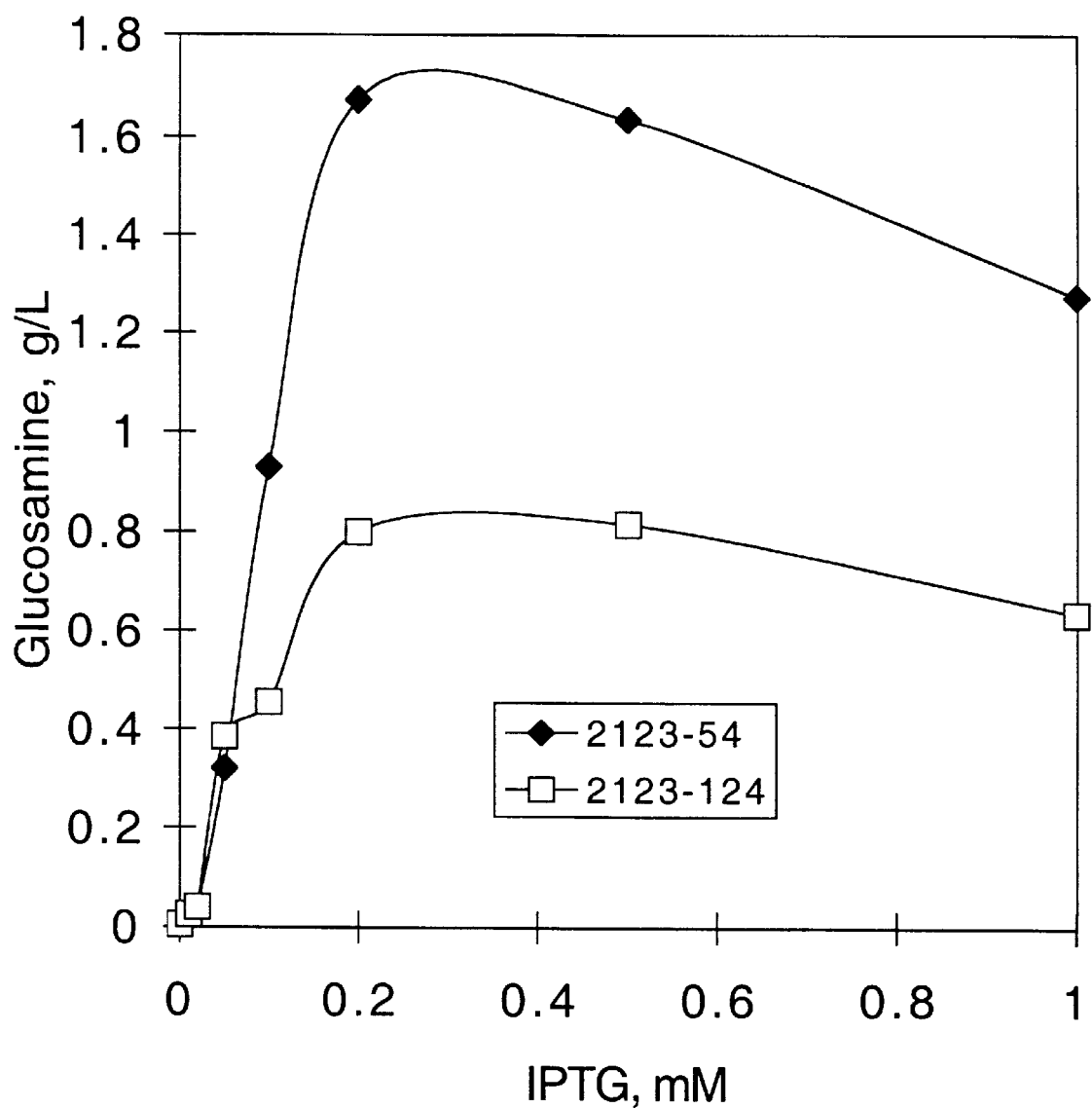
FIG. 12 is a line graph showing the effect of IPTG concentration on glucosamine production.

Cultures of strains 2123-54 and 2123-124 were grown for 20 hours at 37° C. on M9A medium (14 g/L K$_2$HPO$_4$, 16 g/L KH$_2$PO$_4$, 1 g/L Na$_3$Citrate.2H$_2$O, 5 g/L (NH$_4$)$_2$SO$_4$, pH 7.0) supplemented with 20 g/L glucose, 1 mM MgSO$_4$, 0.1 mM CaCl$_2$, and varying amounts of IPTG. At the end of the growth period, a sample was taken and the glucosamine concentration in the culture supernatant was assayed using the Elson-Morgan assay described in Example 2. The results shown in FIG. 12 indicate that the optimum IPTG concentration for production is about 0.2 mM.

Figure 13:
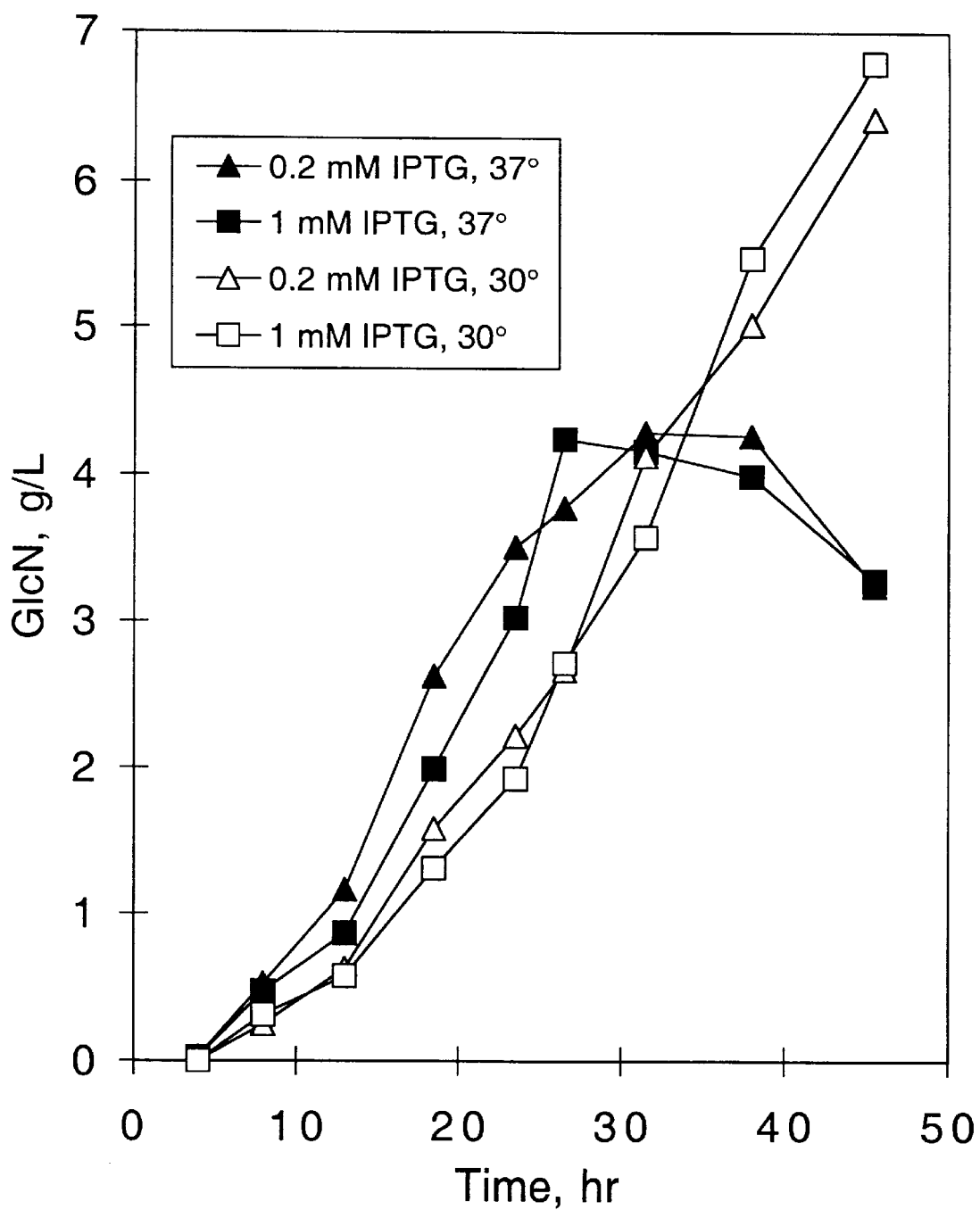
FIG. 13 is a line graph demonstrating the effects of IPTG concentration and temperature on glucosamine production.
Figure 14A:
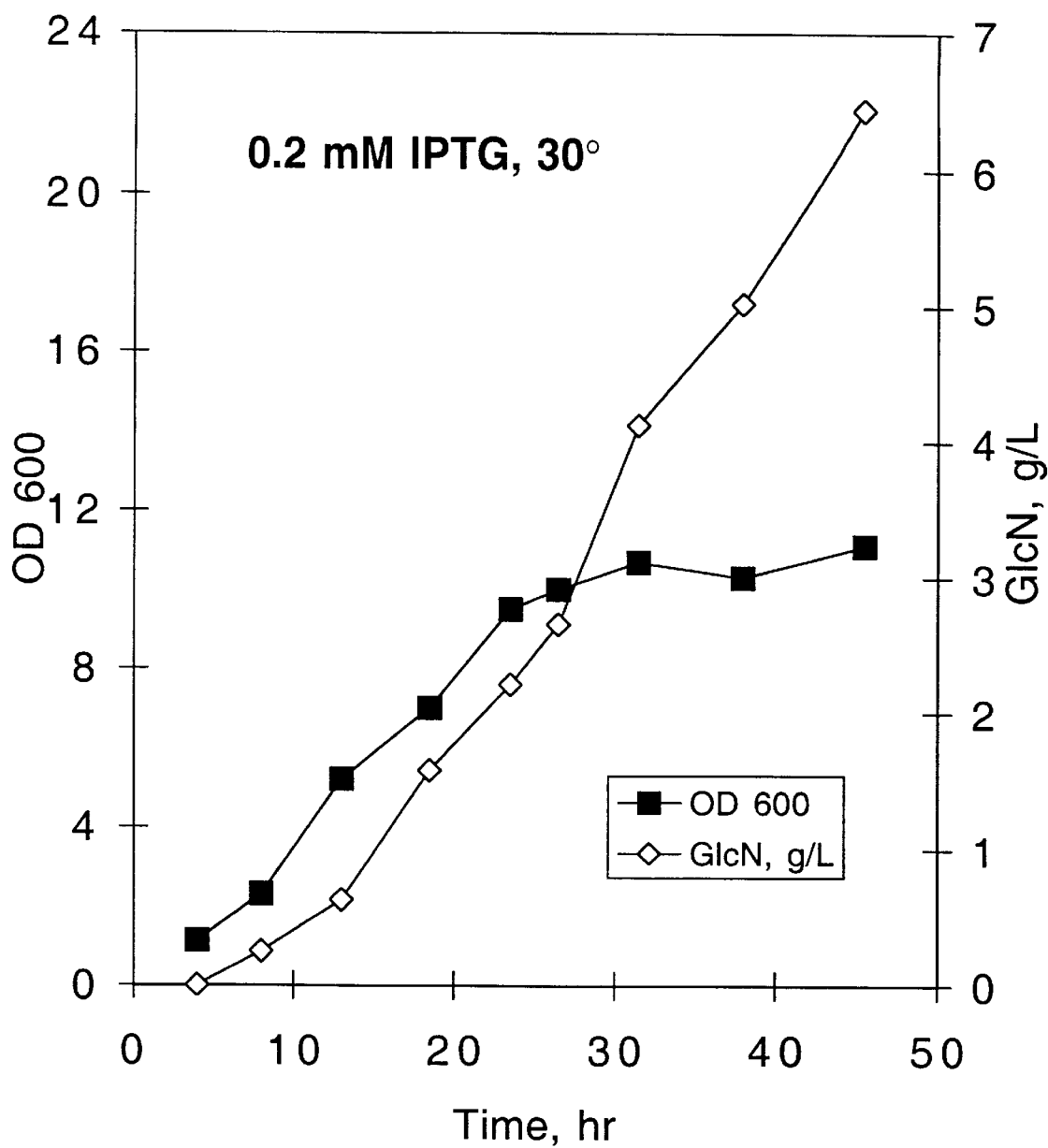
FIG. 14A is a line graph illustrating growth and glucosamine production by glucosamine-producing strain 2123-54 at 30° C.
Figure 14B:
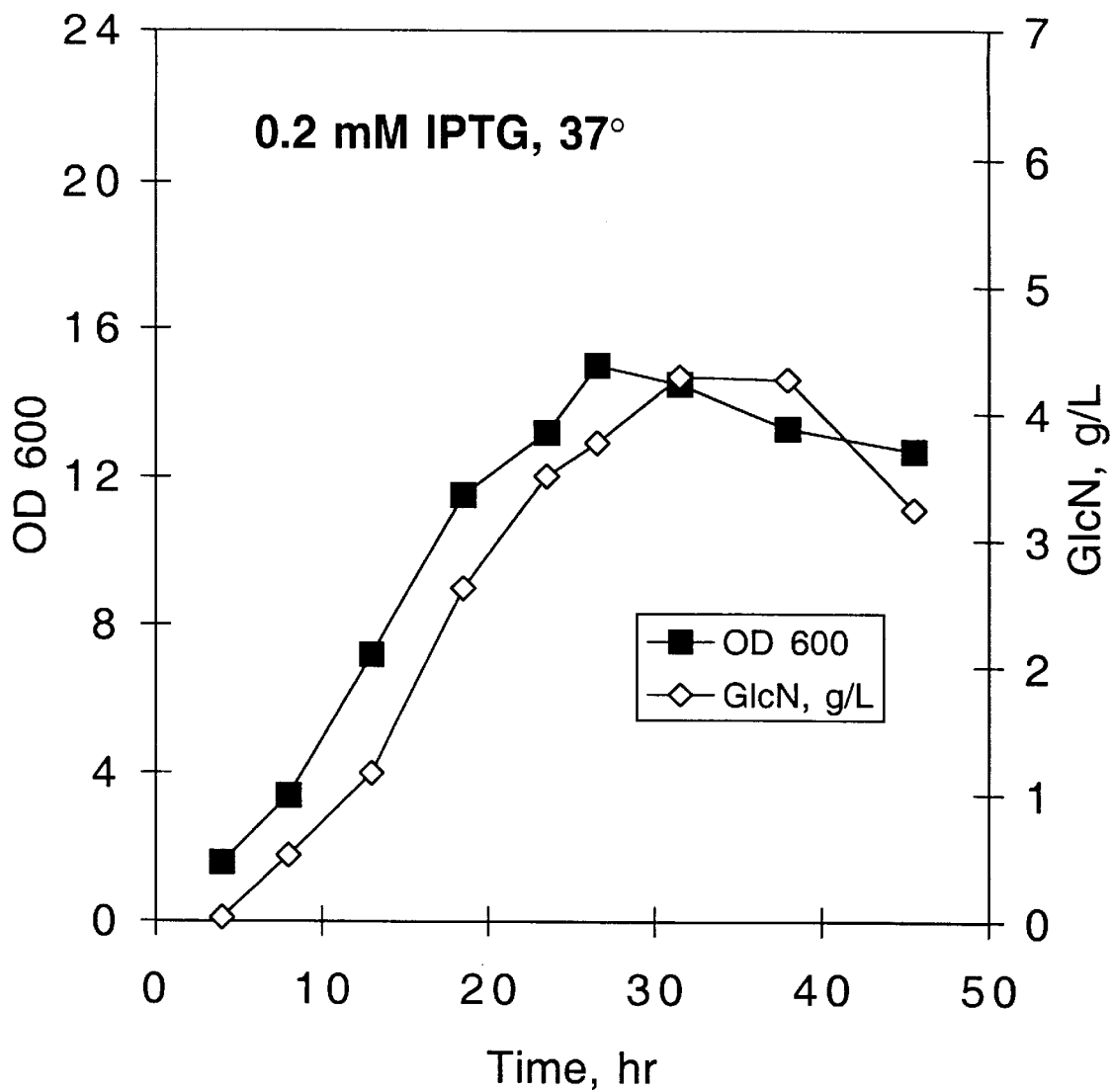
FIG. 14B is a line graph illustrating growth and glucosamine production by glucosamine-producing strain 2123-54 at 37° C.

Subsequently, strain 2123-54 was grown in the same medium as described above in shake flasks with either 0.2 or 1 mM IPTC and at 30° C. or 37° C. These flask cultures were also fed glucose and ammonium sulfate as described in Example 4. At various intervals, samples were taken and the glucosamine concentrations in culture supernatants were assayed using the Elson-Morgan assay described in Example 2. FIG. 13 shows that under the conditions of this experiment, there was little difference in glucosamine production associated with the differences in IPTG concentration. However, growth at 30° C. resulted in higher glucosamine production than did growth at 37° C. Results shown in FIGS. 14A and 14B further indicated that at 30° C. (FIG. 14A), glucosamine production continued after growth had ceased, while at 37° C. (FIG. 14B), growth and glucosamine production occurred in concert.

Figure 15A:
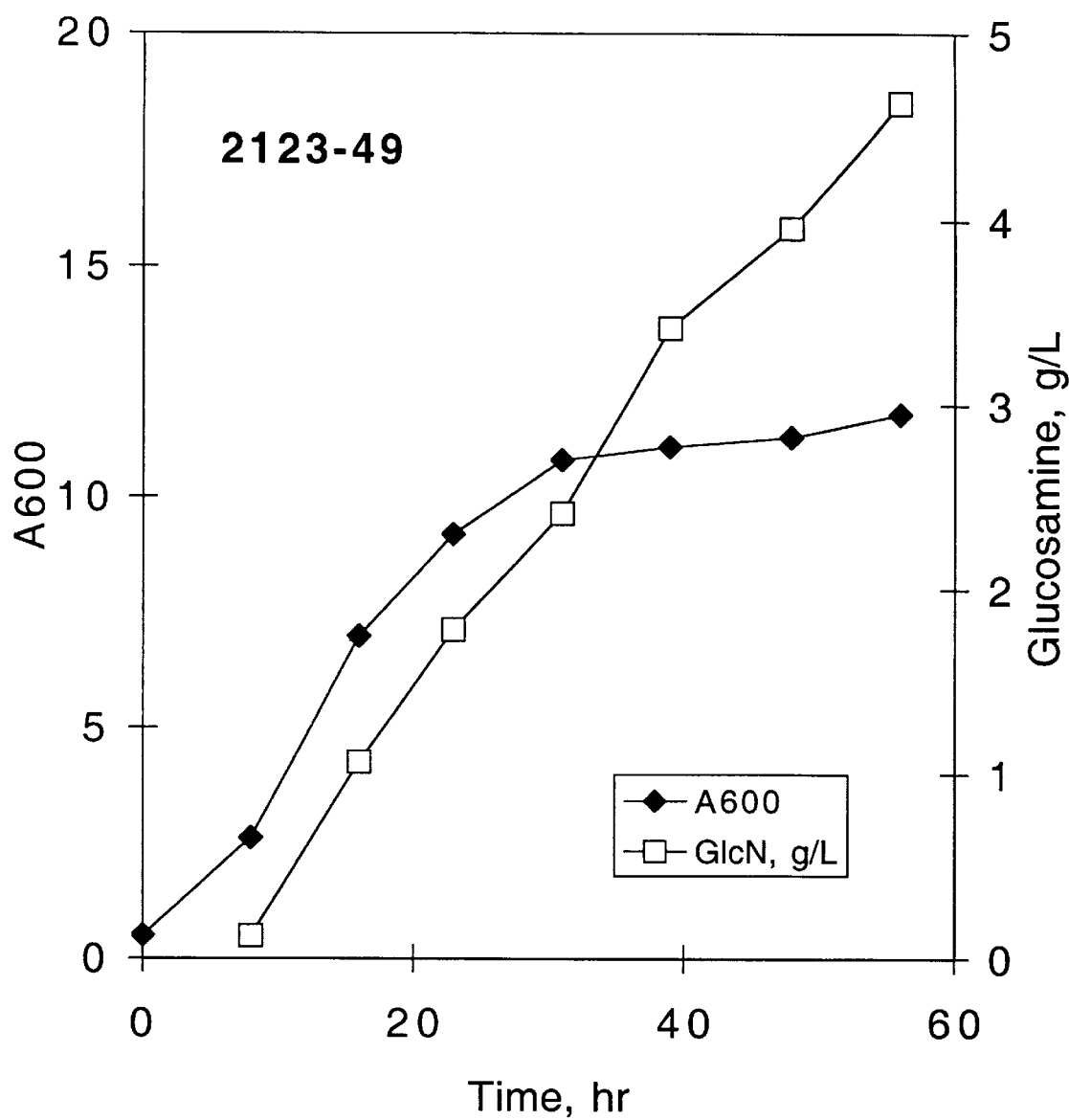
FIG. 15A is a line graph showing glucosamine production by strain 2123-49 at 30° C.
Figure 15B:
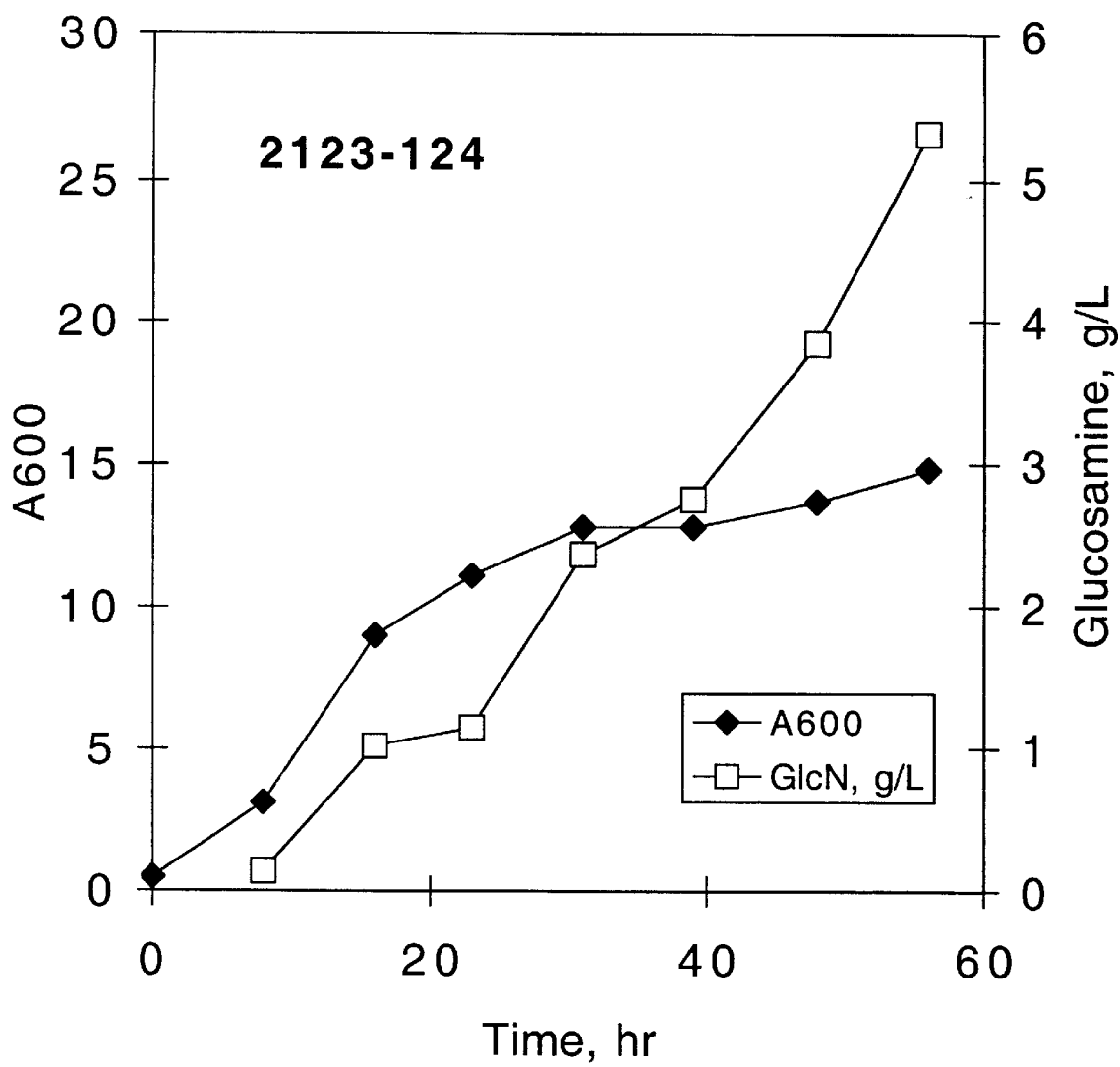
FIG. 15B is a line graph showing glucosamine production by strain 2123-124 at 30° C.

When strains 2123-49 and 2123-124 were grown with 0.2 mM IPTC at 30° C., glucosamine production also occurred after growth had ceased, as shown in FIGS. 15A (2123-49) and 15B (2123-124). As observed at 37° C., the highest concentrations of glucosamine were obtained with strain 2123-54, followed by 2123-124 and 2123-49. Also tested were strains 2123-149 and 2123-151 which produced negligibly higher concentrations of glucosamine than did 2123-12 (Table 7).

TABLE 7

Production of Glucosamine at 30°

| Strain | Maximum Glucosamine Production, g/L |
| --- | --- |
| 2123-12 | 0.3 |
| 2123-49 | 4.6 |
| 2123-54 | 7.2 |
| 2123-124 | 5.3 |
| 2123-149 | 0.6 |
| 2123-151 | 0.6 |

Example 12

The following example illustrates that glucosamine can be produced at higher concentrations in fermenter cultures of strain 2123-54 as compared to shake flasks. This example also illustrates that in fermentors, strain 2123-54 produces more glucosamine at 30° C. than at 37° C.

Fermentation cultures of strain 2123-54 were cultivated in the medium shown in Table 8. Fermentations were run using NaOH for pH control to pH 6.7 and were fed a mixture of 33% glucose, 8% ammonium sulfate. Aeration and agitation were adjusted to maintain a dissolved oxygen concentration of greater than 20% of air saturation.

TABLE 8

Fermentation Medium

| Component | Amount, g/L |
| --- | --- |
| K$_2$HPO$_4$ | 14 |
| KH$_2$PO$_4$ | 16 |
| Na$_3$Citrate 2H$_2$O | 1 |
| (NH$_4$)$_2$SO$_4$ | 5 |
| MgSO$_4$ | 0.12 |
| CaCl$_2$ | 0.011 |
| Mazu 204 Antifoam | 0.5 mL/L |
| IPTG | 0.048 |
| Glucose | 20 |
| Trace Metals | * |

*Trace metal composition is 0.7 mg/L CoCl$_2$, 1.7 mg/L H$_3$BO$_3$ 0.6 mg/L CUCl$_2$2H$_2$O, 10.5 mg/L FeCl$_3$.6H$_2$O, 12 mg/L MnCl$_2$.4H$_2$O, 1.5 mg/L Na$_2$Mo$_4$.2H$_2$O, 1.5 mg/L ZnCl$_2$.

In the following experiment, three fermentations were run in one-liter vessels containing an initial volume of 600 mL. Variables tested were as follows.

Fermenter #1: The mixture of 33% glucose and 8% ammonium sulfate was fed at such a rate that no glucose accumulated in the fermenter. Growth was at 37°.

Fermenter #2: As with fermentation #1 except that growth was at 30°.

Fermenter #3: As with fermentation #2 except that the feed rate was increased to maintain a constant glucose concentration in the fermenter of 5 to 10 g/L.

Figure 16A:
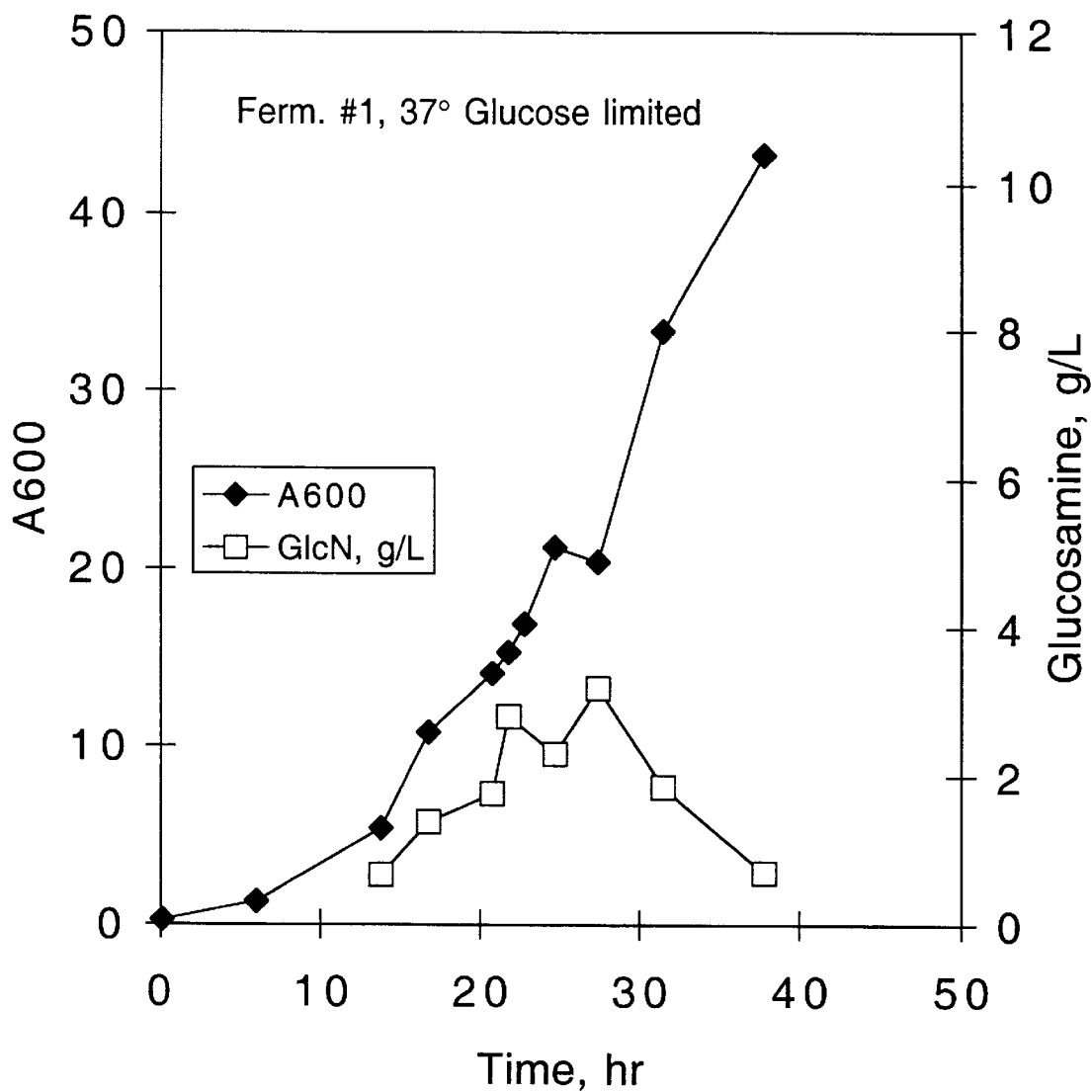
FIG. 16A is a line graph illustrating glucosamine production by a glucosamine-producing strain in a glucose limited fermenter at 37° C.
Figure 16B:
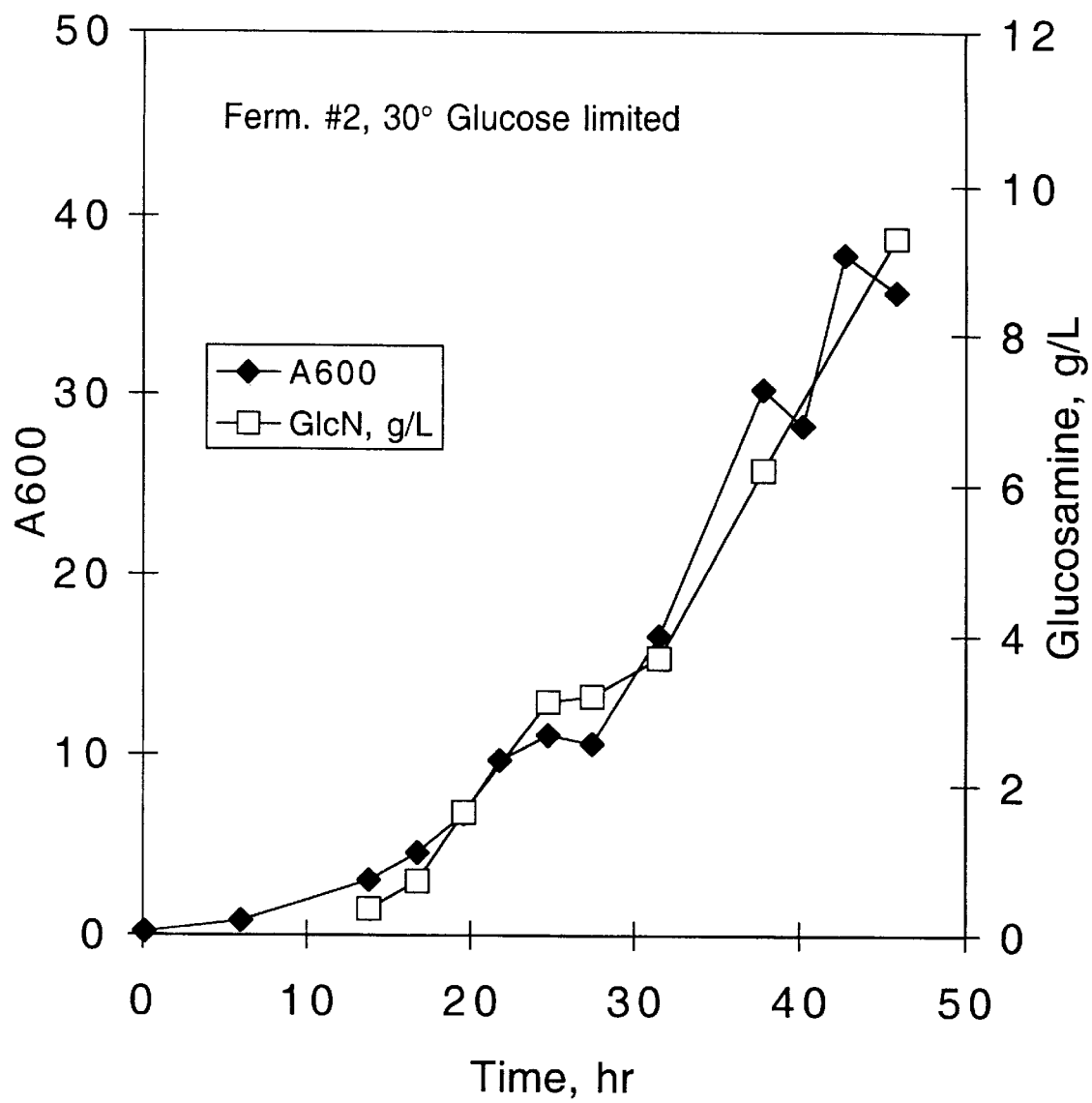
FIG. 16B is a line graph illustrating glucosamine production by a glucosamine-producing strain in a glucose limited fermenter at 30° C.
Figure 16C:
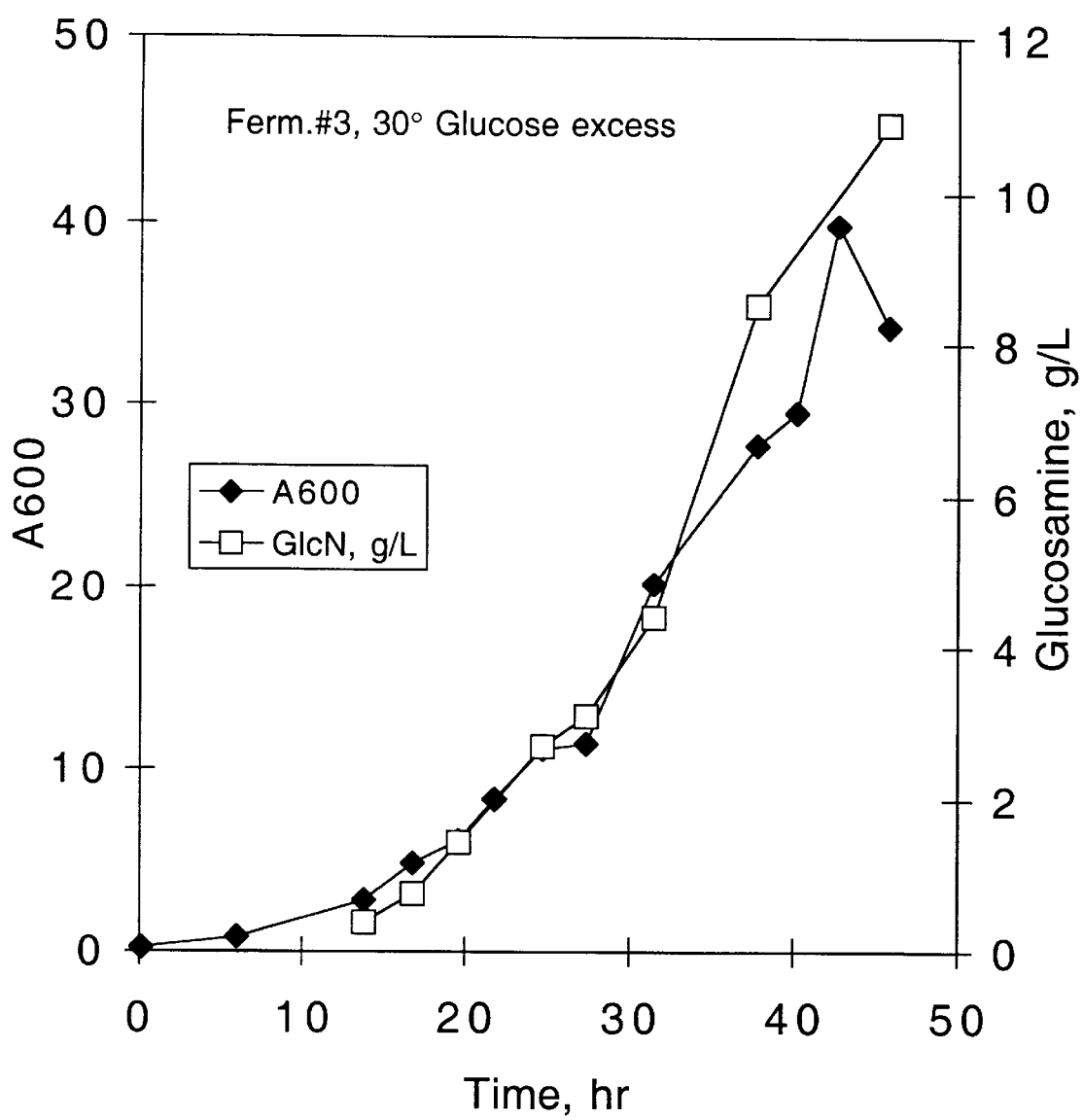
FIG. 16C is a line graph illustrating glucosamine production by a glucosamine-producing strain in a glucose excess fermenter at 30° C.

Results from these fermentations are shown in FIGS. 16A, 16B and 16C. Comparison of the results from fermentors 1 (FIG. 16A) and 2 (FIG. 16B) shows that glucosamine titers are markedly higher at 30° C. than they are at 37° C., as observed in shake flasks. The maximum glucosamine concentration observed was in the glucose-excess fermenter 3 grown at 30° C. (FIG. 16C), at 10.9 g/L. At 30° C., growth and glucosamine concentration appeared to coincide, and there appeared to be a slight advantage to growth under glucose-excess. In subsequent fermentation experiments, run under conditions similar to fermenter #3, glucosamine concentrations in excess of 12 g/L have been obtained (data not shown).

In summary, the present inventors have described herein the use of metabolic engineering to create the first glucosamine overproducing strains of *E. coli*. The concept, proven here, will be generally applicable to any microorganism having a pathway for the production of amino sugars, or to any recombinant microorganism into which a pathway for the production of amino sugars has been introduced. In addition to the present strategy for creating a glucosamine-producing strain (i.e., eliminating glucosamine degradation and uptake and increasing expression of the glmS gene), the present inventors have also established that reducing product inhibition of glucosamine-6-phosphate synthase by glucosamine-6-phosphate improves glucosamine production.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. A method to produce glucosamine by fermentation, comprising:
   a. culturing in a fermentation medium comprising assimilable sources of carbon, nitrogen and phosphate, a microorganism which comprises at least one genetic modification that increases the activity of glucosamine-6-phosphate synthase, wherein said genetic modification is selected from the group consisting of:
      i. transformation of said microorganisn with a recombinant nucleic acid molecule encoding glucosamine-6-phosphate synthase from *E. coli* which has glucosamine-6-phosphate synthase activity; and
      ii. genetic modification of a gene encoding glucosamine-6-phosphate synthase from *E. coli* that increases the activity of said glucosamine-6-phosphate synthase, wherein said genetic modification results in at least one nucleic acid modification selected from the group consisting of deletion, insertion, and substitution of at least one nucleotide of said gene encoding glucosamine-6-phosphate synthase, said at least one nucleotide modification resulting in increased glucosamine-6-phosphate synthase activity;
   wherein said step of culturing produces and accumulates a product selected from the group consistng of glucosamine-6-phosphate and glucosamine from said microorganism; and
   b. recovering and purifying said product.

2. The method of claim 1, wherein said glucosamine-6-phosphate is intracellular and said glucosamine is extracellular, wherein said step of recovering comprises a recovering step selected from the group consisting of recovering said glucosamine-6-phosphate from said microorganism, recovering said glucosamine from said fermentation medium, and a combination thereof.

3. The method of claim 1, wherein said product is intracellular glucosamine-6-phosphate and said step of recovering comprises isolating said glucosamine-6-phosphate from said microorganism.

4. The method of claim 1, wherein said product is intracellular glucosamine-6-phosphate and said step of recovering further comprises dephosphorylating said glucosamine-6-phosphate to produce glucosamine.

5. The method of claim 1, wherein said step of culturing comprises maintaining said source of carbon at a concentration of from about 0.5% to about 5% in said fermentation medium.

6. The method of claim 1, wherein said step of culturing is performed at a temperature from about 28° C. to about 37° C.

7. The method of claim 1, wherein said step of culturing is performed in a fermentor.

8. The method of claim 1, wherein said step of culturing produces and accumulates at least about 1 g/L of said product.

9. The method of claim 1, wherein said genetic modification comprises transformation of said microorganism with a recombinant nucleic acid molecule encoding glucosamine-6-phosphate synthase from *E. coli* which has glucosamine-6-phosphate synthase enzymatic activity, wherein said recombinant nucleic acid molecule is operatively linked to a transcription control sequence.

10. The method of claim 9, wherein said recombinant nucleic acid molecule comprises a nucleic acid sequence encoding amino acid sequence SEQ ID NO:16.

11. The method of claim 9, wherein said recombinant nucleic acid molecule comprises a nucleic acid sequence selected from the group consisting of SEQ ID NO:13, SEQ ID NO:14 and SEQ ID NO:15.

12. The method of claim 9, wherein said recombinant nucleic acid molecule comprises a nucleic acid molecule selected from the group consisting of pKLN23-28, nglmS-$28_{2184}$ and nglmS-$28_{1830}$.

13. The method of claim 9, wherein said recombinant nucleic acid molecule is integrated into the genome of said microorganism.

14. The method of claim 9, wherein said recombinant nucleic acid molecule encoding glucosamine-6-phosphate synthase comprises a genetic modification which increases the activity of said glucosamine-6-phosphate synthase.

15. The method of claim 1, wherein said recombinant nucleic acid molecule encoding glucosamine-6-phosphate synthase or said gene encoding said glucosamine-6-phosphate synthase from *E. coli* comprises a genetic modification which reduces glucosamine-6-phosphate product inhibition of said glucosamine-6-phosphate synthase.

16. The method of claim 1, wherein said at least one nucleic acid modification results in an amino acid modification at an amino acid sequence position, corresponding to amino acid sequence SEQ ID NO:16, selected from the group consisting of Ile(4), Ile(272), Ser(450), Ala(39), Arg(250), Gly(472), Leu(469), and combinations thereof.

17. The method of claim 16, wherein said amino acid modification is a substitution selected from the group consisting of:

(a) an amino acid residue having an aliphatic hydroxyl side group for Ile(4);

(b) an amino acid residue having an aliphatic hydroxyl side group for Ile(272);

(c) an amino acid residue having an aliphatic side group for Ser(450);

(d) an amino acid residue having an aliphatic hydroxyl side group for Ala(39);

(e) an amino acid residue having a sulfur-containing side group for Arg(250);

(f) an amino acid residue having an aliphatic hydroxyl side group for Gly(472);

(g) an amino acid residue having an aliphatic side group for Leu(469);

(h) and combinations of (a)–(g).

18. The method of claim 16, wherein said amino acid modification is a substitution selected from the group consisting of: Ile(4) to Thr, Ile(272) to Thr, Ser(450) to Pro, Ala(39) to Thr, Arg(250) to Cys, Gly(472) to Ser, Leu(469) to Pro, and combinations thereof.

19. The method of claim 16, wherein said amino acid modification is a substitution of a proline residue for a leucine residue at amino acid sequence position Leu(469).

20. The method of claim 16, wherein said amino acid modification is a substitution of an amino acid residue selected from the group consisting of:

(a) a threonine residue for an alanine residue at position Ala(39);

(b) a cysteine residue for an arginine residue at position Arg(250);

(c) a serine residue for a glycine residue at position Gly(472); and (d) any combination of (a), (b), or (c).

21. The method of claim 16, wherein said amino acid modification is a substitution selected from the group consisting of:

(a) a threonine residue for an isoleucine residue at position Ile(4);

(b) a threonine residue for an isoleucine residue at position Ile(272);

(c) a proline residue for a serine residue at position Ser(450); and (d) any combination of (a), (b), or (c).

22. The method of claim 14, wherein said recombinant nucleic acid molecule comprises a nucleic acid sequence encoding a glucosamine-6-phosphate synthase comprising an amino acid sequence selected from the group consisting of SEQ ID NO:19, SEQ ID NO:22, SEQ ID NO:25, SEQ ID NO:28 and SEQ ID NO:31.

23. The method of claim 14, wherein said recombinant nucleic acid molecule comprises a nucleic acid sequence selected from the group consisting of SEQ ID NO:17, SEQ ID NO:18, SEQ ID NO:20, SEQ ID NO:21, SEQ ID NO:23, SEQ ID NO:24, SEQ ID NO:26, SEQ ID NO:27, SEQ ID NO:29 and SEQ ID NO:30.

24. The method of claim 14, wherein said recombinant nucleic acid molecule comprises a nucleic acid molecule selected from the group consisting of pKLN23-49, pKLN23-54, pKLN23-124, pKLN23-149, pKLN23-151, nglmS-$49_{2184}$, nglmS-$49_{1830}$, nglmS-$54_{2184}$, nglmS-$54_{1830}$, nglmS-$124_{2184}$, nglmS-$124_{1830}$, nglmS-$149_{2184}$, nglmS-$149_{1830}$, nglmS-$151_{2184}$ and nglmS-$151_{1830}$.

25. The method of claim 14, wherein said recombinant nucleic acid molecule is integrated into the genome of said microorganism.

26. The method of claim 1, wherein said microorganism has at least one additional genetic modification in a gene encoding a protein selected from the group consisting of N-acetylglucosamine-6-phosphate deacetylase, glucosamine-6-phosphate deaminase, N-acetylglucosamine-specific enzyme II$^{Nag}$, phosphoglucosamine mutase, glucosamine-1-phosphate acetyltransferase-N-acetylglucosamine-1-phosphate uridyltransferase, phosphofructokinase, Enzyme II$^{Glc}$ of the PEP:glucose PTS, and EIJM,P/III$^{Man}$ of the PEP:mannose PTS, wherein said genetic modification decreases the activity of said protein.

27. The method of claim 1, wherein said microorganism has at least one additional genetic modification in a gene encoding a phosphatase, wherein said genetic modification increases the activity of said phosphatase.

28. The method of claim 1, wherein said microorganism has additional modifications in genes encoding the following proteins: N-acetylglucosamine-6-phosphate deacetylase, glucosamine-6-phosphate deaminase and N-acetylglucosamine-specific enzyme II$^{Nag}$;
wherein said genetic modification decreases the activity of said proteins.

29. The method of claim 28, wherein said genetic modification is a deletion of at least a portion of said genes.

30. The method of claim 1, wherein said microorganism is selected from the group consisting of bacteria and yeast.

31. The method of claim 1, wherein said microorganism is a bacterium of the genus Escherichia.

32. The method of claim 1, wherein said microorganism is *Escherichia coli*.

33. The method of claim 32, wherein said microorganism comprises at least one additional genetic modification which is a mutation in an *Escherichia coli* gene selected from the group consisting of nagA, nagB, nagC, nagD, nagE, manXYZ, glmM, pfkB, pfkA, glmU, glmS, ptsG and a phosphatase gene, wherein said genetic modification decreases the activity of a protein encoded by said gene.

34. A method to produce glucosamine by fermentation, comprising:
a. culturing in a fermentation medium comprising assimilable sources of carbon, nitrogen and phosphate, an *Escherichia coli* transformed with a recombinant nucleic acid molecule encoding glucosamine-6-phosphate synthase from *E. coli*, wherein said recombinant nucleic acid molecule increases glucosamine-6-phosphate synthase activity in said *Escherichia coli*, and wherein said recombinant nucleic acid molecule is operatively linked to a transcription control sequence; wherein said step of culturing produces and accumulates a product selected from the group consisting of glucosamine-6-phosphate and glucosamine from said *Escherichia coli*; and
b. recovering and purifing said product.

35. The metod of claim 34, wherein said *Escherichia coli* has at least one additonal genetic modificaton in at least one gene selected from the group consisting of nagA, nagB, nagC, nagD, nagE, manXYZ, glmM, pfkB, pfkA, glmU, glmS, ptsG and a phosphatase gene, wherein said genetic modification decreases the activity of a protein encoded by said gene.

36. The method of claim 34, wherein said at least one additional genetic modification comprises a deletion of nagA, nagB, nagC, nagD, nagE, and a mutation in manXYZ, said modification resulting in decreased activity of N-acetylglucosamine-6-phosphate deacetylase, glucosamine-6-phosphate deaminase and N-acetylglucosamine-specific enzyme II$^{Nag}$.

37. A microorganism for producing glucosamine by a biosynthetic process, said microorganism being transformed with a recombinant nucleic acid molecule comprising a nucleic acid sequence encoding glucosamine-6-phosphate synthase from *E. coli*, said nucleic acid sequence being operatively linked to a transcription control sequence and comprising a genetic modification which increases the activity of said glucosamine-6-phosphate synthase;
wherein expression of said nucleic acid sequence increases production of glucosamine by said microorganism.

38. The microorganism of claim 37, wherein said microorganism has at least one additional genetic modification in a gene encoding a protein selected from the group consistng of N-acetylglucosamine-6-phosphate deacetylase, glucosamine-6-phosphate deaminase, N-acetylglucosamine-specific enzyme II$^{Nag}$, phosphoglucosamine mutase, glucosamine-1-phosphate acetyltransferase-N-acetylglucosamine-1-phosphate uridyltransferase, phosphofructokinase, Enzyme II$^{Glc}$ of the PEP:glucose PTS, and EIIM,P/III$^{Man}$ of the PEP:mannose PTS, wherein said genetic modificaton decreases the activity of said protein.

39. The microorganism of claim 37, wherein said microorganism has at least one additional genetic modification in a gene encoding a phosphatase, wherein said genetic modification increases the activity of said phosphatase.

40. The microorganism of claim 37, wherein said microorganism is *Escherichia coli* which has at least one additional genetic modification in a gene selected from the group consisting of nagA, nagB, nagC, nagD, nagE, manXYZ, glmM, pfkB, pfkA, glmU, and ptsG, wherein said genetic modificaton decreases the activity of a protein encoded by said gene.

41. The microorganism of claim 37, wherein said microorganism is *Escherichia coli* which has a deletion of nag regulon genes.

42. The microorganism of claim 37, wherein said microorganism is *Escherichia coli* which has a deletion of nag regulon genes and a genetic modification in manXYZ genes such that proteins encoded by said manXYZ genes have decreased activity.

43. The microorganism of claim 37, wherein said microorganism produces at least about 1 g/L of glucosamine when cultured from about 10 to about 60 hours at from about 28° C. to about 37° C. to a cell density of at least about 8 g/L by dry cell weight, in a pH 7.0 fermentation medium comprising: 14 g/L K$_2$HPO$_4$, 16 g/L KH$_2$PO$_4$, 1 g/L Na$_3$Citrate. 2H$_2$O, 5 g/L (NH$_4$)$_2$SO$_4$, 20 g/L glucose, 1 mM MgSO$_4$, 0.1 mM CaCl$_2$, and from about 0.2 mM to about 1 mM IPTG.

44. A microorganism for producing glucosamine by a biosynthetic process, said microorganism comprising:
(a) a recombinant nucleic acid molecule encoding glucosamine-6-phosphate synthase from *E. coli*, said recombinant nucleic acid molecule being operatively linked to a transcription control sequence, wherein expression of said recombinant nucleic acid molecule increases the activity of glucosamine-6-phosphate synthase by said microorganism; and,
(b) at least one genetic modification in a gene encoding a protein selected from the group consisting of N-acetylglucosamine-6-phosphate deacetylase, glucosamine-6-phosphate deaminase, N-acetylglucosamine-specific enzyme II$^{Nag}$ and EIIM,P/III$^{Man}$ of the PEP:mannose PTS, wherein said genetic modification decrease the activity of said protein.

45. The microorganism of claim 44, wherein said microorganism has at least one additional genetic modification in a gene encoding a phosphatase, wherein said genetic modification increases the activity of said phosphatase.

46. A recombinant nucleic acid molecule comprising a nucleic acid sequence encoding a glucosamine-6-phosphate synthase from *E. coli* having a genetic modification that results in increased glucosamine-6-phosphate synthase activity.

47. The recombinant nucleic acid molecule of claim 46, wherein said genetic modification results in at least one amino acid modification selected from the group consisting of deletion, insertion, inversion, substitution and derivatization of at least one amino acid residue of said glucosamine-6-phosphate synthase, said at least one amino acid modification resulting in increased glucosamine-6-phosphate synthase activity.

48. The recombinant nucleic acid nolecule of claim 46, wherein said recombinant nucleic acid molecule comprises a nucleic acid sequence encoding a glucosamine-6-phosphate synthase comprising an amino acid sequence selected from the group consisting of SEQ ID NO:19, SEQ ID NO:22, SEQ ID NO:25, SEQ ID NO:28 and SEQ ID NO:31.

49. The recombinant nucleic acid molecule of claim 46, wherein said recombinant nucleic acid molecule comprises a nucleic acid sequence selected from the group consisting of SEQ ID NO:17, SEQ ID NO:18, SEQ ID NO:20, SEQ ID NO:21, SEQ ID NO:23, SEQ ID NO:24, SEQ ID NO:26, SEQ ID NO:27, SEQ ID NO:29 and SEQ ID NO:30.

50. A method to produce glucosamine by fermentation, comprising:
   a. culturing in a fermentation medium comprising assimilable sources of carbon, nitrogen and phosphate, a microorganism having at least one genetic modification that increases the activity of glucosamine-6-phosphate synthase wherein said genetic modification is selected from the group consisting of:
      i. transformation of said microorganism with a recombinant nucleic acid molecule encoding glucosamine-6-phosphate synthase from *E. coli* which has glucosamine-6-phosphate synthase activity; and
      ii. genetic modification of a gene encoding glucosamine-6-phosphate synthase from *E. coli* that increases the activity of said glucosamine-6-phosphate synthase, and wherein said genetically modified microorganism is produced by a process comprising the steps of:
         (1) generating modifications in an isolated nucleic acid molecule comprising a nucleic acid sequence encoding glucosamine-6-phosphate synthase from *E. coli* to create a plurality of modified nucleic acid sequences;
         (2) transforming microorganisms with said modified nucleic acid sequences to produce genetically modified microorganisms;
         (3) screening said genetically modified microorganisms for glucosamine-6-phosphate synthase activity; and,
         (4) selecting said genetically modified microorganisms which have increased glucosamine-6-phosphate synthase activity;
   wherein said step of culturing produces a product selected from the group consisting of glucosamine-6-phosphate and glucosamine from said microorganism; and,
   b. recovering said product.

51. The method of claim 1, wherein said microorganism has additional modifications in genes encoding N-acetylglucosamine-6-phosphate deacetylase and glucosamine-6-phosphate deaminase.

52. The method of claim 1, wherein said microorganism is a yeast.

53. The method of claim 1, wherein said step of culturing is performed at about 30° C.

54. The method of claim 7, wherein said step of culturing is perfomed under conditions wherein glucose is added to said fermentation medium at a rate in which glucose accumulation in said fermentation medium is undetectable.

55. The method of clam 7, wherein said step of culturing is performed so that an excess of glucose is maintained.

56. The microorganism of claim 37, wherein said microorganism is *Escherichia coli* which comprises at least one additional genetic modification in a gene selected from the group consisting of nagA, nagB, nagC, nagD and nagE, wherein said genetic modification decreases the activity of a protein encoded by said gene.

57. The microorganism of claim 37, wherein said microorganism is *Escherichia coli* which has at least one additional genetic modification in a gene selected from the group consisting of nagA, nagB, nagC, nagD and nagE, wherein said genetic modificaton decreases the activity of a protein encoded by said gene, and a genetic modification in manXYZ genes such that proteins encoded by said manXYZ genes have decreased activity.

58. The method of claim 1, wherein said step of culturing produces and accumulates at least about 21 mg/L of said product.

59. The method of claim 1, wherein said step of culturing produces and accumulates at least about 5 g/L of said product.

* * * * *

SEQUENCE LISTING

```
<160> NUMBER OF SEQ ID NOS: 31

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 1
cggtctccca tgtgtggaat tgttggcgc                                       29

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 2
ctctagagcg ttgatattca gtcaattaca aaca                                 34

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 3
atggatgagc agacgatggt                                                 20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 4
cctcgaggtc gacggtatc                                                  19

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 5
tggatgagca gacgatgg                                                   18
```

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 6
tccgtcacag gtatttattc                                              20

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 7
agctgcgtgg tgcgtac                                                 17

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 8
ggaccgtgtt tcagttcg                                                18

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 9
gccgtggcga tcagtac                                                 17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 10
gccaatcacc agcggac                                                 17

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 11
atggtttccc gctactgg                                                18

<210> SEQ ID NO 12
<211> LENGTH: 18
<212> TYPE: DNA
<213> ORGANISM: Artificial Sequence
<220> FEATURE:
```

-continued

<223> OTHER INFORMATION: Description of Artificial Sequence:primer

<400> SEQUENCE: 12
gaaccaaggt aacccagc                                                    18

<210> SEQ ID NO 13
<211> LENGTH: 7408
<212> TYPE: DNA
<213> ORGANISM: Escherichia coli
<220> FEATURE:
<221> NAME/KEY: RBS
<222> LOCATION: (1240)..(1245)
<220> FEATURE:
<221> NAME/KEY: promoter
<222> LOCATION: (1165)..(1181)
<220> FEATURE:
<221> NAME/KEY: conflict
<222> LOCATION: (2509)..(2510)

<400> SEQUENCE: 13

| | | |
|---|---|---|
| gaattgatcc cgtcgtttta caacgtcgtg actgggaaaa ccctggcgtt acccaactta | 60 |
| atcgccttgc agcacatccc cctttcgcca gctggcgtaa tagcgaagag cccgcaccg | 120 |
| atcgcccttc ccaacagttg cgcagcctga atggcgaatg gcgctttgcc tggtttccgg | 180 |
| caccagaagc ggtgccggaa agctggctgg agtgcgatct tcctgaggcc gatactgtcg | 240 |
| tcgtcccctc aaactggcag atgcacggtt acgatgcgcc catctacacc aacgtaacct | 300 |
| atcccattac ggtcaatccg ccgtttgttc ccacggagaa tccgacgggt tgttactcgc | 360 |
| tcacatttaa tgttgatgaa agctggctac aggaaggcca gacgcgaatt atttttgatg | 420 |
| gcgttaactc ggcgtttcat ctgtggtgca acgggcgctg gtcggttac ggccaggaca | 480 |
| gtcgtttgcc gtctgaattt gacctgagcg cattttacg cgccggagaa accgcctcg | 540 |
| cggtgatggt gctgcgttgg agtgacggca gttatctgga agatcaggat atgtggcgga | 600 |
| tgagcggcat tttccgtgac gtctcgttgc tgcataaacc gactacacaa atcagcgatt | 660 |
| tccatgttgc cactcgcttt aatgatgatt tcagccgcgc tgtactggag gctgaagttc | 720 |
| agatgtgcgg cgagttgcgt gactacctac gggtaacagt ttctttatgg cagggtgaaa | 780 |
| cgcaggtcgc cagcggcacc gcgccttttcg gcggtgaaat tatcgatgag cgtggtggtt | 840 |
| atgccgatcg cgtcacacta cgtctgaacg tcgaaaaccc gaaactgtgg agcgccgaaa | 900 |
| tcccgaatct ctatcgtgcg gtggttgaac tgcacaccgc cgacggcacg ctgattgaag | 960 |
| cagaagcctg cgatgtcggt ttccgcgagg tgcggattga aaatggtctg ctgctgctga | 1020 |
| acggcaagcc gttgctgatt cgaggcgtta accgtcacga gcatcatcct ctgcatggtc | 1080 |
| aggtcatgga tgagcagacg atggtgcagg atctccaccg cggtggcggc cgctctagaa | 1140 |
| ctagtggatc tcgatcccgc gaaattaata cgactcacta tagggaatt gtgagcggat | 1200 |
| aacaattccc ctctagaaat aatttgttt aactttaaga aggagatata ccatgtgtgg | 1260 |
| aattgttggc gcgatcgcgc aacgtgatgt agcagaaatc cttcttgaag gtttacgtcg | 1320 |
| tctggaatac cgcggatatg actctgccgg tctggccgtt gttgatgcag aaggtcatat | 1380 |
| gacccgcctg cgtcgcctcg gtaaagtcca gatgctggca caggcagcgg aagaacatcc | 1440 |
| tctgcatggc ggcactggta ttgctcacac tcgctgggcg acccacggtg aaccttcaga | 1500 |
| agtgaatgcg catccgcatg tttctgaaca cattgtggtg gtgcataacg gcatcatcga | 1560 |
| aaaccatgaa ccgctgcgtg aagagctaaa agcgcgtggc tataccttcg tttctgaaac | 1620 |
| cgacaccgaa gtgattgccc atctggtgaa ctgggagctg aaacaaggcg ggactctgcg | 1680 |

-continued

```
tgaggccgtt ctgcgtgcta tcccgcagct gcgtggtgcg tacggtacag tgatcatgga      1740
ctcccgtcac ccggataccc tgctggcggc acgttctggt agtccgctgg tgattggcct      1800
ggggatgggc gaaaacttta tcgcttctga ccagctggcg ctgttgccgg tgacccgtcg      1860
ctttatcttc cttgaagagg gcgatattgc ggaaatcact cgccgttcgg taaacatctt      1920
cgataaaact ggcgcggaag taaaacgtca ggatatcgaa tccaatctgc aatatgacgc      1980
gggcgataaa ggcatttacc gtcactacat gcagaaagag atctacgaac agccgaacgc      2040
gatcaaaaac cccttaccg gacgcatcag ccacggtcag gttgatttaa gcagctggg       2100 accgaacgcc gacgaactgc tgtcgaaggt tgagcatatt cagatcctcg cctgtggtac      2160
ttcttataac tccggtatgg tttcccgcta ctggtttgaa tcgctagcag gtattccgtg      2220
cgacgtcgaa atcgcctctg aattccgcta tcgcaaatct gccgtgcgtc gtaacagcct      2280
gatgatcacc ttgtcacagt ctggcgaaac cgcggatacc ctggctggcc tgcgtctgtc      2340
gaaagagctg ggttaccttg gttcactggc aatctgtaac gttccgggtt cttctctggt      2400
gcgcgaatcc gatctggcgc taatgaccaa cgcgggtaca gaaatcggcg tggcatccac      2460
taaagcattc accactcagt taactgtgct gttgatgctg gtggcgaagc tgtctcgcct      2520
gaaaggtctg gatgcctcca ttgaacatga catcgtgcat ggtctgcagg cgctgccgag      2580
ccgtattgag cagatgctgt ctcaggacaa acgcattgaa gcgctggcag aagatttctc      2640
tgacaaacat cacgcgctgt tcctgggccg tggcgatcag tacccaatcg cgctggaagg      2700
cgcattgaag ttgaaagaga tctcttacat tcacgctgaa gcctacgctg ctggcgaact      2760
gaaacacggt ccgctggcgc taattgatgc cgatatgccg gttattgttg ttgcaccgaa      2820
caacgaattg ctggaaaaac tgaaatccaa cattgaagaa gttcgcgcgc gtggcggtca      2880
gttgtatgtc ttcgccgatc aggatgcggg ttttgtaagt agcgataaca tgcacatcat      2940
cgagatgccg catgtggaag aggtgattgc accgatcttc tacaccgttc cgctgcagct      3000
gctggcttac catgtcgcgc tgatcaaagg caccgacgtt gaccagccgc gtaacctggc      3060
aaaatcggtt acgttgagt aataaatgga tgccctgcgt aagcgggca ttttttcttcc      3120 tgttatgttt ttaatcaaac atcctgccaa ctccatgtga caaaccgtca tcttcggcta      3180 cttttctct gtcacagaat gaaaattttt ctgtcatctc ttcgttatta atgtttgtaa      3240
ttgactgaat atcaacgctc tagagggct agagcggccg ccaccgcggt ggagctccgt      3300
cgacaagctt atcgataccg tcgacctcga gggggggccc ggtaccgagg acgcgttcga      3360
ataaatacct gtgacggaag atcacttcgc agaataaata atcctggtg tccctgttga      3420 taccgggaag ccctgggcca acttttggcg aaaatgagac gttgatcggc acgtaagagg      3480
ttccaacttt caccataatg aaataagatc actaccgggc gtattttttg agttatcgag      3540
attttcagga gctaaggaag ctaaaatgga gaaaaaaatc actggatata ccaccgttga      3600
tatatcccaa tggcatcgta agaacatttt tgaggcattt cagtcagttg ctcaatgtac      3660
ctataaccag accgttcagc tggatattac ggccttttta aagaccgtaa agaaaaataa      3720
gcacaagttt tatccggcct ttattcacat tcttgcccgc ctgatgaatg ctcatccgaa      3780
attccgtatg gcaatgaaag acggtgagct ggtgatatgg gatagtgttc acccttgtta      3840 caccgtttc catgagcaaa ctgaaacgtt ttcatcgctc tggagtgaat accacgacga      3900
tttccggcag tttctacaca tatattcgca agatgtggcg tgttacgtg aaaacctggc      3960 ctatttccct aaagggttta ttgagaatat gttttcgtc tcagccaatc cctgggtgag      4020
tttcaccagt tttgatttaa acgtggccaa tatggacaac ttcttcgccc ccgttttcac      4080
```

```
catgggcaaa tattatacgc aaggcgacaa ggtgctgatg ccgctggcga ttcaggttca   4140
tcatgccgtt tgtgatggct tccatgtcgg cagaatgctt aatgaattac aacagtactg   4200
cgatgagtgg caggcgggg cgtaatttt ttaaggcagt tattggtgcc cttaaacgcc    4260
tggtgctacg cctgaataag tgataataag cggatgaatg gcagaaattc ggacgcgtca   4320
attcgagctc ctgcactgga tggtggcgct ggatggtaag ccgctggcaa gcggtgaagt   4380
gcctctggat gtcgctccac aaggtaaaca gttgattgaa ctgcctgaac taccgcagcc   4440
ggagagcgcc gggcaactct ggctcacagt acgcgtagtc aaccgaacg cgaccgcatg    4500 gtcagaagcc gggcacatca gcgcctggca gcagtggcgt ctggcggaaa acctcagtgt   4560
gacgctcccc gccgcgtccc acgccatccc gcatctgacc accagcgaaa tggatttttg   4620
catcgagctg ggtaataagc gttggcaatt taaccgccag tcaggctttc tttcacagat   4680
gtggattggc gataaaaaac aactgctgac gccgctgcgc gatcagttca cccgtgcacc   4740
gctggataac gacattggcg taagtgaagc gacccgcatt gaccctaacg cctgggtcga   4800
acgctggaag gcggcgggcc attaccaggc cgaagcagcg ttgttgcagt gcacggcaga   4860
tacacttgct gatgcggtgc tgattacgac cgctcacgcg tggcagcatc aggggaaaac   4920
cttatttatc agccggaaaa cctaccggat tgatggtagt ggtcaaatgg cgattaccgt   4980
tgatgttgaa gtggcgagcg atacaccgca tccggcgcgg attggcctga actgccagct   5040
ggcgcaggta gcagagcggg taaactggct cggattaggg ccgcaagaaa actatcccga   5100
ccgccttact gccgcctgtt tgaccgctg ggatctgcca ttgtcagaca tgtataccc    5160 gtacgtcttc ccgagcgaaa acggtctgcg ctgcgggacg cgcgaattga attatggccc   5220
acaccagtgg cgcggcgact tccagttcaa catcagccgc tacagtcaac agcaactgat   5280
ggaaaccagc catcgccatc tgctgcacgc ggaagaaggc acatggctga atatcgacgg   5340
tttccatatg cggtgtgaaa taccgcacag atgcgtaagg agaaaatacc gcatcaggcg   5400
ctcttccgct tcctcgctca ctgactcgct gcgctcggtc gttcggctgc ggcgagcggt   5460
atcagctcac tcaaaggcgg taatacggtt atccacagaa tcagggata acgcaggaaa   5520 gaacatgtga gcaaaaggcc agcaaaaggc caggaaccgt aaaaaggccg cgttgctggc   5580
gtttttccat aggctccgcc cccctgacga gcatcacaaa aatcgacgct caagtcagag   5640
gtggcgaaac ccgacaggac tataaagata ccaggcgttt ccccctggaa gctccctcgt   5700
gcgctctcct gttccgaccc tgccgcttac cggatacctg tccgcctttc tcccttcggg   5760
aagcgtggcg ctttctcaat gctcacgctg taggtatctc agttcggtgt aggtcgttcg   5820
ctccaagctg ggctgtgtgc acgaaccccc cgttcagccc gaccgctgcg ccttatccgg   5880
taactatcgt cttgagtcca acccggtaag acacgactta tcgccactgg cagcagccac   5940
tggtaacagg attagcagag cgaggtatgt aggcggtgct acagagttct tgaagtggtg   6000
gcctaactac ggctacacta gaaggacagt atttggtatc tgcgctctgc tgaagccagt   6060
taccttcgga aaaagagttg gtagctcttg atccggcaaa caaaccaccg ctggtagcgg   6120
tggttttttt gtttgcaagc agcagattac gcgcagaaaa aaaggatctc aagaagatcc   6180
tttgatcttt tctacgggt ctgacgctca gtggaacgaa aactcacgtt aagggatttt   6240
ggtcatgaga ttatcaaaaa ggatcttcac ctagatcctt ttaaattaaa aatgaagttt   6300
taaatcaatc taaagtatat atgagtaaac ttggtctgac agttaccaat gcttaatcag   6360
tgaggcacct atctcagcga tctgtctatt tcgttcatcc atagttgcct gactccccgt   6420
```

-continued

| | | | |
|---|---|---|---|
| cgtgtagata actacgatac gggagggctt accatctggc cccagtgctg caatgatacc | 6480 |
| gcgagaccca cgctcaccgg ctccagattt atcagcaata aaccagccag ccggaagggc | 6540 |
| cgagcgcaga agtggtcctg caactttatc cgcctccatc cagtctatta attgttgccg | 6600 |
| ggaagctaga gtaagtagtt cgccagttaa tagtttgcgc aacgttgttg ccattgctac | 6660 |
| aggcatcgtg gtgtcacgct cgtcgtttgg tatggcttca ttcagctccg gttcccaacg | 6720 |
| atcaaggcga gttacatgat cccccatgtt gtgcaaaaaa gcggttagct ccttcggtcc | 6780 |
| tccgatcgtt gtcagaagta agttggccgc agtgttatca ctcatggtta tggcagcact | 6840 |
| gcataattct cttactgtca tgccatccgt aagatgcttt tctgtgactg gtgagtactc | 6900 |
| aaccaagtca ttctgagaat agtgtatgcg gcgaccgagt tgctcttgcc cggcgtcaat | 6960 |
| acgggataat accgcgccac atagcagaac tttaaaagtg ctcatcattg gaaaacgttc | 7020 |
| ttcggggcga aaactctcaa ggatcttacc gctgttgaga tccagttcga tgtaacccac | 7080 |
| tcgtgcaccc aactgatctt cagcatcttt tactttcacc agcgtttctg ggtgagcaaa | 7140 |
| aacaggaagg caaaatgccg caaaaaaggg aataagggcg acacggaaat gttgaatact | 7200 |
| catactcttc ctttttcaat attattgaag catttatcag ggttattgtc tcatgagcgg | 7260 |
| atacatattt gaatgtattt agaaaaataa acaaataggg gttccgcgca catttccccg | 7320 |
| aaaagtgcca cctgacgtct aagaaaccat tattatcatg acattaacct ataaaaatag | 7380 |
| gcgtatcacg aggcccttc gtcttcaa | 7408 |

<210> SEQ ID NO 14
<211> LENGTH: 2184
<212> TYPE: DNA
<213> ORGANISM: Escherichia coli

<400> SEQUENCE: 14

| | | |
|---|---|---|
| ccgctctaga actagtggat ctcgatcccg cgaaattaat acgactcact ataggggaat | 60 |
| tgtgagcgga taacaattcc cctctagaaa taattttgtt taactttaag aaggagatat | 120 |
| accatgtgtg gaattgttgg cgcgatcgcg caacgtgatg tagcagaaat ccttcttgaa | 180 |
| ggtttacgtc gtctggaata ccgcggatat gactctgccg gtctggccgt tgttgatgca | 240 |
| gaaggtcata tgacccgcct gcgtcgcctc ggtaaagtcc agatgctggc acaggcagcg | 300 |
| gaagaacatc ctctgcatgg cggcactggt attgctcaca ctcgctgggc gacccacggt | 360 |
| gaaccttcag aagtgaatgc gcatccgcat gtttctgaac acattgtggt ggtgcataac | 420 |
| ggcatcatcg aaaaccatga accgctgcgt gaagagctaa agcgcgtgg ctataccttc | 480 |
| gtttctgaaa ccgacaccga agtgattgcc catctggtga actgggagct gaaacaaggc | 540 |
| gggactctgc gtgaggccgt tctgcgtgct atcccgcagc tgcgtggtgc gtacggtaca | 600 |
| gtgatcatgg actcccgtca cccggatacc ctgctggcgg cacgttctgg tagtccgctg | 660 |
| gtgattggcc tggggatggg cgaaaacttt atcgcttctg accagctggc gctgttgccg | 720 |
| gtgacccgtc gctttatctt ccttgaagag ggcgatattg cggaaatcac tcgccgttcg | 780 |
| gtaaacatct tcgataaaac tggcgcggaa gtaaaacgtc aggatatcga atccaatctg | 840 |
| caatatgacg cgggcgataa aggcatttac cgtcactaca tgcagaaaga gatctacgaa | 900 |
| cagccgaacg cgatcaaaaa caccccttacc ggacgcatca gccacggtca ggttgattta | 960 |
| agcgagctgg gaccgaacgc cgacgaactg ctgtcgaagg ttgagcatat tcagatcctc | 1020 |
| gcctgtggta cttcttataa ctccggtatg gtttcccgct actggtttga atcgctagca | 1080 |
| ggtattccgt gcgacgtcga aatcgcctct gaattccgct atcgcaaatc tgccgtgcgt | 1140 |

-continued

```
cgtaacagcc tgatgatcac cttgtcacag tctggcgaaa ccgcggatac cctggctggc      1200
ctgcgtctgt cgaaagagct gggttacctt ggttcactgg caatctgtaa cgttccgggt      1260
tcttctctgg tgcgcgaatc cgatctggcg ctaatgacca cgcgggtac agaaatcggc       1320 gtggcatcca ctaaagcatt caccactcag ttaactgtgc tgttgatgct ggtggcgaag      1380
ctgtctcgcc tgaaaggtct ggatgcctcc attgaacatg acatcgtgca tggtctgcag      1440
gcgctgccga gccgtattga gcagatgctg tctcaggaca aacgcattga agcgctggca      1500
gaagatttct ctgacaaaca tcacgcgctg ttcctgggcc gtggcgatca gtacccaatc      1560
gcgctggaag gcgcattgaa gttgaaagag atctcttaca ttcacgctga agcctacgct      1620
gctggcgaac tgaaacacgg tccgctggcg ctaattgatg ccgatatgcc ggttattgtt      1680
gttgcaccga caacgaatt gctggaaaaa ctgaaatcca acattgaaga gttcgcgcg       1740 cgtggcggtc agttgtatgt cttcgccgat caggatgcgg ttttgtaag tagcgataac      1800 atgcacatca tcgagatgcc gcatgtggaa gaggtgattg caccgatctt ctacaccgtt     1860
ccgctgcagc tgctggctta ccatgtcgcg ctgatcaaag gcaccgacgt tgaccagccg     1920
cgtaacctgg caaaatcggt tacggttgag taataaatgg atgccctgcg taagcggggc     1980 attttttcttc ctgttatgtt tttaatcaaa catcctgcca actccatgtg acaaaccgtc    2040
atcttcggct actttttctc tgtcacagaa tgaaaatttt tctgtcatct cttcgttatt     2100
aatgtttgta attgactgaa tatcaacgct ctagaggggc tagagcggcc gccaccgcgg      2160
tggagctccg tcgacaagct tatc                                             2184
```

<210> SEQ ID NO 15
<211> LENGTH: 1830
<212> TYPE: DNA
<213> ORGANISM: Escherichia coli
<220> FEATURE:
<221> NAME/KEY: CDS
<222> LOCATION: (1)..(1830)

<400> SEQUENCE: 15

```
atg tgt gga att gtt ggc gcg atc gcg caa cgt gat gta gca gaa atc        48
Met Cys Gly Ile Val Gly Ala Ile Ala Gln Arg Asp Val Ala Glu Ile
 1               5                  10                  15 ctt ctt gaa ggt tta cgt cgt ctg gaa tac cgc gga tat gac tct gcc        96
Leu Leu Glu Gly Leu Arg Arg Leu Glu Tyr Arg Gly Tyr Asp Ser Ala
             20                  25                  30 ggt ctg gcc gtt gtt gat gca gaa ggt cat atg acc cgc ctg cgt cgc        144
Gly Leu Ala Val Val Asp Ala Glu Gly His Met Thr Arg Leu Arg Arg
         35                  40                  45 ctc ggt aaa gtc cag atg ctg gca cag gca gcg gaa gaa cat cct ctg        192
Leu Gly Lys Val Gln Met Leu Ala Gln Ala Ala Glu Glu His Pro Leu
     50                  55                  60 cat ggc ggc act ggt att gct cac act cgc tgg gcg acc cac ggt gaa        240
His Gly Gly Thr Gly Ile Ala His Thr Arg Trp Ala Thr His Gly Glu
 65                  70                  75                  80 cct tca gaa gtg aat gcg cat ccg cat gtt tct gaa cac att gtg gtg        288
Pro Ser Glu Val Asn Ala His Pro His Val Ser Glu His Ile Val Val
                 85                  90                  95 gtg cat aac ggc atc atc gaa aac cat gaa ccg ctg cgt gaa gag cta        336
Val His Asn Gly Ile Ile Glu Asn His Glu Pro Leu Arg Glu Glu Leu
            100                 105                 110 aaa gcg cgt ggc tat acc ttc gtt tct gaa acc gac acc gaa gtg att        384
Lys Ala Arg Gly Tyr Thr Phe Val Ser Glu Thr Asp Thr Glu Val Ile
        115                 120                 125
```

```
gcc cat ctg gtg aac tgg gag ctg aaa caa ggc ggg act ctg cgt gag      432
Ala His Leu Val Asn Trp Glu Leu Lys Gln Gly Gly Thr Leu Arg Glu
    130             135                 140 gcc gtt ctg cgt gct atc ccg cag ctg cgt ggt gcg tac ggt aca gtg      480
Ala Val Leu Arg Ala Ile Pro Gln Leu Arg Gly Ala Tyr Gly Thr Val
145             150                 155                 160 atc atg gac tcc cgt cac ccg gat acc ctg ctg gcg gca cgt tct ggt      528
Ile Met Asp Ser Arg His Pro Asp Thr Leu Leu Ala Ala Arg Ser Gly
                165                 170                 175 agt ccg ctg gtg att ggc ctg ggg atg ggc gaa aac ttt atc gct tct      576
Ser Pro Leu Val Ile Gly Leu Gly Met Gly Glu Asn Phe Ile Ala Ser
            180                 185                 190 gac cag ctg gcg ctg ttg ccg gtg acc cgt cgc ttt atc ttc ctt gaa      624
Asp Gln Leu Ala Leu Leu Pro Val Thr Arg Arg Phe Ile Phe Leu Glu
        195                 200                 205 gag ggc gat att gcg gaa atc act cgc cgt tcg gta aac atc ttc gat      672
Glu Gly Asp Ile Ala Glu Ile Thr Arg Arg Ser Val Asn Ile Phe Asp
    210                 215                 220 aaa act ggc gcg gaa gta aaa cgt cag gat atc gaa tcc aat ctg caa      720
Lys Thr Gly Ala Glu Val Lys Arg Gln Asp Ile Glu Ser Asn Leu Gln
225                 230                 235                 240 tat gac gcg ggc gat aaa ggc att tac cgt cac tac atg cag aaa gag      768
Tyr Asp Ala Gly Asp Lys Gly Ile Tyr Arg His Tyr Met Gln Lys Glu
                245                 250                 255 atc tac gaa cag ccg aac gcg atc aaa aac acc ctt acc gga cgc atc      816
Ile Tyr Glu Gln Pro Asn Ala Ile Lys Asn Thr Leu Thr Gly Arg Ile
            260                 265                 270 agc cac ggt cag gtt gat tta agc gag ctg gga ccg aac gcc gac gaa      864
Ser His Gly Gln Val Asp Leu Ser Glu Leu Gly Pro Asn Ala Asp Glu
        275                 280                 285 ctg ctg tcg aag gtt gag cat att cag atc ctc gcc tgt ggt act tct      912
Leu Leu Ser Lys Val Glu His Ile Gln Ile Leu Ala Cys Gly Thr Ser
    290                 295                 300 tat aac tcc ggt atg gtt tcc cgc tac tgg ttt gaa tcg cta gca ggt      960
Tyr Asn Ser Gly Met Val Ser Arg Tyr Trp Phe Glu Ser Leu Ala Gly
305                 310                 315                 320 att ccg tgc gac gtc gaa atc gcc tct gaa ttc cgc tat cgc aaa tct     1008
Ile Pro Cys Asp Val Glu Ile Ala Ser Glu Phe Arg Tyr Arg Lys Ser
                325                 330                 335 gcc gtg cgt cgt aac agc ctg atg atc acc ttg tca cag tct ggc gaa     1056
Ala Val Arg Arg Asn Ser Leu Met Ile Thr Leu Ser Gln Ser Gly Glu
            340                 345                 350 acc gcg gat acc ctg gct ggc ctg cgt ctg tcg aaa gag ctg ggt tac     1104
Thr Ala Asp Thr Leu Ala Gly Leu Arg Leu Ser Lys Glu Leu Gly Tyr
        355                 360                 365 ctt ggt tca ctg gca atc tgt aac gtt ccg ggt tct tct ctg gtg cgc     1152
Leu Gly Ser Leu Ala Ile Cys Asn Val Pro Gly Ser Ser Leu Val Arg
    370                 375                 380 gaa tcc gat ctg gcg cta atg acc aac gcg ggt aca gaa atc ggc gtg     1200
Glu Ser Asp Leu Ala Leu Met Thr Asn Ala Gly Thr Glu Ile Gly Val
385                 390                 395                 400 gca tcc act aaa gca ttc acc act cag tta act gtg ctg ttg atg ctg     1248
Ala Ser Thr Lys Ala Phe Thr Thr Gln Leu Thr Val Leu Leu Met Leu
                405                 410                 415 gtg gcg aag ctg tct cgc ctg aaa ggt ctg gat gcc tcc att gaa cat     1296
Val Ala Lys Leu Ser Arg Leu Lys Gly Leu Asp Ala Ser Ile Glu His
            420                 425                 430 gac atc gtg cat ggt ctg cag gcg ctg ccg agc cgt att gag cag atg     1344
Asp Ile Val His Gly Leu Gln Ala Leu Pro Ser Arg Ile Glu Gln Met
```

```
ctg tct cag gac aaa cgc att gaa gcg ctg gca gaa gat ttc tct gac      1392
Leu Ser Gln Asp Lys Arg Ile Glu Ala Leu Ala Glu Asp Phe Ser Asp
    450                 455                 460 aaa cat cac gcg ctg ttc ctg ggc cgt ggc gat cag tac cca atc gcg      1440
Lys His His Ala Leu Phe Leu Gly Arg Gly Asp Gln Tyr Pro Ile Ala
465                 470                 475                 480 ctg gaa ggc gca ttg aag ttg aaa gag atc tct tac att cac gct gaa      1488
Leu Glu Gly Ala Leu Lys Leu Lys Glu Ile Ser Tyr Ile His Ala Glu
                485                 490                 495 gcc tac gct gct ggc gaa ctg aaa cac ggt ccg ctg gcg cta att gat      1536
Ala Tyr Ala Ala Gly Glu Leu Lys His Gly Pro Leu Ala Leu Ile Asp
            500                 505                 510 gcc gat atg ccg gtt att gtt gtt gca ccg aac aac gaa ttg ctg gaa      1584
Ala Asp Met Pro Val Ile Val Val Ala Pro Asn Asn Glu Leu Leu Glu
        515                 520                 525 aaa ctg aaa tcc aac att gaa gaa gtt cgc gcg cgt ggc ggt cag ttg      1632
Lys Leu Lys Ser Asn Ile Glu Glu Val Arg Ala Arg Gly Gly Gln Leu
    530                 535                 540 tat gtc ttc gcc gat cag gat gcg ggt ttt gta agt agc gat aac atg      1680
Tyr Val Phe Ala Asp Gln Asp Ala Gly Phe Val Ser Ser Asp Asn Met
545                 550                 555                 560 cac atc atc gag atg ccg cat gtg gaa gag gtg att gca ccg atc ttc      1728
His Ile Ile Glu Met Pro His Val Glu Glu Val Ile Ala Pro Ile Phe
                565                 570                 575 tac acc gtt ccg ctg cag ctg ctg gct tac cat gtc gcg ctg atc aaa      1776
Tyr Thr Val Pro Leu Gln Leu Leu Ala Tyr His Val Ala Leu Ile Lys
            580                 585                 590 ggc acc gac gtt gac cag ccg cgt aac ctg gca aaa tcg gtt acg gtt      1824
Gly Thr Asp Val Asp Gln Pro Arg Asn Leu Ala Lys Ser Val Thr Val
        595                 600                 605 gag taa                                                               1830
Glu
```

<210> SEQ ID NO 16
<211> LENGTH: 609
<212> TYPE: PRT
<213> ORGANISM: Escherichia coli

<400> SEQUENCE: 16

```
Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
                20                  25                  30

Gly Leu Ala Val Val Asp Ala Glu Gly His Met Thr Arg Leu Arg Arg
            35                  40                  45

Leu Gly Lys Val Gln Met Leu Ala Gln Ala Ala Glu Glu His Pro Leu
        50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
    130                 135                 140
```

-continued

```
Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205

Glu Gly Asp Ile Ala Glu Ile Thr Arg Arg Ser Val Asn Ile Phe Asp
210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
            340                 345                 350

Thr Ala Asp Thr Leu Ala Gly Leu Arg Leu Ser Lys Glu Leu Gly Tyr
        355                 360                 365

Leu Gly Ser Leu Ala Ile Cys Asn Val Pro Gly Ser Ser Leu Val Arg
370                 375                 380

Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
            420                 425                 430

Asp Ile Val His Gly Leu Gln Ala Leu Pro Ser Arg Ile Glu Gln Met
        435                 440                 445

Leu Ser Gln Asp Lys Arg Ile Glu Ala Leu Ala Glu Asp Phe Ser Asp
450                 455                 460

Lys His His Ala Leu Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510

Ala Asp Met Pro Val Ile Val Val Ala Pro Asn Asn Glu Leu Leu Glu
        515                 520                 525

Lys Leu Lys Ser Asn Ile Glu Glu Val Arg Ala Arg Gly Gly Gln Leu
530                 535                 540

Tyr Val Phe Ala Asp Gln Asp Ala Gly Phe Val Ser Ser Asp Asn Met
545                 550                 555                 560
```

His Ile Ile Glu Met Pro His Val Glu Val Ile Ala Pro Ile Phe
            565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
            595                 600                 605

Glu

<210> SEQ ID NO 17
<211> LENGTH: 2184
<212> TYPE: DNA
<213> ORGANISM: Escherichia coli

<400> SEQUENCE: 17

| | | | | | |
|---|---|---|---|---|---|
| ccgctctaga | actagtggat | ctcgatcccg | cgaaattaat | acgactcact | ataggggaat | 60 |
| tgtgagcgga | taacaattcc | cctctagaaa | taattttgtt | taactttaag | aaggagatat | 120 |
| accatgtgtg | aactgttggc | gcgatcgcg | caacgtgatg | tagcagaaat | ccttcttgaa | 180 |
| ggtttacgtc | gtctggaata | ccgcggatat | gactctgccg | gtctggccgt | tgttgatgca | 240 |
| gaaggtcata | tgacccgcct | gcgtcgcctc | ggtaaagtcc | agatgctggc | acaggcagcg | 300 |
| gaagaacatc | ctctgcatgg | cggcactggt | attgctcaca | ctcgctgggc | gacccacggt | 360 |
| gaaccttcag | aagtgaatgc | gcatccgcat | gtttctgaac | acattgtggt | ggtgcataac | 420 |
| ggcatcatcg | aaaaccatga | accgctgcgt | gaagagctaa | aagcgcgtgg | ctataccttc | 480 |
| gtttctgaaa | ccgacaccga | agtgattgcc | catctggtga | actgggagct | gaaacaaggc | 540 |
| gggactctgc | gtgaggccgt | tctgcgtgct | atcccgcagc | tgcgtggtgc | gtacggtaca | 600 |
| gtgatcatgg | actcccgtca | cccggatacc | ctgctggcgg | cacgttctgg | tagtccgctg | 660 |
| gtgattggcc | tggggatggg | cgaaaacttt | atcgcttctg | accagctggc | gctgttgccg | 720 |
| gtgacccgtc | gctttatctt | ccttgaagag | ggcgatattg | cggaaatcac | tcgccgttcg | 780 |
| gtaaacatct | tcgataaaac | tggcgcggaa | gtaaaacgtc | aggatatcga | atccaatctg | 840 |
| caatatgacg | cgggcgataa | aggcatttac | cgtcactaca | tgcagaaaga | gatctacgaa | 900 |
| cagccgaacg | cgatcaaaaa | cacccttacc | ggacgcacca | gccacggtca | ggttgattta | 960 |
| agcgagctgg | gaccgaacgc | cgacgaactg | ctgtcgaagg | ttgagcatat | tcagatcctc | 1020 |
| gcctgtggta | cttcttataa | ctccggtatg | gtttcccgct | actggtttga | atcgctagca | 1080 |
| ggtattccgt | gcgacgtcga | aatcgcctct | gaattccgct | atcgcaaatc | tgccgtgcgt | 1140 |
| cgtaacagcc | tgatgatcac | cttgtcacag | tctggcgaaa | ccgcggatac | cctggctggc | 1200 |
| ctgcgtctgt | cgaaagagct | gggttacctt | ggttcactgg | caatctgtaa | cgttccgggt | 1260 |
| tcttctctgg | tgcgcgaatc | cgatctggcg | ctaatgacca | acgcgggtac | agaaatcggc | 1320 |
| gtggcatcca | ctaaagcatt | caccactcag | ttaactgtgc | tgttgatgct | ggtggcgaag | 1380 |
| ctgtctcgcc | tgaaaggtct | ggatgcctcc | attgaacatg | acatcgtgca | tggtctgcag | 1440 |
| gcgctgccga | gccgtattga | gcagatgctg | cctcaggaca | aacgcattga | agcgctggca | 1500 |
| gaagatttct | ctgacaaaca | tcacgcgctg | ttcctgggcc | gtggcgatca | gtacccaatc | 1560 |
| gcgctggaag | gcgcattgaa | gttgaaagag | atctcttaca | ttcacgctga | agcctacgct | 1620 |
| gctggcgaac | tgaaacacgg | tccgctggcg | ctaattgatg | ccgatatgcc | ggttattgtt | 1680 |
| gttgcaccga | caacgaatt | gctggaaaaa | ctgaaatcca | acattgaaga | agttcgcgcg | 1740 |
| cgtggcggtc | agttgtatgt | cttcgccgat | caggatgcgg | gttttgtaag | tagcgataac | 1800 |

```
atgcacatca tcgagatgcc gcatgtggaa gaggtgattg caccgatctt ctacaccgtt   1860
ccgctgcagc tgctggctta ccatgtcgcg ctgatcaaag caccgacgt tgaccagccg    1920 cgtaacctgg caaaatcggt tacggttgag taataaatgg atgccctgcg taagcggggc   1980
atttttcttc ctgttatgtt tttaatcaaa catcctgcca actccatgtg acaaaccgtc   2040
atcttcggct acttttctc tgtcacagaa tgaaaatttt tctgtcatct cttcgttatt    2100
aatgtttgta attgactgaa tatcaacgct ctagaggggc tagagcggcc gccaccgcgg   2160
tggagctccg tcgacaagct tatc                                         2184
```

<210> SEQ ID NO 18
<211> LENGTH: 1830
<212> TYPE: DNA
<213> ORGANISM: Escherichia coli
<220> FEATURE:
<221> NAME/KEY: CDS
<222> LOCATION: (1)..(1830)

<400> SEQUENCE: 18

```
atg tgt gga act gtt ggc gcg atc gcg caa cgt gat gta gca gaa atc         48
Met Cys Gly Thr Val Gly Ala Ile Ala Gln Arg Asp Val Ala Glu Ile
 1               5                  10                  15 ctt ctt gaa ggt tta cgt cgt ctg gaa tac cgc gga tat gac tct gcc         96
Leu Leu Glu Gly Leu Arg Arg Leu Glu Tyr Arg Gly Tyr Asp Ser Ala
             20                  25                  30 ggt ctg gcc gtt gtt gat gca gaa ggt cat atg acc cgc ctg cgt cgc        144
Gly Leu Ala Val Val Asp Ala Glu Gly His Met Thr Arg Leu Arg Arg
         35                  40                  45 ctc ggt aaa gtc cag atg ctg gca cag gca gcg gaa gaa cat cct ctg        192
Leu Gly Lys Val Gln Met Leu Ala Gln Ala Ala Glu Glu His Pro Leu
     50                  55                  60 cat ggc ggc act ggt att gct cac act cgc tgg gcg acc cac ggt gaa        240
His Gly Gly Thr Gly Ile Ala His Thr Arg Trp Ala Thr His Gly Glu
 65                  70                  75                  80 cct tca gaa gtg aat gcg cat ccg cat gtt tct gaa cac att gtg gtg        288
Pro Ser Glu Val Asn Ala His Pro His Val Ser Glu His Ile Val Val
                 85                  90                  95 gtg cat aac ggc atc atc gaa aac cat gaa ccg ctg cgt gaa gag cta        336
Val His Asn Gly Ile Ile Glu Asn His Glu Pro Leu Arg Glu Glu Leu
            100                 105                 110 aaa gcg cgt ggc tat acc ttc gtt tct gaa acc gac acc gaa gtg att        384
Lys Ala Arg Gly Tyr Thr Phe Val Ser Glu Thr Asp Thr Glu Val Ile
        115                 120                 125 gcc cat ctg gtg aac tgg gag ctg aaa caa ggc ggg act ctg cgt gag        432
Ala His Leu Val Asn Trp Glu Leu Lys Gln Gly Gly Thr Leu Arg Glu
    130                 135                 140 gcc gtt ctg cgt gct atc ccg cag ctg cgt ggt gcg tac ggt aca gtg        480
Ala Val Leu Arg Ala Ile Pro Gln Leu Arg Gly Ala Tyr Gly Thr Val
145                 150                 155                 160 atc atg gac tcc cgt cac ccg gat acc ctg ctg gcg gca cgt tct ggt        528
Ile Met Asp Ser Arg His Pro Asp Thr Leu Leu Ala Ala Arg Ser Gly
                165                 170                 175 agt ccg ctg gtg att ggc ctg ggg atg ggc gaa aac ttt atc gct tct        576
Ser Pro Leu Val Ile Gly Leu Gly Met Gly Glu Asn Phe Ile Ala Ser
            180                 185                 190 gac cag ctg gcg ctg ttg ccg gtg acc cgt cgc ttt atc ttc ctt gaa        624
Asp Gln Leu Ala Leu Leu Pro Val Thr Arg Arg Phe Ile Phe Leu Glu
        195                 200                 205 gag ggc gat att gcg gaa atc act cgc cgt tcg gta aac atc ttc gat        672
Glu Gly Asp Ile Ala Glu Ile Thr Arg Arg Ser Val Asn Ile Phe Asp
    210                 215                 220
```

```
                    210                 215                 220
aaa act ggc gcg gaa gta aaa cgt cag gat atc gaa tcc aat ctg caa       720
Lys Thr Gly Ala Glu Val Lys Arg Gln Asp Ile Glu Ser Asn Leu Gln
225                 230                 235                 240 tat gac gcg ggc gat aaa ggc att tac cgt cac tac atg cag aaa gag       768
Tyr Asp Ala Gly Asp Lys Gly Ile Tyr Arg His Tyr Met Gln Lys Glu
                245                 250                 255 atc tac gaa cag ccg aac gcg atc aaa aac acc ctt acc gga cgc acc       816
Ile Tyr Glu Gln Pro Asn Ala Ile Lys Asn Thr Leu Thr Gly Arg Thr
            260                 265                 270 agc cac ggt cag gtt gat tta agc gag ctg gga ccg aac gcc gac gaa       864
Ser His Gly Gln Val Asp Leu Ser Glu Leu Gly Pro Asn Ala Asp Glu
        275                 280                 285 ctg ctg tcg aag gtt gag cat att cag atc ctc gcc tgt ggt act tct       912
Leu Leu Ser Lys Val Glu His Ile Gln Ile Leu Ala Cys Gly Thr Ser
    290                 295                 300 tat aac tcc ggt atg gtt tcc cgc tac tgg ttt gaa tcg cta gca ggt       960
Tyr Asn Ser Gly Met Val Ser Arg Tyr Trp Phe Glu Ser Leu Ala Gly
305                 310                 315                 320 att ccg tgc gac gtc gaa atc gcc tct gaa ttc cgc tat cgc aaa tct      1008
Ile Pro Cys Asp Val Glu Ile Ala Ser Glu Phe Arg Tyr Arg Lys Ser
                325                 330                 335 gcc gtg cgt cgt aac agc ctg atg atc acc ttg tca cag tct ggc gaa      1056
Ala Val Arg Arg Asn Ser Leu Met Ile Thr Leu Ser Gln Ser Gly Glu
            340                 345                 350 acc gcg gat acc ctg gct ggc ctg cgt ctg tcg aaa gag ctg ggt tac      1104
Thr Ala Asp Thr Leu Ala Gly Leu Arg Leu Ser Lys Glu Leu Gly Tyr
        355                 360                 365 ctt ggt tca ctg gca atc tgt aac gtt ccg ggt tct tct ctg gtg cgc      1152
Leu Gly Ser Leu Ala Ile Cys Asn Val Pro Gly Ser Ser Leu Val Arg
    370                 375                 380 gaa tcc gat ctg gcg cta atg acc aac gcg ggt aca gaa atc ggc gtg      1200
Glu Ser Asp Leu Ala Leu Met Thr Asn Ala Gly Thr Glu Ile Gly Val
385                 390                 395                 400 gca tcc act aaa gca ttc acc act cag tta act gtg ctg ttg atg ctg      1248
Ala Ser Thr Lys Ala Phe Thr Thr Gln Leu Thr Val Leu Leu Met Leu
                405                 410                 415 gtg gcg aag ctg tct cgc ctg aaa ggt ctg gat gcc tcc att gaa cat      1296
Val Ala Lys Leu Ser Arg Leu Lys Gly Leu Asp Ala Ser Ile Glu His
            420                 425                 430 gac atc gtg cat ggt ctg cag gcg ctg ccg agc cgt att gag cag atg      1344
Asp Ile Val His Gly Leu Gln Ala Leu Pro Ser Arg Ile Glu Gln Met
        435                 440                 445 ctg cct cag gac aaa cgc att gaa gcg ctg gca gaa gat ttc tct gac      1392
Leu Pro Gln Asp Lys Arg Ile Glu Ala Leu Ala Glu Asp Phe Ser Asp
    450                 455                 460 aaa cat cac gcg ctg ttc ctg ggc cgt ggc gat cag tac cca atc gcg      1440
Lys His His Ala Leu Phe Leu Gly Arg Gly Asp Gln Tyr Pro Ile Ala
465                 470                 475                 480 ctg gaa ggc gca ttg aag ttg aaa gag atc tct tac att cac gct gaa      1488
Leu Glu Gly Ala Leu Lys Leu Lys Glu Ile Ser Tyr Ile His Ala Glu
                485                 490                 495 gcc tac gct gct ggc gaa ctg aaa cac ggt ccg ctg gcg cta att gat      1536
Ala Tyr Ala Ala Gly Glu Leu Lys His Gly Pro Leu Ala Leu Ile Asp
            500                 505                 510 gcc gat atg ccg gtt att gtt gtt gca ccg aac aac gaa ttg ctg gaa      1584
Ala Asp Met Pro Val Ile Val Val Ala Pro Asn Asn Glu Leu Leu Glu
        515                 520                 525 aaa ctg aaa tcc aac att gaa gaa gtt cgc gcg cgt ggc ggt cag ttg      1632
```

-continued

```
Lys Leu Lys Ser Asn Ile Glu Glu Val Arg Ala Arg Gly Gly Gln Leu
            530                 535                 540 tat gtc ttc gcc gat cag gat gcg ggt ttt gta agt agc gat aac atg      1680
Tyr Val Phe Ala Asp Gln Asp Ala Gly Phe Val Ser Ser Asp Asn Met
545                 550                 555                 560 cac atc atc gag atg ccg cat gtg gaa gag gtg att gca ccg atc ttc      1728
His Ile Ile Glu Met Pro His Val Glu Glu Val Ile Ala Pro Ile Phe
                565                 570                 575 tac acc gtt ccg ctg cag ctg ctg gct tac cat gtc gcg ctg atc aaa      1776
Tyr Thr Val Pro Leu Gln Leu Leu Ala Tyr His Val Ala Leu Ile Lys
            580                 585                 590 ggc acc gac gtt gac cag ccg cgt aac ctg gca aaa tcg gtt acg gtt      1824
Gly Thr Asp Val Asp Gln Pro Arg Asn Leu Ala Lys Ser Val Thr Val
        595                 600                 605 gag taa                                                               1830
Glu
```

<210> SEQ ID NO 19
<211> LENGTH: 609
<212> TYPE: PRT
<213> ORGANISM: Escherichia coli

<400> SEQUENCE: 19

```
Met Cys Gly Thr Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
    130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205

Glu Gly Asp Ile Ala Glu Ile Thr Arg Arg Ser Val Asn Ile Phe Asp
    210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Thr
```

```
                    260                 265                 270
        Ser His Gly Gln Val Asp Leu Ser Glu Leu Gly Pro Asn Ala Asp Glu
                275                 280                 285

Leu Leu Ser Lys Val Glu His Ile Gln Ile Leu Ala Cys Gly Thr Ser
            290                 295                 300

Tyr Asn Ser Gly Met Val Ser Arg Tyr Trp Phe Glu Ser Leu Ala Gly
        305                 310                 315                 320

Ile Pro Cys Asp Val Glu Ile Ala Ser Glu Phe Arg Tyr Arg Lys Ser
                        325                 330                 335

Ala Val Arg Arg Asn Ser Leu Met Ile Thr Leu Ser Gln Ser Gly Glu
                    340                 345                 350

Thr Ala Asp Thr Leu Ala Gly Leu Arg Leu Ser Lys Glu Leu Gly Tyr
                355                 360                 365

Leu Gly Ser Leu Ala Ile Cys Asn Val Pro Gly Ser Ser Leu Val Arg
            370                 375                 380

Glu Ser Asp Leu Ala Leu Met Thr Asn Ala Gly Thr Glu Ile Gly Val
        385                 390                 395                 400

Ala Ser Thr Lys Ala Phe Thr Thr Gln Leu Thr Val Leu Leu Met Leu
                        405                 410                 415

Val Ala Lys Leu Ser Arg Leu Lys Gly Leu Asp Ala Ser Ile Glu His
                    420                 425                 430

Asp Ile Val His Gly Leu Gln Ala Leu Pro Ser Arg Ile Glu Gln Met
                435                 440                 445

Leu Pro Gln Asp Lys Arg Ile Glu Ala Leu Ala Glu Asp Phe Ser Asp
            450                 455                 460

Lys His His Ala Leu Phe Leu Gly Arg Gly Asp Gln Tyr Pro Ile Ala
        465                 470                 475                 480

Leu Glu Gly Ala Leu Lys Leu Lys Glu Ile Ser Tyr Ile His Ala Glu
                        485                 490                 495

Ala Tyr Ala Ala Gly Glu Leu Lys His Gly Pro Leu Ala Leu Ile Asp
                    500                 505                 510

Ala Asp Met Pro Val Ile Val Ala Pro Asn Asn Glu Leu Leu Glu
                515                 520                 525

Lys Leu Lys Ser Asn Ile Glu Glu Val Arg Ala Arg Gly Gly Gln Leu
            530                 535                 540

Tyr Val Phe Ala Asp Gln Asp Ala Gly Phe Val Ser Ser Asp Asn Met
        545                 550                 555                 560

His Ile Ile Glu Met Pro His Val Glu Glu Val Ile Ala Pro Ile Phe
                        565                 570                 575

Tyr Thr Val Pro Leu Gln Leu Leu Ala Tyr His Val Ala Leu Ile Lys
                    580                 585                 590

Gly Thr Asp Val Asp Gln Pro Arg Asn Leu Ala Lys Ser Val Thr Val
                595                 600                 605

Glu

<210> SEQ ID NO 20
<211> LENGTH: 2184
<212> TYPE: DNA
<213> ORGANISM: Escherichia coli

<400> SEQUENCE: 20
ccgctctaga actagtggat ctcgatcccg cgaaattaat acgactcact ataggggaat    60
tgtgagcgga taacaattcc cctctagaaa taattttgtt taactttaag aaggagatat   120
```

```
accatgtgtg gaattgttgg cgcgatcgcg caacgtgatg tagcagaaat ccttcttgaa      180
ggtttacgtc gtctggaata ccgcggatat gactctgccg gtctggccgt tgttgataca      240
gaaggtcata tgacccgcct gcgtcgcctc ggtaaagtcc agatgctggc acaggcagcg      300
gaagaacatc ctctgcatgg cggcactggt attgctcaca ctcgctgggc gacccacggt      360
gaaccttcag aagtgaatgc gcatccgcat gtttctgaac acattgtggt ggtgcataac      420
ggcatcatcg aaaaccatga accgctgcgt gaagagctaa agcgcgtgg ctataccttc       480
gtttctgaaa ccgacaccga agtgattgcc catctggtga actgggagct gaaacaaggc      540
gggactctgc gtgaggccgt tctgcgtgct atcccgcagc tgcgtggtgc gtacggtaca      600
gtgatcatgg actcccgtca cccggatacc ctgctggcgg cacgttctgg tagtccgctg      660
gtgattggcc tggggatggg cgaaaacttt atcgcttctg accagctggc gctgttgccg      720
gtgacccgtc gctttatctt ccttgaagag ggcgatattg cggaaatcac tcgccgttcg      780
gtaaacatct tcgataaaac tggcgcggaa gtaaaacgtc aggatatcga atccaatctg      840
caatatgacg cgggcgataa aggcatttac tgtcactaca tgcagaaaga gatctacgaa      900
cagccgaacg cgatcaaaaa cacccttacc ggacgcatca gccacggtca ggttgattta      960
agcgagctgg gaccgaacgc cgacgaactg ctgtcgaagg ttgagcatat tcagatcctc     1020
gcctgtggta cttcttataa ctccggtatg gtttcccgct actggttga atcgctagca      1080
ggtattccgt gcgacgtcga aatcgcctcc gaattccgct atcgcaaatc tgccgtgcgt     1140
cgtaacagcc tgatgatcac cttgtcacag tctggcgaaa ccgcggatac cctggctggc     1200
ctgcgtctgt cgaaagagct gggttacctt ggttcactgg caatctgtaa cgttccgggt     1260
tcttctctgg tgcgcgaatc cgatctggcg ctaatgacca acgcgggtac agaaatcggc     1320
gtggcatcca ctaaagcatt caccactcag ttaactgtgc tgttgatgct ggtggcgaag     1380
ctgtctcgcc tgaaaggtct ggatgcctcc attgaacatg acatcgtgca tggtctgcag     1440
gcgctgccga gccgtattga gcagatgctg tctcaggaca aacgcattga agcgctggca     1500
gaagatttct ctgacaaaca tcacgcgctg ttcctgagcc gtggcgatca gtacccaatc     1560
gcgctggaag gcgcattgaa gttgaaagag atctcttaca ttcacgctga agcctacgct     1620
gctggcgaac tgaaacacgg tccgctggcg ctaattgatg ccgatatgcc ggttattgtt     1680
gttgcaccga caacgaatt gctggaaaaa ctgaaatcca acattgaaga agttcgcgcg      1740
cgtggcggtc agttgtatgt cttcgccgat caggatgcgg ttttgtaag tagcgataac      1800
atgcacatca tcgagatgcc gcatgtggaa gaggtgattg caccgatctt ctacaccgtt     1860
ccgctgcagc tgctggctta ccatgtcgcg ctgatcaaag caccgacgt tgaccagccg      1920
cgtaacctgg caaaatcggt tacggttgag taataaatgg atgccctgcg taagcggggc     1980
attttcttc ctgttatgtt tttaatcaaa catcctgcca actccatgtg acaaccgtc      2040
atcttcggct acttttctc tgtcacagaa tgaaaatttt tctgtcatct cttcgttatt     2100
aatgtttgta attgactgaa tatcaacgct ctaggggggc tagagcggcc gccaccgcgg     2160
tggagctccg tcgacaagct tatc                                           2184
```

<210> SEQ ID NO 21
<211> LENGTH: 1830
<212> TYPE: DNA
<213> ORGANISM: Escherichia coli
<220> FEATURE:
<221> NAME/KEY: CDS
<222> LOCATION: (1)..(1830)

-continued

```
<400> SEQUENCE: 21 atg tgt gga att gtt ggc gcg atc gcg caa cgt gat gta gca gaa atc        48
Met Cys Gly Ile Val Gly Ala Ile Ala Gln Arg Asp Val Ala Glu Ile
 1               5                  10                  15 ctt ctt gaa ggt tta cgt cgt ctg gaa tac cgc gga tat gac tct gcc        96
Leu Leu Glu Gly Leu Arg Arg Leu Glu Tyr Arg Gly Tyr Asp Ser Ala
             20                  25                  30 ggt ctg gcc gtt gtt gat aca gaa ggt cat atg acc cgc ctg cgt cgc       144
Gly Leu Ala Val Val Asp Thr Glu Gly His Met Thr Arg Leu Arg Arg
         35                  40                  45 ctc ggt aaa gtc cag atg ctg gca cag gca gcg gaa gaa cat cct ctg       192
Leu Gly Lys Val Gln Met Leu Ala Gln Ala Ala Glu Glu His Pro Leu
     50                  55                  60 cat ggc ggc act ggt att gct cac act cgc tgg gcg acc cac ggt gaa       240
His Gly Gly Thr Gly Ile Ala His Thr Arg Trp Ala Thr His Gly Glu
 65                  70                  75                  80 cct tca gaa gtg aat gcg cat ccg cat gtt tct gaa cac att gtg gtg       288
Pro Ser Glu Val Asn Ala His Pro His Val Ser Glu His Ile Val Val
                 85                  90                  95 gtg cat aac ggc atc atc gaa aac cat gaa ccg ctg cgt gaa gag cta       336
Val His Asn Gly Ile Ile Glu Asn His Glu Pro Leu Arg Glu Glu Leu
            100                 105                 110 aaa gcg cgt ggc tat acc ttc gtt tct gaa acc gac acc gaa gtg att       384
Lys Ala Arg Gly Tyr Thr Phe Val Ser Glu Thr Asp Thr Glu Val Ile
        115                 120                 125 gcc cat ctg gtg aac tgg gag ctg aaa caa ggc ggg act ctg cgt gag       432
Ala His Leu Val Asn Trp Glu Leu Lys Gln Gly Gly Thr Leu Arg Glu
    130                 135                 140 gcc gtt ctg cgt gct atc ccg cag ctg cgt ggt gcg tac ggt aca gtg       480
Ala Val Leu Arg Ala Ile Pro Gln Leu Arg Gly Ala Tyr Gly Thr Val
145                 150                 155                 160 atc atg gac tcc cgt cac ccg gat acc ctg ctg gcg gca cgt tct ggt       528
Ile Met Asp Ser Arg His Pro Asp Thr Leu Leu Ala Ala Arg Ser Gly
                165                 170                 175 agt ccg ctg gtg att ggc ctg ggg atg ggc gaa aac ttt atc gct tct       576
Ser Pro Leu Val Ile Gly Leu Gly Met Gly Glu Asn Phe Ile Ala Ser
            180                 185                 190 gac cag ctg gcg ctg ttg ccg gtg acc cgt cgc ttt atc ttc ctt gaa       624
Asp Gln Leu Ala Leu Leu Pro Val Thr Arg Arg Phe Ile Phe Leu Glu
        195                 200                 205 gag ggc gat att gcg gaa atc act cgc cgt tcg gta aac atc ttc gat       672
Glu Gly Asp Ile Ala Glu Ile Thr Arg Arg Ser Val Asn Ile Phe Asp
    210                 215                 220 aaa act ggc gcg gaa gta aaa cgt cag gat atc gaa tcc aat ctg caa       720
Lys Thr Gly Ala Glu Val Lys Arg Gln Asp Ile Glu Ser Asn Leu Gln
225                 230                 235                 240 tat gac gcg ggc gat aaa ggc att tac tgt cac tac atg cag aaa gag       768
Tyr Asp Ala Gly Asp Lys Gly Ile Tyr Cys His Tyr Met Gln Lys Glu
                245                 250                 255 atc tac gaa cag ccg aac gcg atc aaa aac acc ctt acc gga cgc atc       816
Ile Tyr Glu Gln Pro Asn Ala Ile Lys Asn Thr Leu Thr Gly Arg Ile
            260                 265                 270 agc cac ggt cag gtt gat tta agc gag ctg gga ccg aac gcc gac gaa       864
Ser His Gly Gln Val Asp Leu Ser Glu Leu Gly Pro Asn Ala Asp Glu
        275                 280                 285 ctg ctg tcg aag gtt gag cat att cag atc ctc gcc tgt ggt act tct       912
Leu Leu Ser Lys Val Glu His Ile Gln Ile Leu Ala Cys Gly Thr Ser
    290                 295                 300 tat aac tcc ggt atg gtt tcc cgc tac tgg ttt gaa tcg cta gca ggt       960
```

-continued

| | | |
|---|---|---|
| Tyr Asn Ser Gly Met Val Ser Arg Tyr Trp Phe Glu Ser Leu Ala Gly<br>305                         310                       315                     320 | | |
| att ccg tgc gac gtc gaa atc gcc tcc gaa ttc cgc tat cgc aaa tct<br>Ile Pro Cys Asp Val Glu Ile Ala Ser Glu Phe Arg Tyr Arg Lys Ser<br>                       325                       330                     335 | 1008 | |
| gcc gtg cgt cgt aac agc ctg atg atc acc ttg tca cag tct ggc gaa<br>Ala Val Arg Arg Asn Ser Leu Met Ile Thr Leu Ser Gln Ser Gly Glu<br>              340                     345                     350 | 1056 | |
| acc gcg gat acc ctg gct ggc ctg cgt ctg tcg aaa gag ctg ggt tac<br>Thr Ala Asp Thr Leu Ala Gly Leu Arg Leu Ser Lys Glu Leu Gly Tyr<br>                 355                     360                     365 | 1104 | |
| ctt ggt tca ctg gca atc tgt aac gtt ccg ggt tct tct ctg gtg cgc<br>Leu Gly Ser Leu Ala Ile Cys Asn Val Pro Gly Ser Ser Leu Val Arg<br>370                         375                       380 | 1152 | |
| gaa tcc gat ctg gcg cta atg acc aac gcg ggt aca gaa atc ggc gtg<br>Glu Ser Asp Leu Ala Leu Met Thr Asn Ala Gly Thr Glu Ile Gly Val<br>385                         390                     395                     400 | 1200 | |
| gca tcc act aaa gca ttc acc act cag tta act gtg ctg ttg atg ctg<br>Ala Ser Thr Lys Ala Phe Thr Thr Gln Leu Thr Val Leu Leu Met Leu<br>                       405                     410                     415 | 1248 | |
| gtg gcg aag ctg tct cgc ctg aaa ggt ctg gat gcc tcc att gaa cat<br>Val Ala Lys Leu Ser Arg Leu Lys Gly Leu Asp Ala Ser Ile Glu His<br>            420                     425                     430 | 1296 | |
| gac atc gtg cat ggt ctg cag gcg ctg ccg agc cgt att gag cag atg<br>Asp Ile Val His Gly Leu Gln Ala Leu Pro Ser Arg Ile Glu Gln Met<br>              435                     440                     445 | 1344 | |
| ctg tct cag gac aaa cgc att gaa gcg ctg gca gaa gat ttc tct gac<br>Leu Ser Gln Asp Lys Arg Ile Glu Ala Leu Ala Glu Asp Phe Ser Asp<br>        450                     455                     460 | 1392 | |
| aaa cat cac gcg ctg ttc ctg agc cgt ggc gat cag tac cca atc gcg<br>Lys His His Ala Leu Phe Leu Ser Arg Gly Asp Gln Tyr Pro Ile Ala<br>465                       470                     475                     480 | 1440 | |
| ctg gaa ggc gca ttg aag ttg aaa gag atc tct tac att cac gct gaa<br>Leu Glu Gly Ala Leu Lys Leu Lys Glu Ile Ser Tyr Ile His Ala Glu<br>                     485                     490                     495 | 1488 | |
| gcc tac gct gct ggc gaa ctg aaa cac ggt ccg ctg gcg cta att gat<br>Ala Tyr Ala Ala Gly Glu Leu Lys His Gly Pro Leu Ala Leu Ile Asp<br>            500                     505                     510 | 1536 | |
| gcc gat atg ccg gtt att gtt gtt gca ccg aac aac gaa ttg ctg gaa<br>Ala Asp Met Pro Val Ile Val Val Ala Pro Asn Asn Glu Leu Leu Glu<br>              515                     520                     525 | 1584 | |
| aaa ctg aaa tcc aac att gaa gaa gtt cgc gcg cgt ggc ggt cag ttg<br>Lys Leu Lys Ser Asn Ile Glu Glu Val Arg Ala Arg Gly Gly Gln Leu<br>530                         535                     540 | 1632 | |
| tat gtc ttc gcc gat cag gat gcg ggt ttt gta agt agc gat aac atg<br>Tyr Val Phe Ala Asp Gln Asp Ala Gly Phe Val Ser Ser Asp Asn Met<br>545                       550                     555                     560 | 1680 | |
| cac atc atc gag atg ccg cat gtg gaa gag gtg att gca ccg atc ttc<br>His Ile Ile Glu Met Pro His Val Glu Glu Val Ile Ala Pro Ile Phe<br>                 565                     570                     575 | 1728 | |
| tac acc gtt ccg ctg cag ctg ctg gct tac cat gtc gcg ctg atc aaa<br>Tyr Thr Val Pro Leu Gln Leu Leu Ala Tyr His Val Ala Leu Ile Lys<br>              580                     585                     590 | 1776 | |
| ggc acc gac gtt gac cag ccg cgt aac ctg gca aaa tcg gtt acg gtt<br>Gly Thr Asp Val Asp Gln Pro Arg Asn Leu Ala Lys Ser Val Thr Val<br>            595                     600                     605 | 1824 | |
| gag taa<br>Glu | 1830 | |

```
<210> SEQ ID NO 22
<211> LENGTH: 609
<212> TYPE: PRT
<213> ORGANISM: Escherichia coli

<400> SEQUENCE: 22

Met Cys Gly Ile Val Gly Ala Ile Ala Gln Arg Asp Val Ala Glu Ile
 1               5                  10                  15

Leu Leu Glu Gly Leu Arg Arg Leu Glu Tyr Arg Gly Tyr Asp Ser Ala
            20                  25                  30

Gly Leu Ala Val Val Asp Thr Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
    130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205

Glu Gly Asp Ile Ala Glu Ile Thr Arg Arg Ser Val Asn Ile Phe Asp
    210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Cys His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
    290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
            340                 345                 350

Thr Ala Asp Thr Leu Ala Gly Leu Arg Leu Ser Lys Glu Leu Gly Tyr
        355                 360                 365

Leu Gly Ser Leu Ala Ile Cys Asn Val Pro Gly Ser Ser Leu Val Arg
    370                 375                 380
```

-continued

```
Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
            405                 410                 415

Val Ala Lys Leu Ser Arg Leu Lys Gly Leu Asp Ala Ser Ile Glu His
        420                 425                 430

Asp Ile Val His Gly Leu Gln Ala Leu Pro Ser Arg Ile Glu Gln Met
    435                 440                 445

Leu Ser Gln Asp Lys Arg Ile Glu Ala Leu Ala Glu Asp Phe Ser Asp
450                 455                 460

Lys His His Ala Leu Phe Leu Ser Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510

Ala Asp Met Pro Val Ile Val Val Ala Pro Asn Asn Glu Leu Leu Glu
        515                 520                 525

Lys Leu Lys Ser Asn Ile Glu Glu Val Arg Ala Arg Gly Gly Gln Leu
    530                 535                 540

Tyr Val Phe Ala Asp Gln Asp Ala Gly Phe Val Ser Ser Asp Asn Met
545                 550                 555                 560

His Ile Ile Glu Met Pro His Val Glu Glu Val Ile Ala Pro Ile Phe
                565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
        595                 600                 605

Glu
```

<210> SEQ ID NO 23
<211> LENGTH: 2184
<212> TYPE: DNA
<213> ORGANISM: Escherichia coli

<400> SEQUENCE: 23

| | | | | | |
|---|---|---|---|---|---|
| ccgctctaga | actagtggat | ctcgatcccg | cgaaattaat | acgactcact | ataggggaat | 60 |
| tgtgagcgga | taacaattcc | cctctagaaa | taattttgtt | taactttaag | aaggagatat | 120 |
| accatgtgtg | gaattgttgg | cgcgatcgcg | caacgtgatg | tagcagaaat | ccttcttgaa | 180 |
| ggtttacgtc | gtctggaata | ccgcggatat | gactctgccg | gtctggccgt | tgttgatgca | 240 |
| gaaggtcata | tgacccgcct | gcgtcgcctc | ggtaaagtcc | agatgctggc | acaggcagcg | 300 |
| gaagaacatc | tctgcatgg | cggcactggt | attgctcaca | ctcgctgggc | gacccacggt | 360 |
| gaaccttcag | aagtgaatgc | gcatccgcat | gtttccgaac | acattgtggt | ggtgcataac | 420 |
| ggcatcatcg | aaaaccatga | accgctgcgt | gaagagctaa | aagcgcgtgg | ctataccttc | 480 |
| gtttctgaaa | ccgacaccga | agtgattgcc | catctggtga | actgggagct | gaaacaaggc | 540 |
| gggactctgc | gtgaggccgt | tctgcgtgct | atcccgcagc | tgcgtggtgc | gtacggtaca | 600 |
| gtgatcatgg | actcccgtca | cccggatacc | ctgctggcgg | cacgttctgg | tagtccgctg | 660 |
| gtgattggcc | tggggatggg | cgaaaacttt | atcgcttctg | accagctggc | gctgttgccg | 720 |
| gtgacccgtc | gctttatctt | ccttgaagag | ggcgatattg | cggaaatcac | tcgccgttcg | 780 |
| gtaaacatct | tcgataaaac | tggcgcggaa | gtaaacgtc | aggatatcga | atccaatctg | 840 |

-continued

```
caatatgacg cgggcgataa aggcatttac cgtcactaca tgcagaaaga gatctacgaa    900
cagccgaacg cgatcaaaaa cacccttacc ggacgcatca gccacggtca ggttgattta    960
agcgagctgg gaccgaacgc cgacgaactg ctgtcgaagg ttgagcatat tcagatcctc   1020
gcctgtggta cttcttataa ctccggtatg gtttcccgct actggtttga atcgctagca   1080
ggtattccgt gcgacgtcga aatcgcctct gaattccgct atcgcaaatc tgccgtgcgt   1140
cgtaacagcc tgatgatcac cttgtcacag tctggcgaaa ccgcggatac cctggctggc   1200
ctgcgtctgt cgaaagagct gggttacctt ggttcactgg caatctgtaa cgttccgggt   1260
tcttctctgg tgcgcgaatc cgatctggcg ctaatgacca acgcgggtac agaaatcggc   1320
gtggcatcca ctaaagcatt caccactcag ttaactgtgc tgttgatgct ggtggcgaag   1380
ctgtctcgcc tgaaaggtct ggatgcctcc attgaacatg acatcgtgca tggtctgcag   1440
gcgctgccga gccgtattga gcagatgctg tctcaggaca aacgcattga agcgctggca   1500
gaagatttct ctgacaaaca tcacgcgccg ttcctgggcc gtggcgatca gtacccaatc   1560
gcgctggaag cgcattgaa gttgaaagag atctcttaca ttcacgctga gcctacgct    1620 gctggcgaac tgaaacacgg tccgctggcg ctaattgatg ccgatatgcc ggttattgtt   1680
gttgcaccga caacgaatt gctggaaaaa ctgaaatcca acattgaaga agttcgcgcg    1740
cgtggcggtc agttgtatgt cttcgccgat caggatgcgg gttttgtaag tagcgataac   1800
atgcacatca tcgagatgcc gcatgtggaa gaggtgattg caccgatctt ctacaccgtt   1860
ccgctgcagc tgctggctta ccatgtcgcg ctgatcaaag gcaccgacgt tgaccagccg   1920
cgtaacctgg caaaatcggt tacggttgag taataaatgg atgccctgcg taagcggggc   1980
atttttcttc ctgttatgtt tttaatcaaa catcctgcca actccatgtg acaaaccgtc   2040
atcttcggct acttttctc tgtcacagaa tgaaaatttt tctgtcatct cttcgttatt    2100
aatgtttgta attgactgaa tatcaacgct ctagagggc tagagcggcc accaccgcgg    2160
tggagctccg tcgacaagct tatc                                          2184
```

<210> SEQ ID NO 24
<211> LENGTH: 1830
<212> TYPE: DNA
<213> ORGANISM: Escherichia coli
<220> FEATURE:
<221> NAME/KEY: CDS
<222> LOCATION: (1)..(1830)

<400> SEQUENCE: 24

```
atg tgt gga att gtt ggc gcg atc gcg caa cgt gat gta gca gaa atc     48
Met Cys Gly Ile Val Gly Ala Ile Ala Gln Arg Asp Val Ala Glu Ile
 1               5                  10                  15 ctt ctt gaa ggt tta cgt cgt ctg gaa tac cgc gga tat gac tct gcc    96
Leu Leu Glu Gly Leu Arg Arg Leu Glu Tyr Arg Gly Tyr Asp Ser Ala
             20                  25                  30 ggt ctg gcc gtt gtt gat gca gaa ggt cat atg acc cgc ctg cgt cgc   144
Gly Leu Ala Val Val Asp Ala Glu Gly His Met Thr Arg Leu Arg Arg
         35                  40                  45 ctc ggt aaa gtc cag atg ctg gca cag gca gcg gaa gaa cat cct ctg   192
Leu Gly Lys Val Gln Met Leu Ala Gln Ala Ala Glu Glu His Pro Leu
     50                  55                  60 cat ggc ggc act ggt att gct cac act cgc tgg gcg acc cac ggt gaa   240
His Gly Gly Thr Gly Ile Ala His Thr Arg Trp Ala Thr His Gly Glu
 65                  70                  75                  80 cct tca gaa gtg aat gcg cat ccg cat gtt tcc gaa cac att gtg gtg   288
```

```
                Pro Ser Glu Val Asn Ala His Pro His Val Ser Glu His Ile Val Val
                                85                  90                  95 gtg cat aac ggc atc atc gaa aac cat gaa ccg ctg cgt gaa gag cta            336
Val His Asn Gly Ile Ile Glu Asn His Glu Pro Leu Arg Glu Glu Leu
            100                 105                 110 aaa gcg cgt ggc tat acc ttc gtt tct gaa acc gac acc gaa gtg att            384
Lys Ala Arg Gly Tyr Thr Phe Val Ser Glu Thr Asp Thr Glu Val Ile
    115                 120                 125 gcc cat ctg gtg aac tgg gag ctg aaa caa ggc ggg act ctg cgt gag            432
Ala His Leu Val Asn Trp Glu Leu Lys Gln Gly Gly Thr Leu Arg Glu
130                 135                 140 gcc gtt ctg cgt gct atc ccg cag ctg cgt ggt gcg tac ggt aca gtg            480
Ala Val Leu Arg Ala Ile Pro Gln Leu Arg Gly Ala Tyr Gly Thr Val
145                 150                 155                 160 atc atg gac tcc cgt cac ccg gat acc ctg ctg gcg gca cgt tct ggt            528
Ile Met Asp Ser Arg His Pro Asp Thr Leu Leu Ala Ala Arg Ser Gly
            165                 170                 175 agt ccg ctg gtg att ggc ctg ggg atg ggc gaa aac ttt atc gct tct            576
Ser Pro Leu Val Ile Gly Leu Gly Met Gly Glu Asn Phe Ile Ala Ser
        180                 185                 190 gac cag ctg gcg ctg ttg ccg gtg acc cgt cgc ttt atc ttc ctt gaa            624
Asp Gln Leu Ala Leu Leu Pro Val Thr Arg Arg Phe Ile Phe Leu Glu
            195                 200                 205 gag ggc gat att gcg gaa atc act cgc cgt tcg gta aac atc ttc gat            672
Glu Gly Asp Ile Ala Glu Ile Thr Arg Arg Ser Val Asn Ile Phe Asp
210                 215                 220 aaa act ggc gcg gaa gta aaa cgt cag gat atc gaa tcc aat ctg caa            720
Lys Thr Gly Ala Glu Val Lys Arg Gln Asp Ile Glu Ser Asn Leu Gln
225                 230                 235                 240 tat gac gcg ggc gat aaa ggc att tac cgt cac tac atg cag aaa gag            768
Tyr Asp Ala Gly Asp Lys Gly Ile Tyr Arg His Tyr Met Gln Lys Glu
            245                 250                 255 atc tac gaa cag ccg aac gcg atc aaa aac acc ctt acc gga cgc atc            816
Ile Tyr Glu Gln Pro Asn Ala Ile Lys Asn Thr Leu Thr Gly Arg Ile
            260                 265                 270 agc cac ggt cag gtt gat tta agc gag ctg gga ccg aac gcc gac gaa            864
Ser His Gly Gln Val Asp Leu Ser Glu Leu Gly Pro Asn Ala Asp Glu
        275                 280                 285 ctg ctg tcg aag gtt gag cat att cag atc ctc gcc tgt ggt act tct            912
Leu Leu Ser Lys Val Glu His Ile Gln Ile Leu Ala Cys Gly Thr Ser
        290                 295                 300 tat aac tcc ggt atg gtt tcc cgc tac tgg ttt gaa tcg cta gca ggt            960
Tyr Asn Ser Gly Met Val Ser Arg Tyr Trp Phe Glu Ser Leu Ala Gly
305                 310                 315                 320 att ccg tgc gac gtc gaa atc gcc tct gaa ttc cgc tat cgc aaa tct           1008
Ile Pro Cys Asp Val Glu Ile Ala Ser Glu Phe Arg Tyr Arg Lys Ser
            325                 330                 335 gcc gtg cgt cgt aac agc ctg atg atc acc ttg tca cag tct ggc gaa           1056
Ala Val Arg Arg Asn Ser Leu Met Ile Thr Leu Ser Gln Ser Gly Glu
            340                 345                 350 acc gcg gat acc ctg gct ggc ctg cgt ctg tcg aaa gag ctg ggt tac           1104
Thr Ala Asp Thr Leu Ala Gly Leu Arg Leu Ser Lys Glu Leu Gly Tyr
        355                 360                 365 ctt ggt tca ctg gca atc tgt aac gtt ccg ggt tct tct ctg gtg cgc           1152
Leu Gly Ser Leu Ala Ile Cys Asn Val Pro Gly Ser Ser Leu Val Arg
    370                 375                 380 gaa tcc gat ctg gcg cta atg acc aac gcg ggt aca gaa atc ggc gtg           1200
Glu Ser Asp Leu Ala Leu Met Thr Asn Ala Gly Thr Glu Ile Gly Val
385                 390                 395                 400
```

```
gca tcc act aaa gca ttc acc act cag tta act gtg ctg ttg atg ctg    1248
Ala Ser Thr Lys Ala Phe Thr Thr Gln Leu Thr Val Leu Leu Met Leu
            405                 410                 415 gtg gcg aag ctg tct cgc ctg aaa ggt ctg gat gcc tcc att gaa cat    1296
Val Ala Lys Leu Ser Arg Leu Lys Gly Leu Asp Ala Ser Ile Glu His
            420                 425                 430 gac atc gtg cat ggt ctg cag gcg ctg ccg agc cgt att gag cag atg    1344
Asp Ile Val His Gly Leu Gln Ala Leu Pro Ser Arg Ile Glu Gln Met
            435                 440                 445 ctg tct cag gac aaa cgc att gaa gcg ctg gca gaa gat ttc tct gac    1392
Leu Ser Gln Asp Lys Arg Ile Glu Ala Leu Ala Glu Asp Phe Ser Asp
        450                 455                 460 aaa cat cac gcg ccg ttc ctg ggc cgt ggc gat cag tac cca atc gcg    1440
Lys His His Ala Pro Phe Leu Gly Arg Gly Asp Gln Tyr Pro Ile Ala
465                 470                 475                 480 ctg gaa ggc gca ttg aag ttg aaa gag atc tct tac att cac gct gaa    1488
Leu Glu Gly Ala Leu Lys Leu Lys Glu Ile Ser Tyr Ile His Ala Glu
                485                 490                 495 gcc tac gct gct ggc gaa ctg aaa cac ggt ccg ctg gcg cta att gat    1536
Ala Tyr Ala Ala Gly Glu Leu Lys His Gly Pro Leu Ala Leu Ile Asp
                500                 505                 510 gcc gat atg ccg gtt att gtt gtt gca ccg aac aac gaa ttg ctg gaa    1584
Ala Asp Met Pro Val Ile Val Val Ala Pro Asn Asn Glu Leu Leu Glu
            515                 520                 525 aaa ctg aaa tcc aac att gaa gaa gtt cgc gcg cgt ggc ggt cag ttg    1632
Lys Leu Lys Ser Asn Ile Glu Glu Val Arg Ala Arg Gly Gly Gln Leu
        530                 535                 540 tat gtc ttc gcc gat cag gat gcg ggt ttt gta agt agc gat aac atg    1680
Tyr Val Phe Ala Asp Gln Asp Ala Gly Phe Val Ser Ser Asp Asn Met
545                 550                 555                 560 cac atc atc gag atg ccg cat gtg gaa gag gtg att gca ccg atc ttc    1728
His Ile Ile Glu Met Pro His Val Glu Glu Val Ile Ala Pro Ile Phe
                565                 570                 575 tac acc gtt ccg ctg cag ctg ctg gct tac cat gtc gcg ctg atc aaa    1776
Tyr Thr Val Pro Leu Gln Leu Leu Ala Tyr His Val Ala Leu Ile Lys
                580                 585                 590 ggc acc gac gtt gac cag ccg cgt aac ctg gca aaa tcg gtt acg gtt    1824
Gly Thr Asp Val Asp Gln Pro Arg Asn Leu Ala Lys Ser Val Thr Val
            595                 600                 605 gag taa                                                            1830
Glu

<210> SEQ ID NO 25
<211> LENGTH: 609
<212> TYPE: PRT
<213> ORGANISM: Escherichia coli

<400> SEQUENCE: 25

Met Cys Gly Ile Val Gly Ala Ile Ala Gln Arg Asp Val Ala Glu Ile
  1               5                  10                  15

Leu Leu Glu Gly Leu Arg Arg Leu Glu Tyr Arg Gly Tyr Asp Ser Ala
             20                  25                  30

Gly Leu Ala Val Val Asp Ala Glu Gly His Met Thr Arg Leu Arg Arg
         35                  40                  45

Leu Gly Lys Val Gln Met Leu Ala Gln Ala Ala Glu Glu His Pro Leu
     50                  55                  60

His Gly Gly Thr Gly Ile Ala His Thr Arg Trp Ala Thr His Gly Glu
 65                  70                  75                  80

Pro Ser Glu Val Asn Ala His Pro His Val Ser Glu His Ile Val Val
```

```
                        85                  90                  95
Val His Asn Gly Ile Ile Glu Asn His Glu Pro Leu Arg Glu Glu Leu
                100                 105                 110
Lys Ala Arg Gly Tyr Thr Phe Val Ser Glu Thr Asp Thr Glu Val Ile
                115                 120                 125
Ala His Leu Val Asn Trp Glu Leu Lys Gln Gly Gly Thr Leu Arg Glu
            130                 135                 140
Ala Val Leu Arg Ala Ile Pro Gln Leu Arg Gly Ala Tyr Gly Thr Val
145                 150                 155                 160
Ile Met Asp Ser Arg His Pro Asp Thr Leu Leu Ala Ala Arg Ser Gly
                165                 170                 175
Ser Pro Leu Val Ile Gly Leu Gly Met Gly Glu Asn Phe Ile Ala Ser
            180                 185                 190
Asp Gln Leu Ala Leu Leu Pro Val Thr Arg Arg Phe Ile Phe Leu Glu
            195                 200                 205
Glu Gly Asp Ile Ala Glu Ile Thr Arg Arg Ser Val Asn Ile Phe Asp
        210                 215                 220
Lys Thr Gly Ala Glu Val Lys Arg Gln Asp Ile Glu Ser Asn Leu Gln
225                 230                 235                 240
Tyr Asp Ala Gly Asp Lys Gly Ile Tyr Arg His Tyr Met Gln Lys Glu
                245                 250                 255
Ile Tyr Glu Gln Pro Asn Ala Ile Lys Asn Thr Leu Thr Gly Arg Ile
                260                 265                 270
Ser His Gly Gln Val Asp Leu Ser Glu Leu Gly Pro Asn Ala Asp Glu
            275                 280                 285
Leu Leu Ser Lys Val Glu His Ile Gln Ile Leu Ala Cys Gly Thr Ser
        290                 295                 300
Tyr Asn Ser Gly Met Val Ser Arg Tyr Trp Phe Glu Ser Leu Ala Gly
305                 310                 315                 320
Ile Pro Cys Asp Val Glu Ile Ala Ser Glu Phe Arg Tyr Arg Lys Ser
                325                 330                 335
Ala Val Arg Arg Asn Ser Leu Met Ile Thr Leu Ser Gln Ser Gly Glu
            340                 345                 350
Thr Ala Asp Thr Leu Ala Gly Leu Arg Leu Ser Lys Glu Leu Gly Tyr
            355                 360                 365
Leu Gly Ser Leu Ala Ile Cys Asn Val Pro Gly Ser Ser Leu Val Arg
        370                 375                 380
Glu Ser Asp Leu Ala Leu Met Thr Asn Ala Gly Thr Glu Ile Gly Val
385                 390                 395                 400
Ala Ser Thr Lys Ala Phe Thr Thr Gln Leu Thr Val Leu Leu Met Leu
                405                 410                 415
Val Ala Lys Leu Ser Arg Leu Lys Gly Leu Asp Ala Ser Ile Glu His
            420                 425                 430
Asp Ile Val His Gly Leu Gln Ala Leu Pro Ser Arg Ile Glu Gln Met
        435                 440                 445
Leu Ser Gln Asp Lys Arg Ile Glu Ala Leu Ala Glu Asp Phe Ser Asp
    450                 455                 460
Lys His His Ala Pro Phe Leu Gly Arg Gly Asp Gln Tyr Pro Ile Ala
465                 470                 475                 480
Leu Glu Gly Ala Leu Lys Leu Lys Glu Ile Ser Tyr Ile His Ala Glu
                485                 490                 495
Ala Tyr Ala Ala Gly Glu Leu Lys His Gly Pro Leu Ala Leu Ile Asp
                500                 505                 510
```

```
Ala Asp Met Pro Val Ile Val Ala Pro Asn Asn Glu Leu Leu Glu
        515                 520                 525

Lys Leu Lys Ser Asn Ile Glu Glu Val Arg Ala Arg Gly Gly Gln Leu
    530                 535                 540

Tyr Val Phe Ala Asp Gln Asp Ala Gly Phe Val Ser Ser Asp Asn Met
545                 550                 555                 560

His Ile Ile Glu Met Pro His Val Glu Val Ile Ala Pro Ile Phe
                565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
            595                 600                 605

Glu

<210> SEQ ID NO 26
<211> LENGTH: 2184
<212> TYPE: DNA
<213> ORGANISM: Escherichia coli

<400> SEQUENCE: 26
ccgctctaga actagtggat ctcgatcccg cgaaattaat acgactcact atagggaat       60 tgtgagcgga taacaattcc cctctagaaa taattttgtt taactttaag aaggagatat    120
accatgtgtg gaattgttgg cgcgatcgcg caacgtgatg tagcagaaat ccttcttgaa    180
ggtttacgtc gtctggaata ccgcggatat gactctgccg gtctggccgt tgttgatgca    240
gaaggtcata tgacccgcct gcgtcgcctc ggtaaagtcc agatgctggc acaggcagcg    300
gaagaacatc ctctgcatgg cggcactggt attgctcaca ctcgctgggc gacccacggt    360
gaaccttcag aagtgaatgc gcatccgcat gtttctgaac acattgtggt ggtgcataac    420
ggcatcatcg aaaaccatga accgctgcgt gaagagctaa agcgcgtgg ctataccttc    480 gtttctgaaa ccgacaccga agtgattgcc catctggtga actgggagct gaaacaaggc    540
gggactctgc gtgaggccgt tctgcgtgct atcccgcagc tgcgtggtgc gtacggtaca    600
gtgatcatgg actcccgtca cccggatacc ctgctggcgg cacgttctgg tagtccgctg    660
gtgattggcc tggggatggg cgaaaacttt atcgcttctg accagctggc gctgttgccg    720
gtgacccgtc gctttatctt ccttgaagag ggcgatattg cggaaatcac tcgccgttcg    780
gtaaacatct tcgataaaac tggcgcggaa gtaaaacgtc aggatatcga atccaatctg    840
caatatgacg cgggcgataa aggcatttac cgtcactaca tgcagaaaga gatctacgaa    900
cagccgaacg cgatcaaaaa caccccttacc ggacgcatca gccacggtca ggttgattta    960
agcgagctgg accgaacgc cgacgaactg ctgtcgaagg ttgagcatat tcagatcctc   1020
gcctgtggta cttcttataa ctccggtatg gtttcccgct actggtttga atcgctagca   1080
ggtattccgt gcgacgtcga aatcgcctct gaattccgct atcgcaaatc tgccgtgcgt   1140
cgtaacagcc tgatgatcac cttgtcacag tctggcgaaa ccgcggatac cctggctggc   1200
ctgcgtctgt cgaaagagct gggttacctt ggttcactgg caatctgtaa cgttccgggt   1260
tcttctctgg tgcgcgaatc cgatctggcg ctaatgacca acgcgggtac agaaatcggc   1320
gtggcatcca ctaaagcatt caccactcag ttaactgtgc tgttgatgct ggtggcgaag   1380
ctgtctcgcc tgaaaggtct ggatgcctcc attgaacatg acatcgtgca tggtctgcag   1440
gcgctgccga gccgtattga gcagatgctg tctcaggaca aacgcattga agcgctggca   1500
```

-continued

```
gaagatttct ctgacaaaca tcacgcgctg ttcctgagcc gtggcgatca gtacccaatc    1560
gcgctggaag gcgcattgaa gttgaaagag atctcttaca ttcacgctga agcctacgct    1620
gctggcgaac tgaaacacgg tccgctggcg ctaattgatg ccgatatgcc ggttattgtt    1680
gttgcaccga caacgaatt gctggaaaaa ctgaaatcca acattgaaga agttcgcgcg    1740
cgtggcggtc agttgtatgt cttcgccgat caggatgcgg ttttgtaag tagcgataac    1800 atgcacatca tcgagatgcc gcatgtggaa gaggtgattg caccgatctt ctacaccgtt    1860
ccgctgcagc tgctggctta ccatgtcgcg ctgatcaaag gcaccgacgt tgaccagccg    1920
cgtaacctgg caaaatcggt tacggttgag taataaatgg atgccctgcg taagcggggc    1980 attttttcttc ctgttatgtt tttaatcaaa catcctgcca actccatgtg acaaaccgtc    2040
atcttcggct actttttctc tgtcacagaa tgaaaatttt tctgtcatct cttcgttatt    2100
aatgtttgta attgactgaa tatcaacgct ctagggggc tagagcggcc gccaccgcgg    2160
tggagctccg tcgacaagct tatc                                          2184
```

<210> SEQ ID NO 27
<211> LENGTH: 1830
<212> TYPE: DNA
<213> ORGANISM: Escherichia coli
<220> FEATURE:
<221> NAME/KEY: CDS
<222> LOCATION: (1)..(1830)

<400> SEQUENCE: 27

```
atg tgt gga att gtt ggc gcg atc gcg caa cgt gat gta gca gaa atc      48
Met Cys Gly Ile Val Gly Ala Ile Ala Gln Arg Asp Val Ala Glu Ile
 1               5                  10                  15 ctt ctt gaa ggt tta cgt cgt ctg gaa tac cgc gga tat gac tct gcc     96
Leu Leu Glu Gly Leu Arg Arg Leu Glu Tyr Arg Gly Tyr Asp Ser Ala
            20                  25                  30 ggt ctg gcc gtt gtt gat gca gaa ggt cat atg acc cgc ctg cgt cgc    144
Gly Leu Ala Val Val Asp Ala Glu Gly His Met Thr Arg Leu Arg Arg
        35                  40                  45 ctc ggt aaa gtc cag atg ctg gca cag gca gcg gaa gaa cat cct ctg    192
Leu Gly Lys Val Gln Met Leu Ala Gln Ala Ala Glu Glu His Pro Leu
    50                  55                  60 cat ggc ggc act ggt att gct cac act cgc tgg gcg acc cac ggt gaa    240
His Gly Gly Thr Gly Ile Ala His Thr Arg Trp Ala Thr His Gly Glu
65                  70                  75                  80 cct tca gaa gtg aat gcg cat ccg cat gtt tct gaa cac att gtg gtg    288
Pro Ser Glu Val Asn Ala His Pro His Val Ser Glu His Ile Val Val
                85                  90                  95 gtg cat aac ggc atc atc gaa aac cat gaa ccg ctg cgt gaa gag cta    336
Val His Asn Gly Ile Ile Glu Asn His Glu Pro Leu Arg Glu Glu Leu
            100                 105                 110 aaa gcg cgt ggc tat acc ttc gtt tct gaa acc gac acc gaa gtg att    384
Lys Ala Arg Gly Tyr Thr Phe Val Ser Glu Thr Asp Thr Glu Val Ile
        115                 120                 125 gcc cat ctg gtg aac tgg gag ctg aaa caa ggc ggg act ctg cgt gag    432
Ala His Leu Val Asn Trp Glu Leu Lys Gln Gly Gly Thr Leu Arg Glu
    130                 135                 140 gcc gtt ctg cgt gct atc ccg cag ctg cgt ggt gcg tac ggt aca gtg    480
Ala Val Leu Arg Ala Ile Pro Gln Leu Arg Gly Ala Tyr Gly Thr Val
145                 150                 155                 160 atc atg gac tcc cgt cac ccg gat acc ctg ctg gcg gca cgt tct ggt    528
Ile Met Asp Ser Arg His Pro Asp Thr Leu Leu Ala Ala Arg Ser Gly
                165                 170                 175
```

```
agt ccg ctg gtg att ggc ctg ggg atg ggc gaa aac ttt atc gct tct      576
Ser Pro Leu Val Ile Gly Leu Gly Met Gly Glu Asn Phe Ile Ala Ser
        180                 185                 190 gac cag ctg gcg ctg ttg ccg gtg acc cgt cgc ttt atc ttc ctt gaa      624
Asp Gln Leu Ala Leu Leu Pro Val Thr Arg Arg Phe Ile Phe Leu Glu
        195                 200                 205 gag ggc gat att gcg gaa atc act cgc cgt tcg gta aac atc ttc gat      672
Glu Gly Asp Ile Ala Glu Ile Thr Arg Arg Ser Val Asn Ile Phe Asp
    210                 215                 220 aaa act ggc gcg gaa gta aaa cgt cag gat atc gaa tcc aat ctg caa      720
Lys Thr Gly Ala Glu Val Lys Arg Gln Asp Ile Glu Ser Asn Leu Gln
225                 230                 235                 240 tat gac gcg ggc gat aaa ggc att tac cgt cac tac atg cag aaa gag      768
Tyr Asp Ala Gly Asp Lys Gly Ile Tyr Arg His Tyr Met Gln Lys Glu
                245                 250                 255 atc tac gaa cag ccg aac gcg atc aaa aac acc ctt acc gga cgc atc      816
Ile Tyr Glu Gln Pro Asn Ala Ile Lys Asn Thr Leu Thr Gly Arg Ile
            260                 265                 270 agc cac ggt cag gtt gat tta agc gag ctg gga ccg aac gcc gac gaa      864
Ser His Gly Gln Val Asp Leu Ser Glu Leu Gly Pro Asn Ala Asp Glu
        275                 280                 285 ctg ctg tcg aag gtt gag cat att cag atc ctc gcc tgt ggt act tct      912
Leu Leu Ser Lys Val Glu His Ile Gln Ile Leu Ala Cys Gly Thr Ser
    290                 295                 300 tat aac tcc ggt atg gtt tcc cgc tac tgg ttt gaa tcg cta gca ggt      960
Tyr Asn Ser Gly Met Val Ser Arg Tyr Trp Phe Glu Ser Leu Ala Gly
305                 310                 315                 320 att ccg tgc gac gtc gaa atc gcc tct gaa ttc cgc tat cgc aaa tct     1008
Ile Pro Cys Asp Val Glu Ile Ala Ser Glu Phe Arg Tyr Arg Lys Ser
                325                 330                 335 gcc gtg cgt cgt aac agc ctg atg atc acc ttg tca cag tct ggc gaa     1056
Ala Val Arg Arg Asn Ser Leu Met Ile Thr Leu Ser Gln Ser Gly Glu
            340                 345                 350 acc gcg gat acc ctg gct ggc ctg cgt ctg tcg aaa gag ctg ggt tac     1104
Thr Ala Asp Thr Leu Ala Gly Leu Arg Leu Ser Lys Glu Leu Gly Tyr
        355                 360                 365 ctt ggt tca ctg gca atc tgt aac gtt ccg ggt tct tct ctg gtg cgc     1152
Leu Gly Ser Leu Ala Ile Cys Asn Val Pro Gly Ser Ser Leu Val Arg
    370                 375                 380 gaa tcc gat ctg gcg cta atg acc aac gcg ggt aca gaa atc ggc gtg     1200
Glu Ser Asp Leu Ala Leu Met Thr Asn Ala Gly Thr Glu Ile Gly Val
385                 390                 395                 400 gca tcc act aaa gca ttc acc act cag tta act gtg ctg ttg atg ctg     1248
Ala Ser Thr Lys Ala Phe Thr Thr Gln Leu Thr Val Leu Leu Met Leu
                405                 410                 415 gtg gcg aag ctg tct cgc ctg aaa ggt ctg gat gcc tcc att gaa cat     1296
Val Ala Lys Leu Ser Arg Leu Lys Gly Leu Asp Ala Ser Ile Glu His
            420                 425                 430 gac atc gtg cat ggt ctg cag gcg ctg ccg agc cgt att gag cag atg     1344
Asp Ile Val His Gly Leu Gln Ala Leu Pro Ser Arg Ile Glu Gln Met
        435                 440                 445 ctg tct cag gac aaa cgc att gaa gcg ctg gca gaa gat ttc tct gac     1392
Leu Ser Gln Asp Lys Arg Ile Glu Ala Leu Ala Glu Asp Phe Ser Asp
    450                 455                 460 aaa cat cac gcg ctg ttc ctg agc cgt ggc gat cag tac cca atc gcg     1440
Lys His His Ala Leu Phe Leu Ser Arg Gly Asp Gln Tyr Pro Ile Ala
465                 470                 475                 480 ctg gaa ggc gca ttg aag ttg aaa gag atc tct tac att cac gct gaa     1488
Leu Glu Gly Ala Leu Lys Leu Lys Glu Ile Ser Tyr Ile His Ala Glu
                485                 490                 495
```

-continued

```
gcc tac gct gct ggc gaa ctg aaa cac ggt ccg ctg gcg cta att gat    1536
Ala Tyr Ala Ala Gly Glu Leu Lys His Gly Pro Leu Ala Leu Ile Asp
            500                 505                 510 gcc gat atg ccg gtt att gtt gtt gca ccg aac aac gaa ttg ctg gaa    1584
Ala Asp Met Pro Val Ile Val Val Ala Pro Asn Asn Glu Leu Leu Glu
                515                 520                 525 aaa ctg aaa tcc aac att gaa gaa gtt cgc gcg cgt ggc ggt cag ttg    1632
Lys Leu Lys Ser Asn Ile Glu Glu Val Arg Ala Arg Gly Gly Gln Leu
        530                 535                 540 tat gtc ttc gcc gat cag gat gcg ggt ttt gta agt agc gat aac atg    1680
Tyr Val Phe Ala Asp Gln Asp Ala Gly Phe Val Ser Ser Asp Asn Met
545                 550                 555                 560 cac atc atc gag atg ccg cat gtg gaa gag gtg att gca ccg atc ttc    1728
His Ile Ile Glu Met Pro His Val Glu Glu Val Ile Ala Pro Ile Phe
                565                 570                 575 tac acc gtt ccg ctg cag ctg ctg gct tac cat gtc gcg ctg atc aaa    1776
Tyr Thr Val Pro Leu Gln Leu Leu Ala Tyr His Val Ala Leu Ile Lys
                580                 585                 590 ggc acc gac gtt gac cag ccg cgt aac ctg gca aaa tcg gtt acg gtt    1824
Gly Thr Asp Val Asp Gln Pro Arg Asn Leu Ala Lys Ser Val Thr Val
            595                 600                 605 gag taa                                                            1830
Glu
```

<210> SEQ ID NO 28
<211> LENGTH: 609
<212> TYPE: PRT
<213> ORGANISM: Escherichia coli

<400> SEQUENCE: 28

```
Met Cys Gly Ile Val Gly Ala Ile Ala Gln Arg Asp Val Ala Glu Ile
 1               5                  10                  15

Leu Leu Glu Gly Leu Arg Arg Leu Glu Tyr Arg Gly Tyr Asp Ser Ala
                20                  25                  30

Gly Leu Ala Val Val Asp Ala Glu Gly His Met Thr Arg Leu Arg Arg
            35                  40                  45

Leu Gly Lys Val Gln Met Leu Ala Gln Ala Ala Glu Glu His Pro Leu
        50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
    130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205
```

```
Glu Gly Asp Ile Ala Glu Ile Thr Arg Arg Ser Val Asn Ile Phe Asp
    210                 215                 220
Lys Thr Gly Ala Glu Val Lys Arg Gln Asp Ile Glu Ser Asn Leu Gln
225                 230                 235                 240
Tyr Asp Ala Gly Asp Lys Gly Ile Tyr Arg His Tyr Met Gln Lys Glu
                245                 250                 255
Ile Tyr Glu Gln Pro Asn Ala Ile Lys Asn Thr Leu Thr Gly Arg Ile
            260                 265                 270
Ser His Gly Gln Val Asp Leu Ser Glu Leu Gly Pro Asn Ala Asp Glu
        275                 280                 285
Leu Leu Ser Lys Val Glu His Ile Gln Ile Leu Ala Cys Gly Thr Ser
    290                 295                 300
Tyr Asn Ser Gly Met Val Ser Arg Tyr Trp Phe Glu Ser Leu Ala Gly
305                 310                 315                 320
Ile Pro Cys Asp Val Glu Ile Ala Ser Glu Phe Arg Tyr Arg Lys Ser
                325                 330                 335
Ala Val Arg Arg Asn Ser Leu Met Ile Thr Leu Ser Gln Ser Gly Glu
            340                 345                 350
Thr Ala Asp Thr Leu Ala Gly Leu Arg Leu Ser Lys Glu Leu Gly Tyr
        355                 360                 365
Leu Gly Ser Leu Ala Ile Cys Asn Val Pro Gly Ser Ser Leu Val Arg
    370                 375                 380
Glu Ser Asp Leu Ala Leu Met Thr Asn Ala Gly Thr Glu Ile Gly Val
385                 390                 395                 400
Ala Ser Thr Lys Ala Phe Thr Thr Gln Leu Thr Val Leu Leu Met Leu
                405                 410                 415
Val Ala Lys Leu Ser Arg Leu Lys Gly Leu Asp Ala Ser Ile Glu His
            420                 425                 430
Asp Ile Val His Gly Leu Gln Ala Leu Pro Ser Arg Ile Glu Gln Met
        435                 440                 445
Leu Ser Gln Asp Lys Arg Ile Glu Ala Leu Ala Glu Asp Phe Ser Asp
    450                 455                 460
Lys His His Ala Leu Phe Leu Ser Arg Gly Asp Gln Tyr Pro Ile Ala
465                 470                 475                 480
Leu Glu Gly Ala Leu Lys Leu Lys Glu Ile Ser Tyr Ile His Ala Glu
                485                 490                 495
Ala Tyr Ala Ala Gly Glu Leu Lys His Gly Pro Leu Ala Leu Ile Asp
            500                 505                 510
Ala Asp Met Pro Val Ile Val Val Ala Pro Asn Asn Glu Leu Leu Glu
        515                 520                 525
Lys Leu Lys Ser Asn Ile Glu Glu Val Arg Ala Arg Gly Gly Gln Leu
    530                 535                 540
Tyr Val Phe Ala Asp Gln Asp Ala Gly Phe Val Ser Ser Asp Asn Met
545                 550                 555                 560
His Ile Ile Glu Met Pro His Val Glu Val Ile Ala Pro Ile Phe
                565                 570                 575
Tyr Thr Val Pro Leu Gln Leu Leu Ala Tyr His Val Ala Leu Ile Lys
            580                 585                 590
Gly Thr Asp Val Asp Gln Pro Arg Asn Leu Ala Lys Ser Val Thr Val
        595                 600                 605
Glu

<210> SEQ ID NO 29
```

<211> LENGTH: 2184
<212> TYPE: DNA
<213> ORGANISM: Escherichia coli

<400> SEQUENCE: 29

```
ccgctctaga actagtggat ctcgatcccg cgaaattaat acgactcact atagggaat       60
tgtgagcgga taacaattcc cctctagaaa taattttgtt taactttaag aaggagatat     120
accatgtgtg gaattgttgg cgcgatcgcg caacgtgatg tagcagaaat ccttcttgaa     180
ggtttacgtc gtctggaata ccgcggatat gactctgccg gtctggccgt tgttgatgca     240
gaaggtcata tgacccgcct gcgtcgcctc ggtaaagtcc agatgctggc acaggcagcg     300
gaagaacatc ctctgcatgg cggcactggt attgctcaca ctcgctgggc gacccacggt     360
gaaccttcag aagtgaatgc gcatccgcat gtttctgaac acattgtggt ggtgcataac     420
ggcatcatcg aaaaccatga accgctgcgt gaagagctaa agcgcgtgg ctataccttc      480
gtttctgaaa ccgacaccga agtgattgcc catctggtga actgggagct gaaacaaggc     540
gggactctgc gtgaggccgt tctgcgtgct atcccgcagc tgcgtggtgc gtacggtaca     600
gtgatcatgg actcccgtca cccggatacc ctgctggcgg cacgttctgg tagtccgctg     660
gtgattggcc tggggatggg cgaaaacttt atcgcttctg accagctggc gctgttgccg     720
gtgacccgtc gctttatctt ccttgaagag ggcgatattg cggaaatcac tcgccgttcg     780
gtaaacatct tcgataaaac tggcgcggaa gtaaaacgtc aggatatcga atccaatctg     840
caatatgacg cgggcgataa aggcatttac cgtcactaca tgcagaaaga gatctacgaa     900
cagccgaacg cgatcaaaaa cacccttacc ggacgcatca gccacggtca ggttgattta     960
agcgagctgg gaccgaacgc cgacgaactg ctgtcgaagg ttgagcatat tcagatcctc    1020
gcctgtggta cttcttataa ctccggtatg gtttcccgct actggtttga atcgctagca    1080
ggtattccgt gcgacgtcga aatcgcctct gaattccgct atcgcaaatc tgccgtgcgt    1140
cgtaacagcc tgatgatcac cttgtcacag tctggcgaaa ccgcggatac cctggctggc    1200
ctgcgtctgt cgaaagagct gggttacctt ggttcactgg caatctgtaa cgttccgggt    1260
tcttctctgg tgcgcgaatc cgatctggcg ctaatgacca acgcgggtac agaaatcggc    1320
gtggcatcca ctaaagcatt caccactcag ttaactgtgc tgttgatgct ggtggcgaag    1380
ctgtctcgcc tgaaaggtct ggatgcctcc attgaacatg acatcgtgca tggtctgcag    1440
gcgctgccga gccgtattga gcagatgctg tctcaggaca aacgcattga agcgctggca    1500
gaagatttct ctgacaaaca tcacgcgctg ttcctgagcc gtggcgatca gtacccaatc    1560
gcgctggaag gcgcattgaa gttgaaagag atctcttaca ttcacgctga agcctacgct    1620
gctggcgaac tgaaacacgg tccgctggcg ctaattgatg ccgatatgcc ggttattgtt    1680
gttgcaccga caacgaatt gctggaaaaa ctgaaatcca acattgaaga gttcgcgcg     1740
cgtggcggtc agttgtatgt cttcgccgat caggatgcgg gttttgtaag tagcgataac    1800
atgcacatca tcgagatgcc gcatgtgaa gaggtgattg caccgatctt ctacaccgtt     1860
ccgctgcagc tgctggctta ccatgtcgcg ctgatcaaag gcaccgacgt tgaccagccg    1920
cgtaacctgg caaatcggt tacgttgag taataaatgg atgccctgcg taagcggggc      1980
atttttcttc ctgttatgtt tttaatcaaa catcctgcca actccatgtg acaaaccgtc    2040
atcttcggct actttttctc tgtcacagaa tgaaattttt tctgtcatct cttcgttatt    2100
aatgtttgta attgactgaa tatcaacgct ctaggggggc tagagcggcc gccaccgcgg    2160
tggagctccg tcgacaagct tatc                                           2184
```

<210> SEQ ID NO 30
<211> LENGTH: 1830
<212> TYPE: DNA
<213> ORGANISM: Escherichia coli
<220> FEATURE:
<221> NAME/KEY: CDS
<222> LOCATION: (1)..(1830)

<400> SEQUENCE: 30

| | | |
|---|---|---|
| atg tgt gga att gtt ggc gcg atc gcg caa cgt gat gta gca gaa atc<br>Met Cys Gly Ile Val Gly Ala Ile Ala Gln Arg Asp Val Ala Glu Ile<br>1                 5                     10                 15 | 48 |
| ctt ctt gaa ggt tta cgt cgt ctg gaa tac cgc gga tat gac tct gcc<br>Leu Leu Glu Gly Leu Arg Arg Leu Glu Tyr Arg Gly Tyr Asp Ser Ala<br>              20                   25                    30 | 96 |
| ggt ctg gcc gtt gtt gat gca gaa ggt cat atg acc cgc ctg cgt cgc<br>Gly Leu Ala Val Val Asp Ala Glu Gly His Met Thr Arg Leu Arg Arg<br>        35                    40                    45 | 144 |
| ctc ggt aaa gtc cag atg ctg gca cag gca gcg gaa gaa cat cct ctg<br>Leu Gly Lys Val Gln Met Leu Ala Gln Ala Ala Glu Glu His Pro Leu<br>50                    55                    60 | 192 |
| cat ggc ggc act ggt att gct cac act cgc tgg gcg acc cac ggt gaa<br>His Gly Gly Thr Gly Ile Ala His Thr Arg Trp Ala Thr His Gly Glu<br>65                      70                    75                    80 | 240 |
| cct tca gaa gtg aat gcg cat ccg cat gtt tct gaa cac att gtg gtg<br>Pro Ser Glu Val Asn Ala His Pro His Val Ser Glu His Ile Val Val<br>              85                   90                    95 | 288 |
| gtg cat aac ggc atc atc gaa aac cat gaa ccg ctg cgt gaa gag cta<br>Val His Asn Gly Ile Ile Glu Asn His Glu Pro Leu Arg Glu Glu Leu<br>                100                    105                110 | 336 |
| aaa gcg cgt ggc tat acc ttc gtt tct gaa acc gac acc gaa gtg att<br>Lys Ala Arg Gly Tyr Thr Phe Val Ser Glu Thr Asp Thr Glu Val Ile<br>        115                    120                    125 | 384 |
| gcc cat ctg gtg aac tgg gag ctg aaa caa ggc ggg act ctg cgt gag<br>Ala His Leu Val Asn Trp Glu Leu Lys Gln Gly Gly Thr Leu Arg Glu<br>130                    135                    140 | 432 |
| gcc gtt ctg cgt gct atc ccg cag ctg cgt ggt gcg tac ggt aca gtg<br>Ala Val Leu Arg Ala Ile Pro Gln Leu Arg Gly Ala Tyr Gly Thr Val<br>145                    150                    155                    160 | 480 |
| atc atg gac tcc cgt cac ccg gat acc ctg ctg gcg gca cgt tct ggt<br>Ile Met Asp Ser Arg His Pro Asp Thr Leu Leu Ala Ala Arg Ser Gly<br>                165                    170                    175 | 528 |
| agt ccg ctg gtg att ggc ctg ggg atg ggc gaa aac ttt atc gct tct<br>Ser Pro Leu Val Ile Gly Leu Gly Met Gly Glu Asn Phe Ile Ala Ser<br>              180                    185                    190 | 576 |
| gac cag ctg gcg ctg ttg ccg gtg acc cgt cgc ttt atc ttc ctt gaa<br>Asp Gln Leu Ala Leu Leu Pro Val Thr Arg Arg Phe Ile Phe Leu Glu<br>        195                    200                    205 | 624 |
| gag ggc gat att gcg gaa atc act cgc cgt tcg gta aac atc ttc gat<br>Glu Gly Asp Ile Ala Glu Ile Thr Arg Arg Ser Val Asn Ile Phe Asp<br>210                    215                    220 | 672 |
| aaa act ggc gcg gaa gta aaa cgt cag gat atc gaa tcc aat ctg caa<br>Lys Thr Gly Ala Glu Val Lys Arg Gln Asp Ile Glu Ser Asn Leu Gln<br>225                    230                    235                    240 | 720 |
| tat gac gcg ggc gat aaa ggc att tac cgt cac tac atg cag aaa gag<br>Tyr Asp Ala Gly Asp Lys Gly Ile Tyr Arg His Tyr Met Gln Lys Glu<br>                245                    250                    255 | 768 |
| atc tac gaa cag ccg aac gcg atc aaa aac acc ctt acc gga cgc atc<br>Ile Tyr Glu Gln Pro Asn Ala Ile Lys Asn Thr Leu Thr Gly Arg Ile<br>                260                    265                270 | 816 |

```
agc cac ggt cag gtt gat tta agc gag ctg gga ccg aac gcc gac gaa      864
Ser His Gly Gln Val Asp Leu Ser Glu Leu Gly Pro Asn Ala Asp Glu
        275                 280                 285 ctg ctg tcg aag gtt gag cat att cag atc ctc gcc tgt ggt act tct      912
Leu Leu Ser Lys Val Glu His Ile Gln Ile Leu Ala Cys Gly Thr Ser
    290                 295                 300 tat aac tcc ggt atg gtt tcc cgc tac tgg ttt gaa tcg cta gca ggt      960
Tyr Asn Ser Gly Met Val Ser Arg Tyr Trp Phe Glu Ser Leu Ala Gly
305                 310                 315                 320 att ccg tgc gac gtc gaa atc gcc tct gaa ttc cgc tat cgc aaa tct     1008
Ile Pro Cys Asp Val Glu Ile Ala Ser Glu Phe Arg Tyr Arg Lys Ser
                325                 330                 335 gcc gtg cgt cgt aac agc ctg atg atc acc ttg tca cag tct ggc gaa     1056
Ala Val Arg Arg Asn Ser Leu Met Ile Thr Leu Ser Gln Ser Gly Glu
            340                 345                 350 acc gcg gat acc ctg gct ggc ctg cgt ctg tcg aaa gag ctg ggt tac     1104
Thr Ala Asp Thr Leu Ala Gly Leu Arg Leu Ser Lys Glu Leu Gly Tyr
        355                 360                 365 ctt ggt tca ctg gca atc tgt aac gtt ccg ggt tct tct ctg gtg cgc     1152
Leu Gly Ser Leu Ala Ile Cys Asn Val Pro Gly Ser Ser Leu Val Arg
    370                 375                 380 gaa tcc gat ctg gcg cta atg acc aac gcg ggt aca gaa atc ggc gtg     1200
Glu Ser Asp Leu Ala Leu Met Thr Asn Ala Gly Thr Glu Ile Gly Val
385                 390                 395                 400 gca tcc act aaa gca ttc acc act cag tta act gtg ctg ttg atg ctg     1248
Ala Ser Thr Lys Ala Phe Thr Thr Gln Leu Thr Val Leu Leu Met Leu
                405                 410                 415 gtg gcg aag ctg tct cgc ctg aaa ggt ctg gat gcc tcc att gaa cat     1296
Val Ala Lys Leu Ser Arg Leu Lys Gly Leu Asp Ala Ser Ile Glu His
            420                 425                 430 gac atc gtg cat ggt ctg cag gcg ctg ccg agc cgt att gag cag atg     1344
Asp Ile Val His Gly Leu Gln Ala Leu Pro Ser Arg Ile Glu Gln Met
        435                 440                 445 ctg tct cag gac aaa cgc att gaa gcg ctg gca gaa gat ttc tct gac     1392
Leu Ser Gln Asp Lys Arg Ile Glu Ala Leu Ala Glu Asp Phe Ser Asp
    450                 455                 460 aaa cat cac gcg ctg ttc ctg agc cgt ggc gat cag tac cca atc gcg     1440
Lys His His Ala Leu Phe Leu Ser Arg Gly Asp Gln Tyr Pro Ile Ala
465                 470                 475                 480 ctg gaa ggc gca ttg aag ttg aaa gag atc tct tac att cac gct gaa     1488
Leu Glu Gly Ala Leu Lys Leu Lys Glu Ile Ser Tyr Ile His Ala Glu
                485                 490                 495 gcc tac gct gct ggc gaa ctg aaa cac ggt ccg ctg gcg cta att gat     1536
Ala Tyr Ala Ala Gly Glu Leu Lys His Gly Pro Leu Ala Leu Ile Asp
            500                 505                 510 gcc gat atg ccg gtt att gtt gtt gca ccg aac aac gaa ttg ctg gaa     1584
Ala Asp Met Pro Val Ile Val Val Ala Pro Asn Asn Glu Leu Leu Glu
        515                 520                 525 aaa ctg aaa tcc aac att gaa gaa gtt cgc gcg cgt ggc ggt cag ttg     1632
Lys Leu Lys Ser Asn Ile Glu Glu Val Arg Ala Arg Gly Gly Gln Leu
    530                 535                 540 tat gtc ttc gcc gat cag gat gcg ggt ttt gta agt agc gat aac atg     1680
Tyr Val Phe Ala Asp Gln Asp Ala Gly Phe Val Ser Ser Asp Asn Met
545                 550                 555                 560 cac atc atc gag atg ccg cat gtg gaa gag gtg att gca ccg atc ttc     1728
His Ile Ile Glu Met Pro His Val Glu Glu Val Ile Ala Pro Ile Phe
                565                 570                 575 tac acc gtt ccg ctg cag ctg ctg gct tac cat gtc gcg ctg atc aaa     1776
Tyr Thr Val Pro Leu Gln Leu Leu Ala Tyr His Val Ala Leu Ile Lys
```

```
                580                 585                 590
ggc acc gac gtt gac cag ccg cgt aac ctg gca aaa tcg gtt acg gtt    1824
Gly Thr Asp Val Asp Gln Pro Arg Asn Leu Ala Lys Ser Val Thr Val
        595                 600                 605 gag taa                                                             1830
Glu
```

<210> SEQ ID NO 31
<211> LENGTH: 609
<212> TYPE: PRT
<213> ORGANISM: Escherichia coli

<400> SEQUENCE: 31

```
Met Cys Gly Ile Val Gly Ala Ile Ala Gln Arg Asp Val Ala Glu Ile
  1               5                  10                  15

Leu Leu Glu Gly Leu Arg Arg Leu Glu Tyr Arg Gly Tyr Asp Ser Ala
                 20                  25                  30

Gly Leu Ala Val Val Asp Ala Glu Gly His Met Thr Arg Leu Arg Arg
             35                  40                  45

Leu Gly Lys Val Gln Met Leu Ala Gln Ala Ala Glu His Pro Leu
 50                  55                  60

His Gly Gly Thr Gly Ile Ala His Thr Arg Trp Ala Thr His Gly Glu
 65                  70                  75                  80

Pro Ser Glu Val Asn Ala His Pro His Val Ser Glu His Ile Val Val
                 85                  90                  95

Val His Asn Gly Ile Ile Glu Asn His Glu Pro Leu Arg Glu Glu Leu
                100                 105                 110

Lys Ala Arg Gly Tyr Thr Phe Val Ser Glu Thr Asp Thr Glu Val Ile
                115                 120                 125

Ala His Leu Val Asn Trp Glu Leu Lys Gln Gly Gly Thr Leu Arg Glu
            130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
                180                 185                 190

Asp Gln Leu Ala Leu Leu Pro Val Thr Arg Arg Phe Ile Phe Leu Glu
            195                 200                 205

Glu Gly Asp Ile Ala Glu Ile Thr Arg Arg Ser Val Asn Ile Phe Asp
        210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
                260                 265                 270

Ser His Gly Gln Val Asp Leu Ser Glu Leu Gly Pro Asn Ala Asp Glu
            275                 280                 285

Leu Leu Ser Lys Val Glu His Ile Gln Ile Leu Ala Cys Gly Thr Ser
        290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335
```

```
Ala Val Arg Arg Asn Ser Leu Met Ile Thr Leu Ser Gln Ser Gly Glu
            340                 345                 350

Thr Ala Asp Thr Leu Ala Gly Leu Arg Leu Ser Lys Glu Leu Gly Tyr
        355                 360                 365

Leu Gly Ser Leu Ala Ile Cys Asn Val Pro Gly Ser Ser Leu Val Arg
    370                 375                 380

Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
            405                 410                 415

Val Ala Lys Leu Ser Arg Leu Lys Gly Leu Asp Ala Ser Ile Glu His
            420                 425                 430

Asp Ile Val His Gly Leu Gln Ala Leu Pro Ser Arg Ile Glu Gln Met
        435                 440                 445

Leu Ser Gln Asp Lys Arg Ile Glu Ala Leu Ala Glu Asp Phe Ser Asp
    450                 455                 460

Lys His His Ala Leu Phe Leu Ser Arg Gly Asp Gln Tyr Pro Ile Ala
465                 470                 475                 480

Leu Glu Gly Ala Leu Lys Leu Lys Glu Ile Ser Tyr Ile His Ala Glu
            485                 490                 495

Ala Tyr Ala Ala Gly Glu Leu Lys His Gly Pro Leu Ala Leu Ile Asp
            500                 505                 510

Ala Asp Met Pro Val Ile Val Val Ala Pro Asn Asn Glu Leu Leu Glu
        515                 520                 525

Lys Leu Lys Ser Asn Ile Glu Glu Val Arg Ala Arg Gly Gly Gln Leu
    530                 535                 540

Tyr Val Phe Ala Asp Gln Asp Ala Gly Phe Val Ser Ser Asp Asn Met
545                 550                 555                 560

His Ile Ile Glu Met Pro His Val Glu Glu Val Ile Ala Pro Ile Phe
            565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
        595                 600                 605

Glu
```